US011492595B2

(12) United States Patent
Paganelli et al.

(10) Patent No.: US 11,492,595 B2
(45) Date of Patent: **\*Nov. 8, 2022**

(54) ENCAPSULATED LIVER TISSUE

(71) Applicant: MORPHOCELL TECHNOLOGIES INC., Montreal (CA)

(72) Inventors: Massimiliano Paganelli, Outremont (CA); Claudia Raggi, Outremont (CA); Ariella Shikanov, Ann Arbor, MI (US)

(73) Assignee: MORPHOCELL TECHNOLOGIES INC., Montreal (CA)

(*) Notice: Subject to any disclaimer, the term of this patent is extended or adjusted under 35 U.S.C. 154(b) by 438 days.

This patent is subject to a terminal disclaimer.

(21) Appl. No.: 16/463,093

(22) PCT Filed: Nov. 23, 2017

(86) PCT No.: PCT/CA2017/051404
§ 371 (c)(1),
(2) Date: May 22, 2019

(87) PCT Pub. No.: WO2018/094522
PCT Pub. Date: May 31, 2018

(65) Prior Publication Data
US 2019/0284535 A1    Sep. 19, 2019

Related U.S. Application Data

(60) Provisional application No. 62/425,811, filed on Nov. 23, 2016.

(51) Int. Cl.
| | | |
|---|---|---|
| *C12N 5/071* | (2010.01) | |
| *A61K 35/407* | (2015.01) | |
| *A61L 27/38* | (2006.01) | |
| *G01N 33/50* | (2006.01) | |
| *G01N 33/48* | (2006.01) | |
| *A61P 1/16* | (2006.01) | |
| *A61L 27/18* | (2006.01) | |
| *A61L 27/34* | (2006.01) | |

(52) U.S. Cl.
CPC ......... *C12N 5/0671* (2013.01); *A61K 35/407* (2013.01); *A61L 27/3804* (2013.01); *A61L 27/3808* (2013.01); *A61L 27/3834* (2013.01); *G01N 33/48* (2013.01); *G01N 33/5014* (2013.01); *G01N 33/5067* (2013.01); *A61L 27/18* (2013.01); *A61L 27/34* (2013.01); *A61L 27/3826* (2013.01); *A61L 27/3886* (2013.01); *A61L 2430/28* (2013.01); *A61P 1/16* (2018.01); *C12N 2533/40* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 11,096,388 B2* | 8/2021 | Paun | A01N 1/0247 |
| 2014/0274802 A1 | 9/2014 | Shepherd et al. | |
| 2014/0289877 A1 | 9/2014 | Taniguchi et al. | |
| 2015/0253309 A1* | 9/2015 | Marx | C12M 27/00 435/284.1 |

FOREIGN PATENT DOCUMENTS

| | | |
|---|---|---|
| EP | 2412800 A1 | 2/2012 |
| JP | 2016512964 | 5/2016 |
| JP | 2016514032 | 5/2016 |
| WO | WO 2014/098603 | 6/2014 |
| WO | WO 2014127170 | 8/2014 |
| WO | WO 2014/153004 | 9/2014 |
| WO | WO 2016/064648 | 4/2016 |
| WO | WO 2016/161941 | 10/2016 |
| WO | WO 2017048193 | 3/2017 |

OTHER PUBLICATIONS

Lancaster e al, Science, 2014, vol. 345, Issue 6194, 11 pages (Year: 2014).*
Schepers et al, Lab on a Chip, Jul. 20156, 16, 2644-2653. (Year: 2016).*
Song et al, Scientific Reports, 2015, vol. 5, No. 16884, 13 pages. (Year: 2015).*
International Search Report and Written Opinion for PCT/CA2017/051404, dated Feb. 27, 2018.
Du et al., *Biomaterials* 35 (2014) 6006-6014.
Lee, *Liver Tissue Engineering Based on Poly(Ethylene Glycol) Hydrogels*, 2010, Thesis (Ph.D.), Stanford University.
Meier et al., *Journal of Hepatology* 62 (2015) 634-641.
Nantasanti et al., *Stem Cells Translational Medicine* 5(3) (2016) 325-330.
Yamada et al., *Biomaterials* 33 (2012) 8304-8315.
Extended European Search Report Issued in Corresponding European Application No. 17874439.7, dated Oct. 4, 2019.
Lee & Cho, "Liver Tissue Engineering: Recent Advances in the Development of a Bio-Artificial Liver," Biotechnology and Bioprocess Engineering, 17(3): 427-438, 2012.
Phelps, et al., "Maleimide Cross-Linked Bioactive PEG Hydrogel Exhibits Improved Reaction Kinetics and Cross-Linking for Cell Encapsulation and In Situ Delivery," Advanced Materials, 24(1): 64-70, 2011.

(Continued)

*Primary Examiner* — Allison M Fox
(74) *Attorney, Agent, or Firm* — Norton Rose Fulbright US LLP

(57) ABSTRACT

The present disclosure provides an encapsulated liver tissue that can be used in vivo to improve liver functions, in vitro to determine the hepatic metabolism and/or hepatotoxicity of an agent and ex vivo to remove toxic compounds from patients' biological fluid. The encapsulated liver tissue comprises at least one liver organoid at least partially covered with a biocompatible cross-linked polymer. Processes for making the encapsulated liver tissue are also provided.

19 Claims, 40 Drawing Sheets

Specification includes a Sequence Listing.

(56) References Cited

OTHER PUBLICATIONS

Tsang, et al., "Fabrication of 3D Hepatic Tissues by Addictive Photopatterning of Cellular Hydrogels," The FASEB Journal, 21(3): 790-801, 2007.
Underhill, et al., "Assessment of Hepatocellular Function Within PEG Hydrogels," 28(2): 256-270, 2007.
Takebe et al., "Vascularized and functional human liver from an iPSC-derived organ bud transplant," Nature, 499: 481-484, 2013.
English translation of Office Action issued in Korean Patent Application No. 10-2019-7017810, dated Mar. 28, 2022.
Gjorevski et al., "Designer matrices for intestinal stem cell and organoid culture," Nature, 539(7630):560-564, 2016.

* cited by examiner

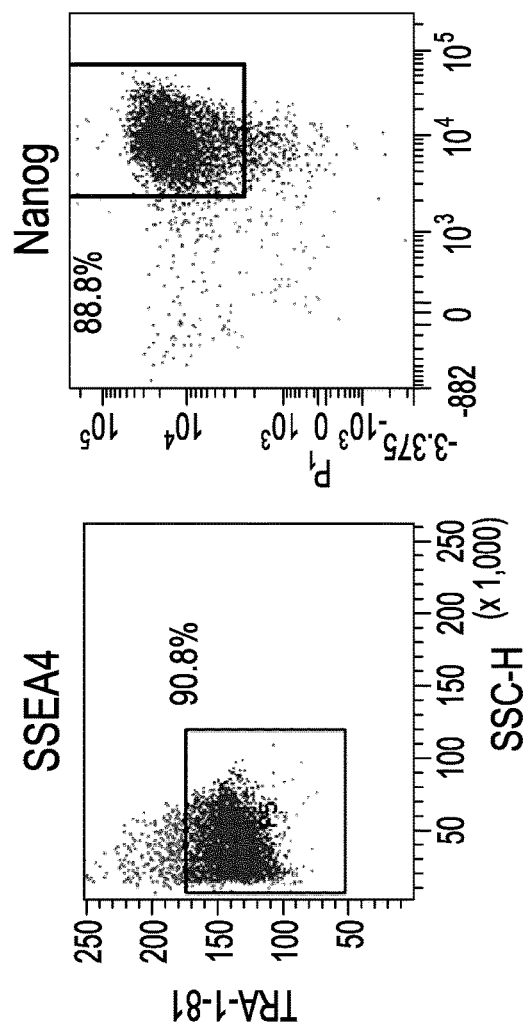
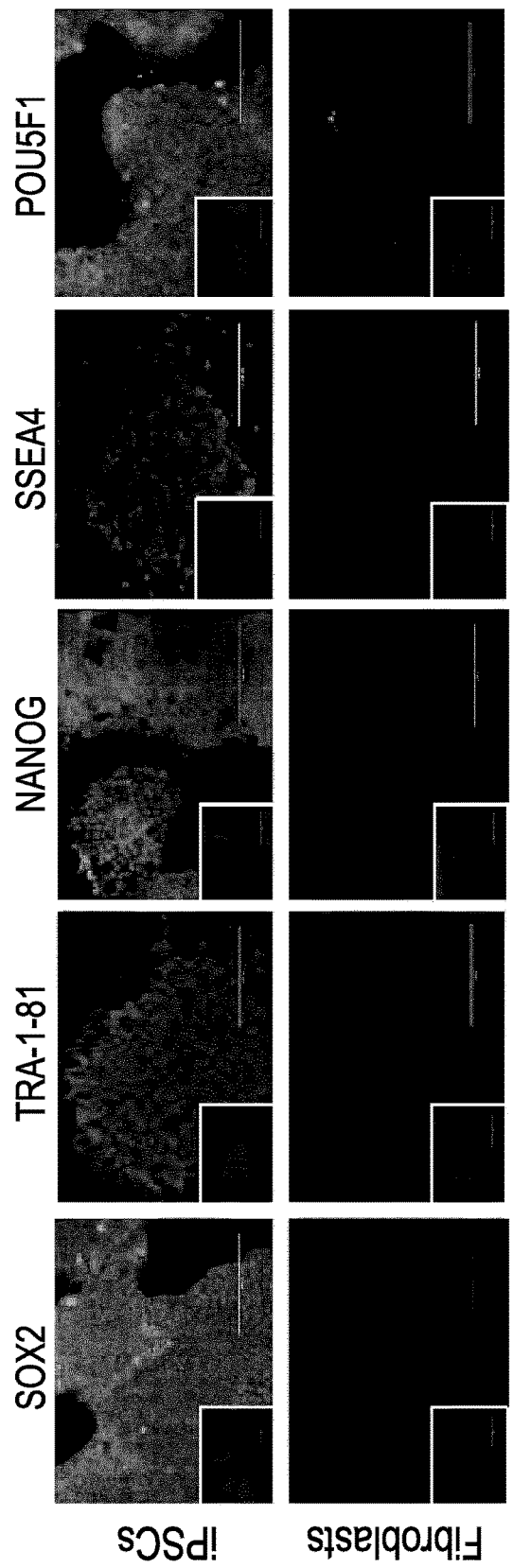
Figure 1C
Figure 1D

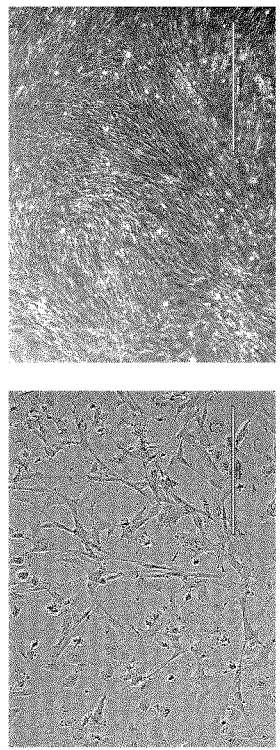
Figure 2I
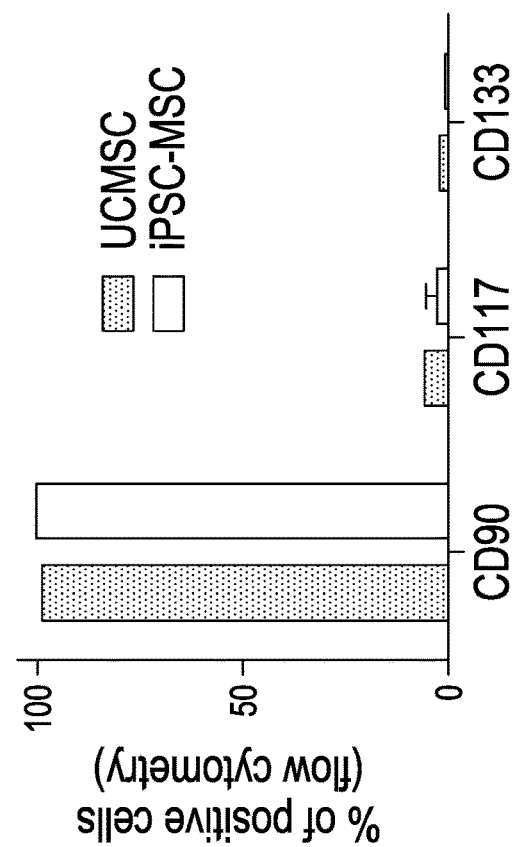
Figure 2J
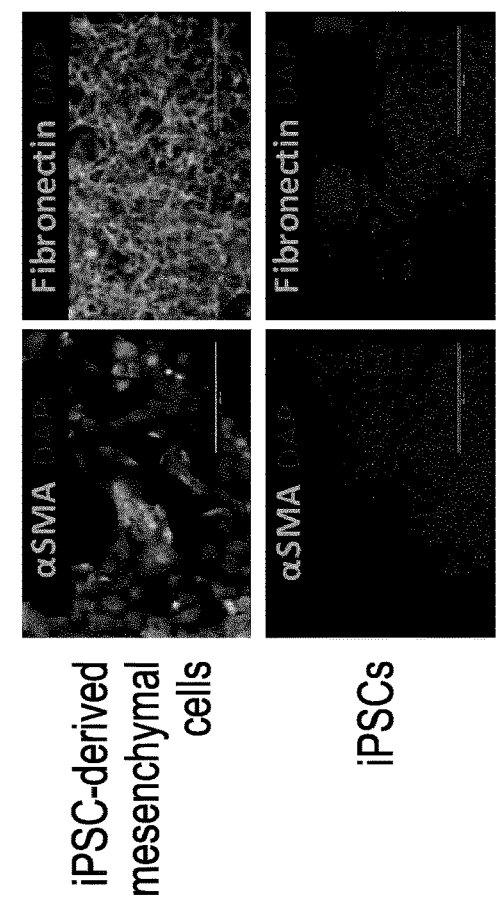

iPSC-MPC-derived osteocytes | iPSC-MPC-derived adipocytes 4 weeks post-implantation 1 week post-implantation

ENCAPSULATED LIVER TISSUE

CROSS-REFERENCE TO RELATED APPLICATIONS AND DOCUMENTS

This application is a national phase application under 35 U.S.C. 0 371 of International Application No. PCT/CA2017/051404 filed Nov. 23, 2017, which claims priority from U.S. provisional patent application 62/425,811 filed on Nov. 23, 2016, the contents of both of which are incorporated herein in their entirety.

TECHNOLOGICAL FIELD

The present disclosure concern liver organoids comprising hepatic, mesenchymal and optionally endothelial cells, which can be encapsulated within a biocompatible cross-linked polymer, as well as their use for restoring or improving liver functions and determining the hepatic metabolism and/or hepatotoxicity of an agent (a lead compound, or an investigational new drug for example).

BACKGROUND

Cirrhosis and chronic liver failure (LF) are the common outcomes of most progressive liver diseases. The loss of the liver's synthetic and detoxifying functions entails major systemic consequences such as ascites, hepatic encephalopathy and gastrointestinal bleeding, among others. Additionally, almost 10% of all non-cancer, liver-related deaths are due to acute LF, which is an extremely severe, progressive syndrome resulting from a sudden insult on the liver exceeding the organ's innate regenerative capacity. Acute LF in children and adolescents has a poor outcome, with only 50% of patients surviving with their native liver. Moreover, there are a significant number of liver conditions, such as inborn errors of liver metabolism (urea cycle defects, Criggler-Najjar syndrome, familial hypercholesterolemia, etc.), that do not lead to liver failure but entail severe hepatic and extrahepatic consequences. Although individually rare, when considered together, liver-based metabolic diseases represent more than 10% of pediatric liver transplants. A treatment is available for only few of such conditions. In all cases the treatment reduces the symptoms and improve the prognosis, but does not cure the disease. The standard of care for acute, chronic and acute-on-chronic LF, as for most inborn errors of liver metabolism, is liver transplantation, but only 400 transplants are performed each year in Canada for over 5 000 liver deaths/year. For the minority of patients who are eligible to liver transplantation, death while waiting for a suitable organ donor is far too common. Children with acute LF need to be transplanted within days from the diagnosis, before their disease becomes irreversibly too severe (20% die waiting for a donor). Infants are at even greater risk, with almost half dying before transplantation and 50% of those transplanted dying post-operatively. Furthermore, liver transplantation has major limitations. Besides entailing a significant short-term mortality and morbidity risk, it requires lifelong immunosuppression and is often complicated by severe long-term hepatic and extra-hepatic problems. The outcome of children with inborn errors of liver metabolism is far better, but such patients have very low priority on the waiting list and often develop systemic complications while waiting for transplant. Such high risks are disproportioned for many patients with acute LF who just need a temporary replacement of liver functions while their liver regenerates, as well as for the many metabolic liver diseases that are characterized by a single enzyme deficiency but a normal liver parenchyma. Thus, there is an urgent need for new therapies to restore liver functions in children and adults with LF and metabolic liver diseases.

Several alternative approaches based on partial liver transplantation or extracorporeal detoxifying devices have been developed over the years to temporarily replace liver functions, with mostly unsatisfactory results. In the past two decades, transplantation of primary liver cells from healthy donors was shown to induce a transient improvement in patients with chronic LF and inborn errors of liver metabolism. Such an approach showed the feasibility of cell therapy for liver diseases, but it is limited by organ shortage, the need for repeated injections and lifelong immunosuppression, and the extreme variability of cell quality.

Further, the gold standard toxicological approach for evaluating chemical toxicity involves complex in vivo studies which are both time consuming and costly. Animal testing raises concerns about animal welfare, time and cost. In addition, the predictive accuracy of rodent in vivo testing for human adverse health effects has become a matter of dispute in recent years. The use of in vitro model systems in toxicity testing has many advantages including the decrease in animal numbers, the reduced cost of animal maintenance and care, small quantity of a chemical needed for testing, shortening of the time needed, and increase in throughput for evaluating multiple chemicals and their metabolites. In vitro systems also allow to study chemical metabolism, evaluate the mechanisms of toxicity, measure enzyme kinetics, and examine dose-response relationships. The liver has a pivotal role in metabolizing, activating or inactivating any compound absorbed through the bowel or injected via subcutaneous, intramuscular or intravenous routes. The use of primary human hepatocytes has been limited by their scarce availability and extreme variability in their quality and in vitro metabolic activity, whereas available cell lines are not fully representative of liver physiology. There is thus a need establishing workable in vitro culture systems for assessing how lead compounds or investigational drugs are metabolized by the liver and whether induce liver toxicity.

BRIEF SUMMARY

According to a first aspect, the present disclosure provides an encapsulated liver tissue comprising at least one liver organoid at least partially covered with a first biocompatible cross-linked polymer. The liver organoid comprises a cellular core comprising hepatic, mesenchymal and optionally endothelial cells. The liver organoid has a substantially spherical shape and a relative diameter between about 50 and about 500 µm. In an embodiment, the at least one liver organoid is substantially covered with the first biocompatible cross-linked polymer. In yet another embodiment, the cellular core comprises hepatocytes and/or biliary epithelial cells. In yet another embodiment, the first biocompatible cross-linked polymer comprises poly(ethylene) glycol (PEG). In still another embodiment, the encapsulated liver tissue further comprises a second biocompatible cross-linked polymer and wherein the first biocompatible cross-linked polymer is at least partially covered by the second biocompatible cross-linked polymer. In an embodiment, the first biocompatible cross-linked polymer is substantially covered with the second biocompatible cross-linked polymer. In yet another embodiment, the first biocompatible cross-linked polymer is at least partially biodegradable and/or the second biocompatible cross-linked polymer is at least partially resistant to biodegradation. In still another embodiment, the second biocompatible cross-linked polymer comprises poly(ethylene) glycol (PEG). In yet another embodiment, the encapsulated liver tissue comprises a plurality of liver organoids dispersed throughout the first biocompatible cross-linked polymer.

According to a second aspect, the present disclosure provides a process for making an encapsulated liver tissue. Broadly, the process first comprises combining and culturing in suspension hepatic, mesenchymal and optionally endothelial cells so as to obtain at least one liver organoid having (i) a cellular core comprising hepatic, mesenchymal and optionally endothelial cells, (ii) a substantially spherical shape and (iii) a relative diameter between about 50 and about 500 µm. The process also comprises at least partially covering the at least one liver organoid with a first biocompatible cross-linked polymer. In an embodiment, the hepatic cells and mesenchymal cells are combined, prior to culturing, at a ratio of 1:0.2-7. In still another embodiment, the hepatic cells and endothelial cells are combined, prior to culturing, at a ratio of 1:0.2-1. In an embodiment, at least one of the hepatic, mesenchymal and endothelial cells is obtained from differentiating a stem cell, such as, for example, a pluripotent stem cell. In still another embodiment, the hepatic cells can be derived from the definitive endoderm, posterior foregut or hepatoblasts, can be hepatoblasts and/or hepatocytes. In still another embodiment, the mesenchymal cells are mesenchymal stem cells or mesenchymal progenitor cells. In yet another embodiment, the endothelial cells are endothelial progenitor cells. In an embodiment, the process comprises substantially covering the at least one liver organoid with the first biocompatible cross-linked polymer. In a further embodiment, the first biocompatible cross-linked polymer comprises poly(ethylene) glycol (PEG). In still another embodiment, the process comprises at least partially covering the first biocompatible cross-linked polymer with a second biocompatible cross-linked polymer. In yet another embodiment, the process comprises substantially covering the first biocompatible cross-linked polymer with the second biocompatible cross-linked polymer. In yet another embodiment, the first biocompatible cross-linked polymer is at least partially biodegradable and/or the second biocompatible cross-linked polymer is at least partially resistant to biodegradation. In an embodiment, the second biocompatible cross-linked polymer comprises poly(ethylene) glycol (PEG). In yet another embodiment, the process further comprises including a plurality of liver organoids in the first biocompatible cross-linked polymer.

According to a third aspect, the present disclosure provides an encapsulated liver tissue obtainable or obtained by the process described herein.

According to a fourth aspect, the present disclosure provides an encapsulated liver tissue as defined herein for the manufacture of a medicine.

According to a fifth aspect, the present disclosure provides an encapsulated liver tissue as defined herein for restoring or improving a liver function in a subject in need thereof. The encapsulated liver tissue can be used for treating or alleviating the symptoms associated with liver failure. In an embodiment, liver failure can be acute, chronic or acute-on-chronic liver failure. In still another embodiment, the encapsulated liver tissue can be used for treating or alleviating the symptoms associated to an inborn error of liver metabolism. In still another embodiment, the encapsulated liver tissue comprises a plurality of liver organoids in the first biocompatible cross-linked polymer. The subject can be a mammal, for example a human.

According to a sixth aspect, the present disclosure provides a method of restoring or improving a liver function in a subject in need thereof. Broadly, the method comprises contacting an effective amount of liver organoids of the encapsulated liver tissue described herein with a biological fluid of the subject so as to improve the liver function in the subject. In an embodiment, the method is for restoring or improving the liver function is for the treatment or the alleviations of symptoms associated with liver failure. In an embodiment, liver failure is acute, chronic or acute-on-chronic liver failure. In yet another embodiment, the method is for restoring or improving a liver function associated with an inborn error of metabolism. In still another embodiment, the encapsulated liver tissue comprises the first and the second biocompatible cross-linked polymer. The subject can be a mammal, for example a human.

According to a seventh aspect, the present disclosure provides a method of determining the hepatic metabolism and/or hepatotoxicity of an agent. Broadly, the method comprises: a) contacting the agent with the encapsulated liver tissue as described to obtain a test mixture; b) determining at least one agent-related hepatic metabolite or hepatic parameter in the test mixture; and c) comparing the at least one agent-related hepatic metabolite or hepatic parameter of step b) with a control agent-related hepatic metabolite or hepatic parameter to determine the hepatic metabolism and/or the hepatotoxicity of the agent. In an embodiment, the method is for determining if the agent induces hepatotoxicity in at least one cell type of the at least one liver organoid of the encapsulated tissue (such as, for example, in an hepatocyte or a biliary epithelial cell). In an embodiment, the method comprises contacting the agent with a first encapsulated liver tissue comprising a first liver organoid and a second encapsulated liver tissue comprising a second liver organoid and wherein the cells (for example the hepatocytes and/or the biliary epithelial cells) of the first liver organoid are allogeneic to the cells (for example the hepatocytes and/or the biliary epithelial cells) of the second liver organoid. In still another embodiment, the encapsulated liver tissue consists essentially of the first biocompatible cross-linked polymer and the at least one liver organoid.

According to an eight aspect, the present disclosure concerns a kit for determining the hepatic metabolism of an agent, the kit comprises the encapsulated liver tissue described herein and instructions for performing the method described herein. In an embodiment, the kit further comprises a tissue culture support. In still another embodiment, the tissue culture support comprises at least one well. In yet another embodiment, the encapsulated liver tissue is at the bottom of the at least one well.

BRIEF DESCRIPTION OF THE DRAWINGS

Having thus generally described the nature of the invention, reference will now be made to the accompanying drawings, showing by way of illustration, a preferred embodiment thereof, and in which:

FIGS. 1A to 1D illustrate an embodiment of human induced pluripotent stem cells (iPSCs) generated from peripheral blood mononuclear cells in strict xeno-free and feeder-free conditions. (A) Representative aspects of iPSCs colonies in E8 Flex medium on vitronectin (scale bar 1 000 µM top, 200 µM bottom) as determined by microscopy. (B) Expression of pluripotency genes (NANOG, POU5F1 and SOX2) in fibroblasts (light grey bars), embryonic stem cells (ESC, white bars) and iPSCs (diagonal bars) as determined by reverse transcription real-time PCR (RT-qPCR). (C) Representative flow cytometry analysis of the iPSCs showing high homogeneity of pluripotency markers (SSEA4 and TRA-1-81 (90.8% of gated cells), TRA-1-81 and NANOG (88.8% of gated cells) expression. (D) Expression of pluripotency markers (SOX2, TRA-1-81, NANOG, SSEA4 and POU5F1) in iPSCs (top row) as compared to skin fibroblasts (bottom row) (scale bar 200 μM) as determined by immunofluorescence. Inserts show nucleus (DAPI) staining.

FIGS. 2A to 2M illustrate the in vitro differentiation of iPSCs. (A) Upregulation of endoderm-specific genes (SOX17, FOXA2, CXCR4, GATA4) and downregulation of pluripotency genes (SOX2, NANOG, POU5F1) in iPSCs-derived endodermal cells (white bars) when compared to iPSCs (light gray bars) as measured by RT-qPCR. Results are show as logarithmic fold change in the various genes tested. (B) Expression of endoderm-specific markers (SOX17, FOXA2, CXCR4, GATA4) in iPSCs upon in vitro differentiation (scale bar 200 μM) as determined by immunofluorescence. Results are shown for the definitive endoderm (top row) and undifferentiated iPSCs (bottom row). Inserts show nucleus (DAPI) staining. (C) Representative flow cytometry analysis of iPSCs differentiated in definitive endoderm cells for the FOXA2, CXCR4 and SOX17 markers. 87.2% of cells are FOXA2$^+$ and CXCR4$^+$, 98.4% of which are also SOX17$^+$ (85.8% of triple-positive cells). (D) Increased expression of HNF4α in iPSC-derived ventral posterior foregut cells, which give rise to hepatic progenitor cells. Results are shown as fold change in mRNA expression of the HNF4α gene in iPSCs, iPSCs differentiated in definitive endoderm and in iPSCs differentiated in posterior foregut. (E) Upregulation of liver-specific genes (AFP, albumin and HNF4α) in iPSC-derived hepatocytes (white bars) as compared to undifferentiated iPSCs (light gray bars) as determined by RT-qPCR. Results are show as logarithmic fold change in the various genes tested (identified on the X-axis). (F) Expression of liver-specific markers (AFP, top panel; albumin, middle panel; E-cadherin, bottom panel) in iPSC-derived hepatocytes (right column) and undifferentiated iPSCs (left column) (scale bar 200 μM) as measured by immunofluorescence. (G) Representative morphology of iPSC-derived hepatocytes. (H) iPSC-derived hepatocytes acquire liver-specific functions such as CyP3A4 activity (left panel), albumin (middle panel) and urea (left panel) synthesis. Results are provided for undifferentiated iPSCs (labelled as "iPSC"), iPSC-derived hepatocytes (labelled as "iPSC-Heps"), iPSC-derived hepatocyte progenitors (labelled as "Hepatoblasts"), iPSC-derived endodermal cells (labelled as "endoderm") and primary human hepatocytes (labelled as "PHH"). The number in parentheses refers to the number of days of differentiation required to obtain each cell type from iPSCs. (I) Representative morphology of mesenchymal progenitors derived from iPSCs (scale bar 200 μM) as determined by microscopy. (J) Expression of line-specific markers as shown by immunofluorescence (smooth muscle actin (αSMA)—left, and fibronectin—right) or flow cytometry (CD90, CD117 and CD133) and iPSCs-derived mesenchymal progenitor cells (white bars). Results are shown as immunofluorescence (left panel) for iPSC-derived mesenchymal cells (top row) and undifferentiated iPSCs (lower row) (scale bar 200 μM). Results are also shown as flow cytometry (right panel) for umbilical cord matrix stem cells (UCMSC, light gray bars) and iPSC-derived mesenchymal cells (iPSC-MPCs, white bars). (K) iPSC-MPCs can be differentiated into osteocytes or adipocytes as respectively shown by Alizarin red S staining (top panel) and LipidTox staining. Scale bar 200 μm. (L) Characterization of iPSCs-derived endothelial progenitor cells (iEPC). Results are shown as representative morphology (top left panel, scale bar 200 μM) by microscopy, expression of line-specific markers (CD31) as measured by flow cytometry in HUVEC (light gray bar) and iPSC-differentiated endothelial progenitor cells (white bar) (top right panel) or by immunofluorescence (bottom panel) for iPSCs (left panel), iPSC-differentiated endothelial progenitor cells (middle panel) or HUVECs (right panel). (M) iEPCs were capable of forming 3D vascular structure when cultured in Matrigel® (endothelial tube formation assay) as shown by representative microscopy. Scale bar 1000 μm left panel, 200 μm right panel.

DETAILED DESCRIPTION

Encapsulated Liver Tissue

Figure 1B:
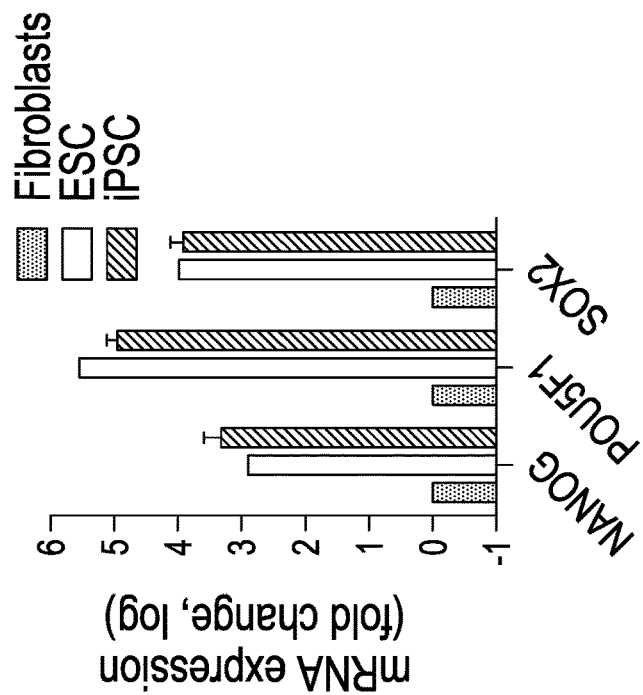
Figure 1B:
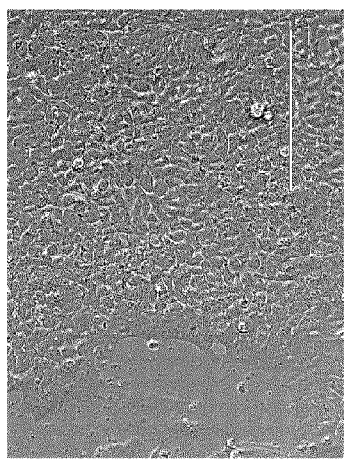
Figure 1A:
Figure 2A:
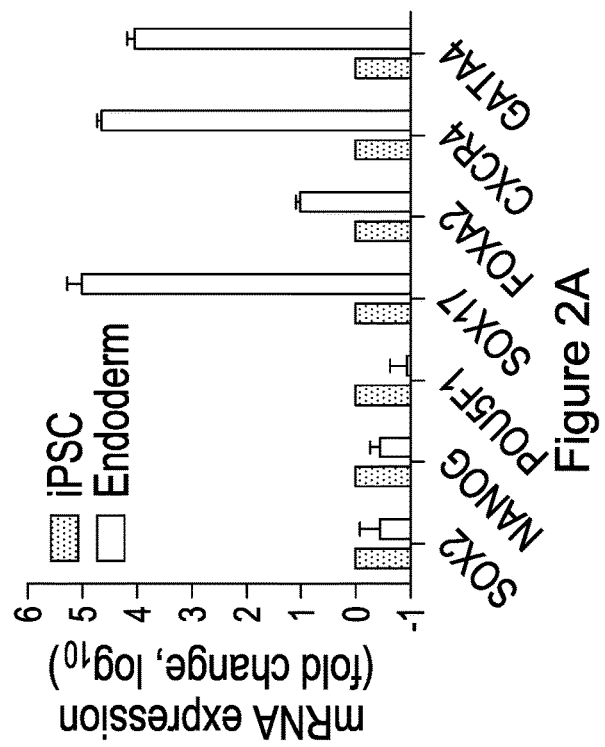
Figure 2B:
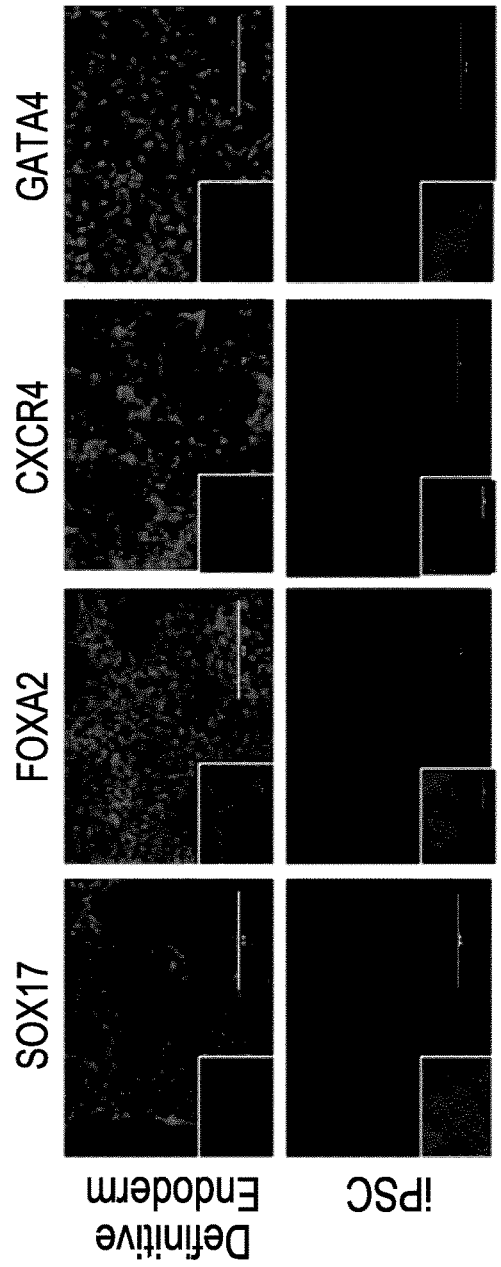
Figure 2C:
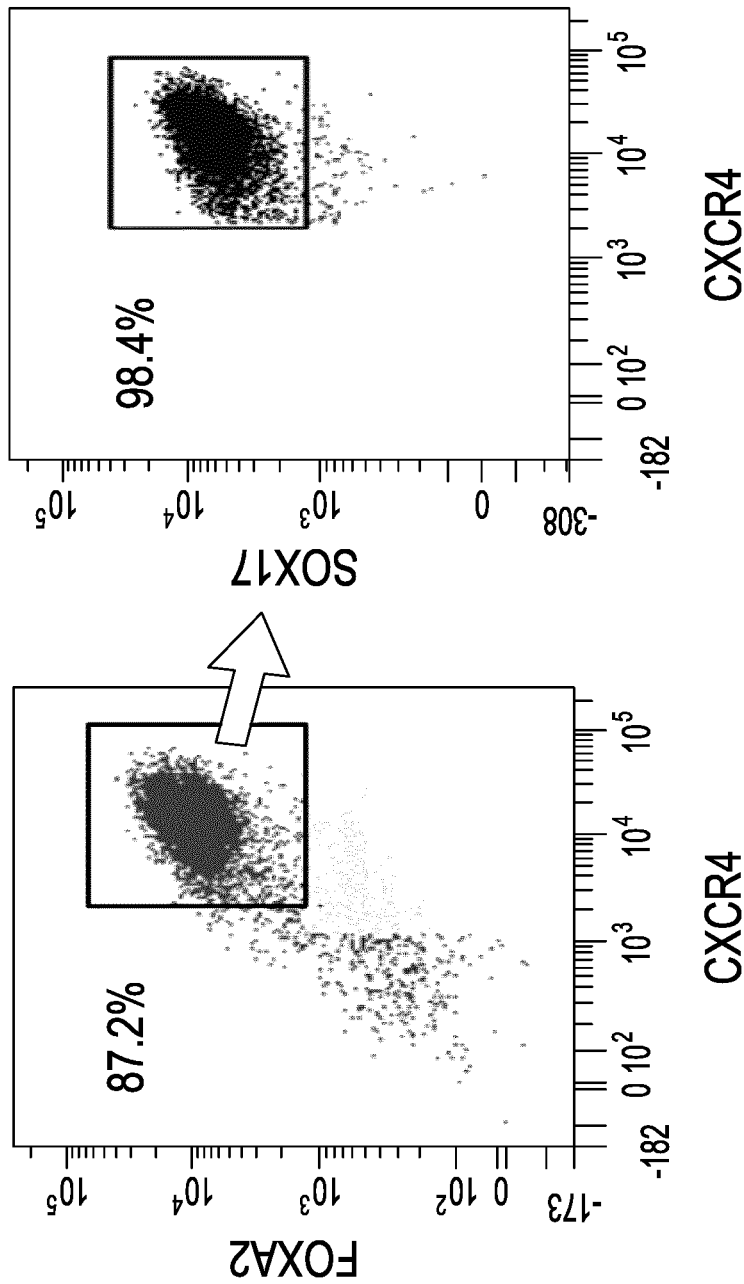
Figure 2D:
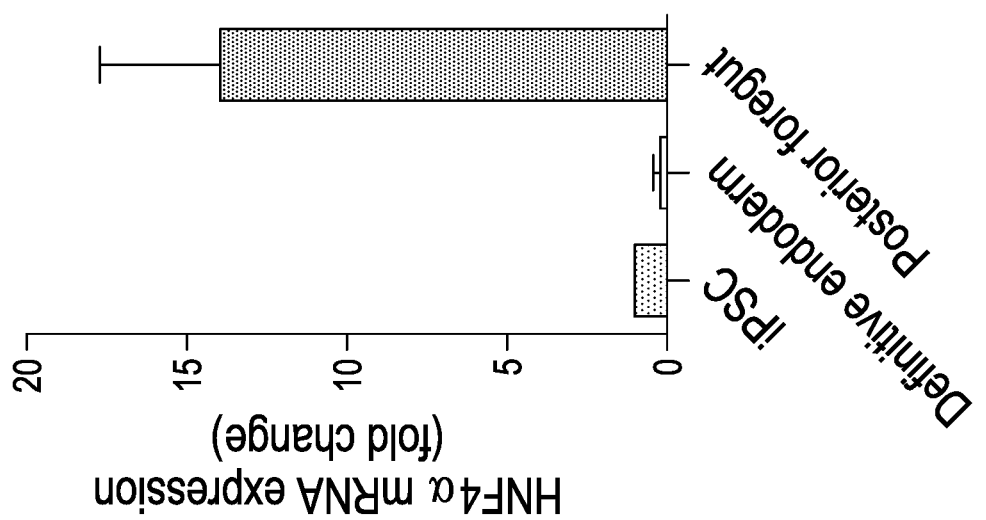
Figure 2E:
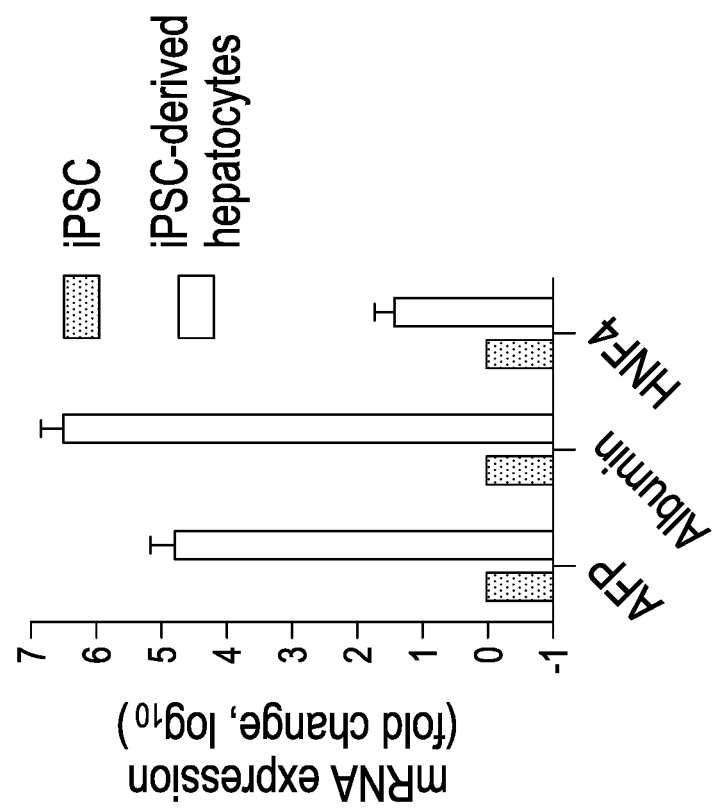
Figure 2F:
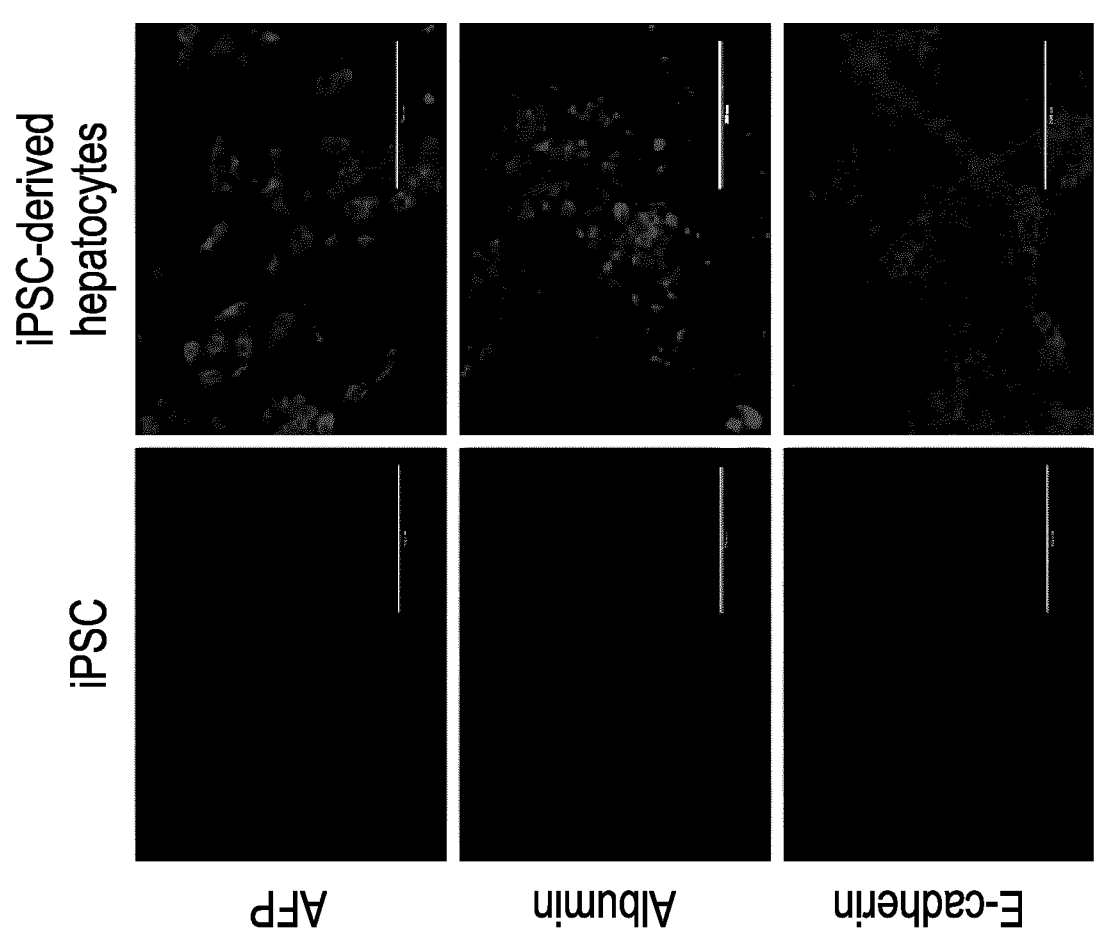
Figure 2G:
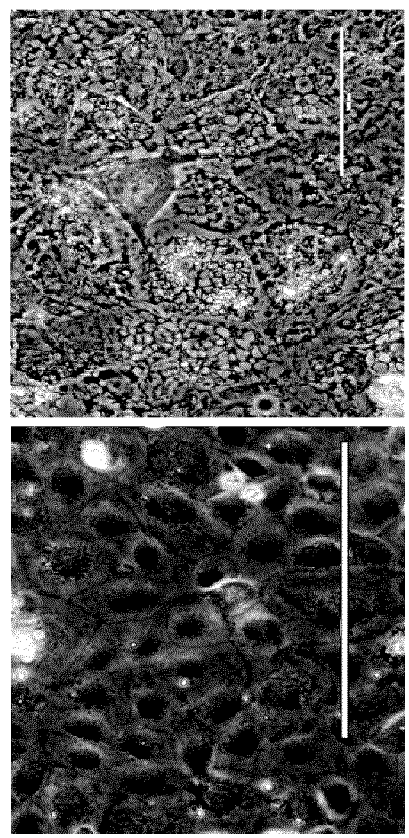
Figure 2H:
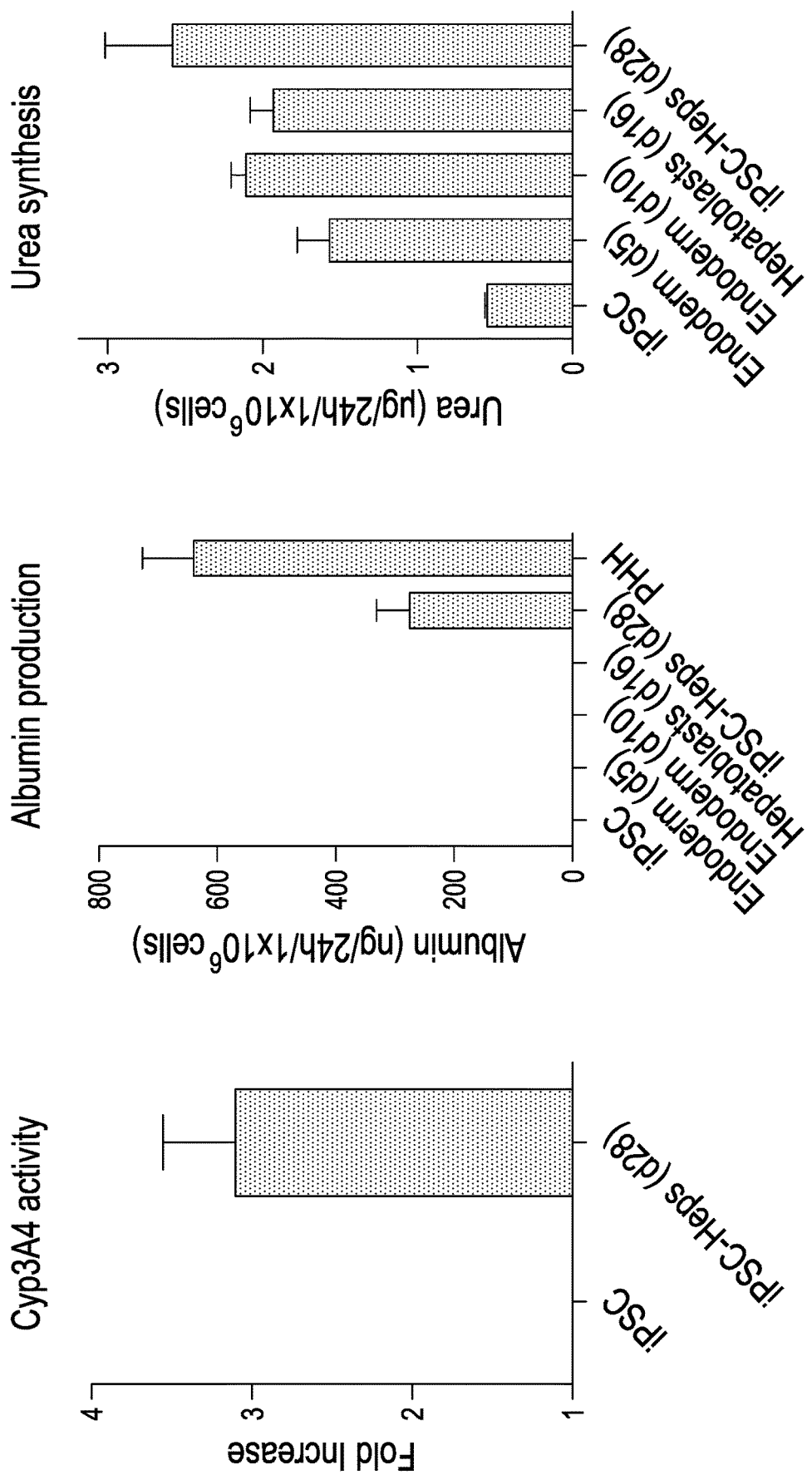
Figure 2K:
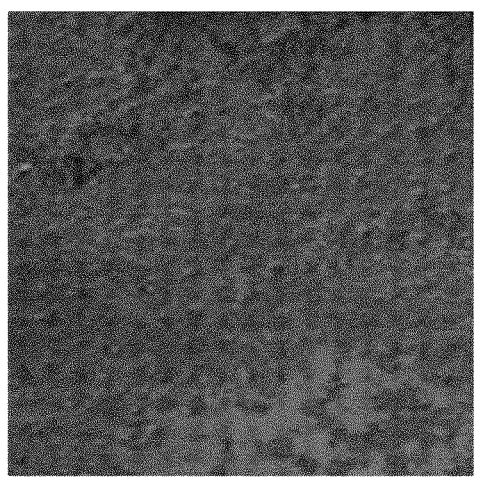
Figure 2K:
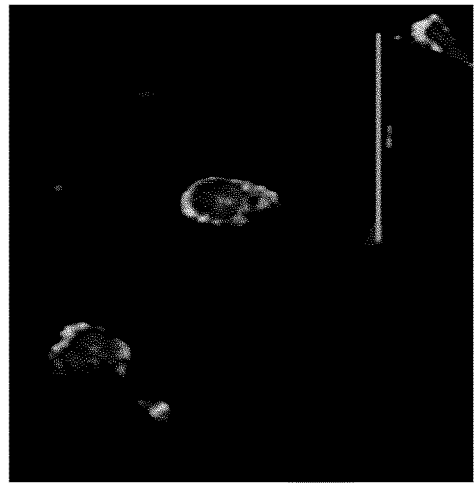
Figure 2L:
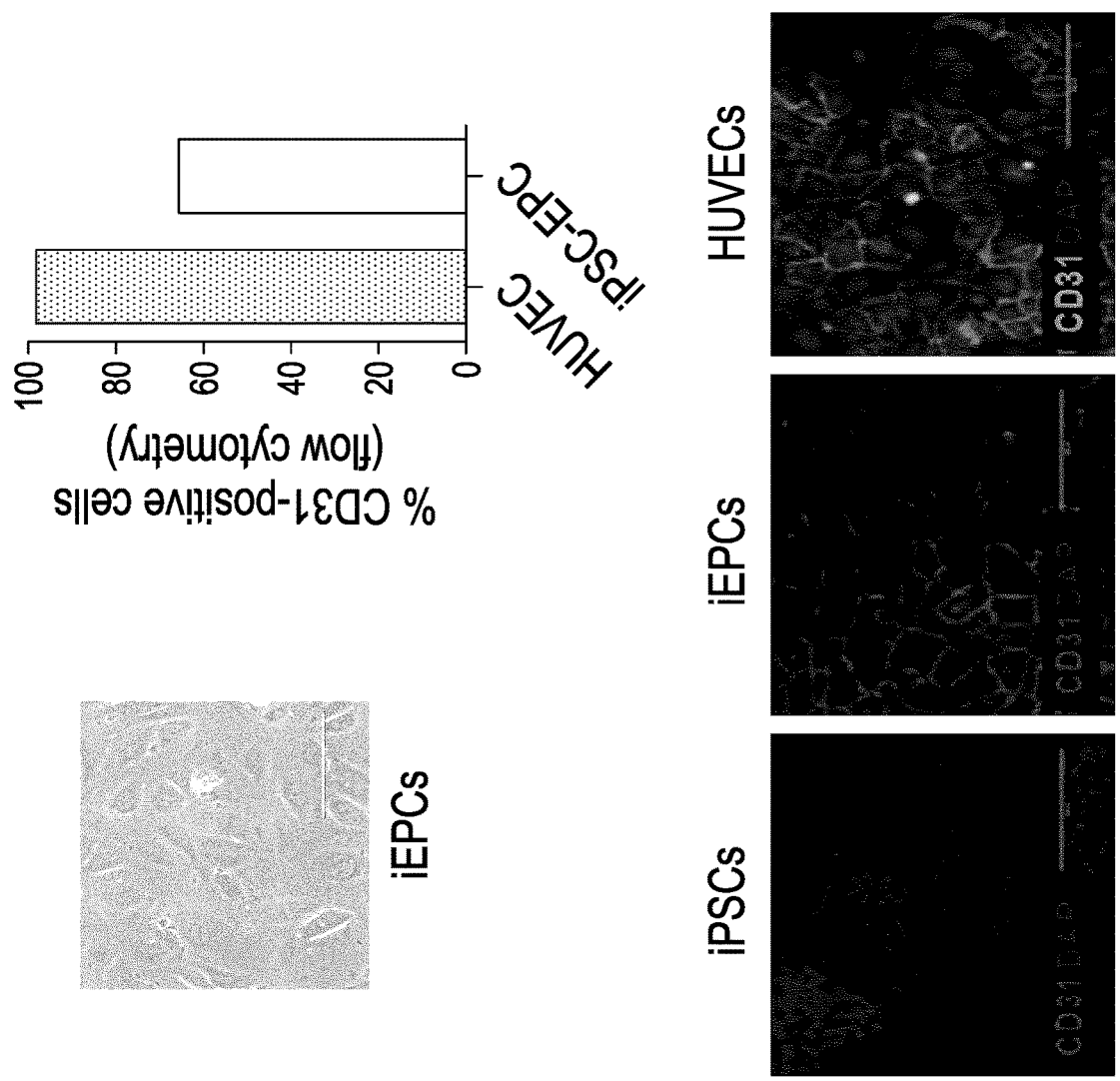
Figure 2M:
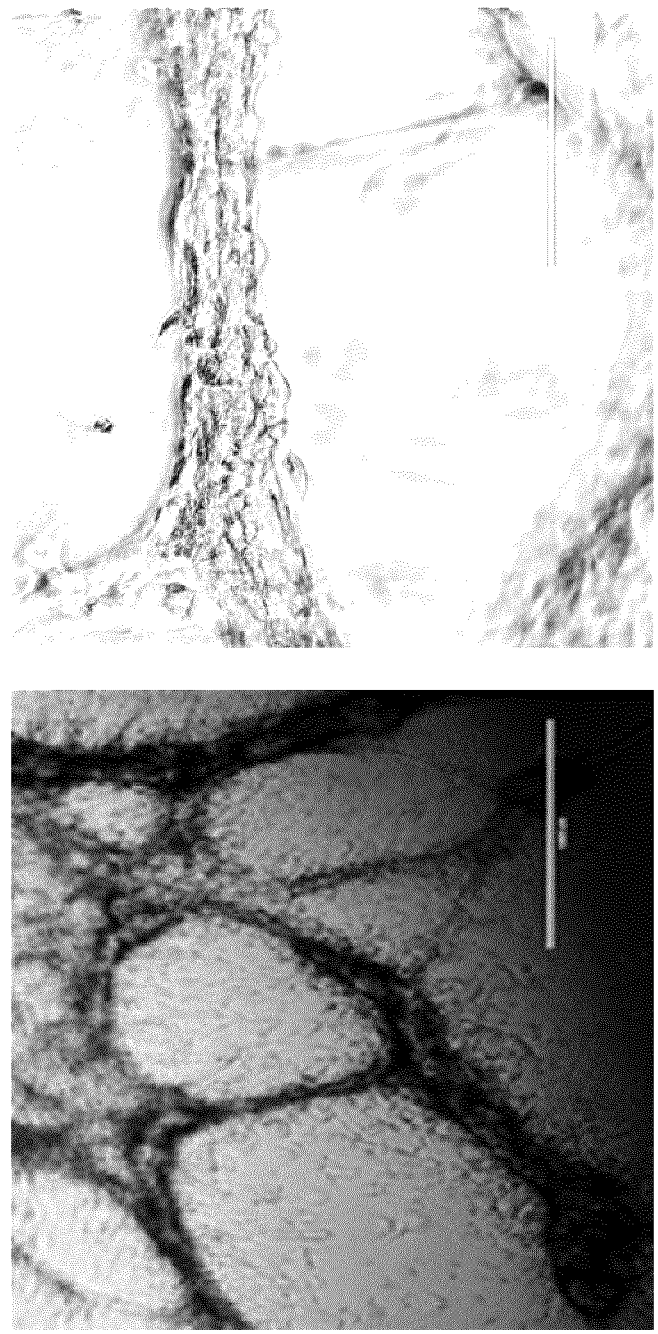

The encapsulated liver tissue comprises at least one (and in an embodiment a plurality of) liver organoid that is at least partially covered with a biocompatible cross-linked polymer. As used in the context of the present disclosure, a "liver organoid" refers to a mixture of cultured hepatic, mesenchymal and, optionally endothelial cells. In some embodiments, the liver organoid comprises a mixture of cultured hepatic, mesenchymal and endothelial cells. The liver organoid is generally spherical in shape and its surface may be irregular. The relative diameter of the liver organoid is between about 50 and about 500 μm. The cellular core of the liver is composed of hepatic cells, mesenchymal cells and, optionally, endothelial cells and, in some embodiments, the extracellular matrix the hepatic, mesenchymal and, optionally the endothelial cells have produced and assembled while being cultured. The liver organoid can be obtained by culturing the cells in suspension. In some embodiments, particularly prior to the culture/differentiation of the encapsulated liver tissue, the surface of the liver organoid is at least partially covered (and in some embodiments substantially covered) with endoderm (e.g., hepatic)-derived hepatic cells, such as, for example, hepatocytes and/or biliary epithelial cells. In another embodiment, the hepatic cells are dispersed throughout (but not necessary homogeneously) the cellular core. The organoids present in the encapsulated liver tissue are at least partially covered (and in some embodiments substantially covered) with a first biocompatible cross-linked polymer.

Prior to being encapsulated, the liver organoid is free of exogenous extracellular matrix. The liver organoid is substantially composed of the cultured hepatic, mesenchymal and, optionally, endothelial cells. Furthermore, the liver organoid (encapsulated or not in the first biocompatible polymer) exhibits liver functions, for example, the liver organoid is capable of synthesizing albumin as well clotting factors, exhibiting CyP3A4 activity, detoxifying ammonia to urea and performing liver-specific metabolism of drugs (i.e. tacrolimus or rifampicin).

The liver organoids of the present disclosure are substantially spherical in shape and have a relative diameter in the micrometer range (e.g., it is smaller than 1 mm in diameter). In an embodiment, the liver organoid, prior to its encapsulation, has a relative of at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480 or 490 μm. In yet another embodiment, the liver organoid, prior to its encapsulation, has a relative diameter equal to or lower than about 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70 or 60 µm. In another embodiment, the liver organoid, prior to its encapsulation, has a relative diameter between at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480 or 490 µm and equal to or lower than about 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70 or 60 µm. In some embodiments, the liver organoid, prior to its encapsulation, has a relative diameter between at least about 100, 110, 120, 130, 140, 150, 160, 170, 180, 190, 200, 210, 220, 230, 240, 250, 260, 270, 280 or 290 µm about and equal to or lower than about 300, 290, 280, 270, 260, 250, 240, 230, 220, 210, 200, 190, 180, 170, 160, 150, 140, 130, 120, 110, 100, 90, 80, 70 or 60 µm. In still yet another embodiment, the liver organoid prior to its encapsulation, has a relative diameter of at least about 100 µm and equal to or lower than about 300 µm. For example, the liver organoid, prior to its encapsulation, has a relative diameter of at least about 150, 160, 170, 180 or 190 µm and lower than 200, 190, 180, 170 or 160 µm. In yet a further embodiment, the liver organoid, prior to its encapsulation, has a relative diameter of at least about 150 µm and equal to lower than about 200 µm. The size of the liver organoids allows the cells it contains to increase their exposure to various nutrients and to biological fluid/cells in contact with the encapsulated liver tissue. In some embodiments, this allows the liver organoids to be able to remain viable and biologically active in vivo without the need to vascularize them with the host's vascular system (e.g., the vascular system of the host having received the encapsulated liver tissue).

The endodermal (hepatic) cells of the liver organoid can be dispersed through the entire organoid, and, in some embodiments, some of them can be located at the surface of the cellular core of the liver organoid. The hepatic cells of the liver organoid can be, for example, cells from the definitive endoderm, posterior foregut cells, hepatoblasts or hepatic progenitor cells. The hepatic cells of the liver organoid can be hepatocytes and/or biliary epithelial cells. The hepatic cells of the liver organoid can be from a single cell type (e.g., definitive endoderm cells, posterior foregut cells, hepatoblasts, hepatocytes or biliary epithelial cells) or from a mixture of cell types (e.g., a mixture of at least two of the following cell types: definitive endoderm cells, posterior foregut cells, hepatoblasts, hepatocytes and/or biliary epithelial cells). During the in vitro cell culture of the liver organoid or even when the liver organoid is placed in vivo, the hepatic cell type(s) can change or differentiate. For example, the hepatic cells of the liver organoid can differentiate (from definitive endoderm, posterior foregut or hepatoblasts to hepatocytes or biliary epithelial cells) during co-culture with mesenchymal and optionally endothelial cells or when placed in vivo. In order to determine if hepatocytes are present in the liver organoids, the expression of cytochrome P450 family 3 subfamily A member 4 (CyP3A4), α fetoprotein (AFP) can be determined by means known in the art. The synthesis/production of albumin, clotting factors and urea, as well as the activity of CyP3A4, can also be monitored to determine if hepatocytes are present in the liver organoid. In order to determine if definitive endoderm or posterior foregut cells are present in the liver organoids, the expression of SOX17, FOXA2, CXCR4, GATA4 or HNF4α can be determined by means known in the art.

The mesenchymal cells of the liver organoid can be, for example, mesenchymal stem/progenitor cells of different origins (bone marrow (including blood), umbilical cord or adipose tissue), adipocyte, muscle cells, hepatic stellate cells, myofibroblasts and/or fibroblasts. The mesenchymal cells of the liver organoid can be from a single cell type (e.g., mesenchymal stem/progenitor cells, adipocyte, muscle cells or fibroblasts) or from a mixture of cell types (e.g., a mixture of at least two of the following cell types: mesenchymal stem/progenitor cells, adipocyte, muscle cells, hepatic stellate cells, myofibroblasts and/or fibroblasts). The type of mesenchymal cells of the liver organoid can differentiate (from mesenchymal stem/progenitor cells to fibroblasts, adipocytes or muscle cells) during co-culture with hepatic and optionally endothelial cells or when placed in vivo. Mesenchymal stem/progenitor cells are known to express, amongst others genes, a smooth-muscle actin (aSMA), fibronectin, CD90 and CD73. In order to determine the location or presence of mesenchymal cells in a liver organoid, it is possible, amongst other things, to determine the expression of genes or proteins specific or associated to the mesenchymal lineage.

The endothelial cells of the liver organoid, when present, can be, for example, endothelial progenitor cells and/or endothelial cells of various origins. The endothelial cells of the liver organoid can be from a single cell type (e.g., endothelial progenitor cells or endothelial cells) or from a mixture of cell types (e.g., a mixture of endothelial progenitor cells and endothelial cells). The type endothelial cells of the liver organoid can differentiate (from endothelial progenitor cells to endothelial cells) during in vitro co-culture with endodermal and mesenchymal cells or when placed in vivo. In some embodiments, the endothelial cells of the liver organoid can organise in a capillary or a capillary-like configuration in which endothelial cells line up the internal surface of a lumen (which can be partial).

As indicated above, the cellular core of the liver organoid is composed of hepatic, mesenchymal and optionally endothelial cells and, in some embodiments, of a extracellular matrix produced and assumed by the cells during culture. The cellular core of the liver organoid is substantially poor in necrotic/apoptotic cells (e.g., it does not have necrotic areas when examined by histology) because nutrients from the medium in which the liver organoids are cultured can diffuse across the cellular core and thus can be delivered to cells within the cellular core and the metabolic waste products of the cells of the cellular core can diffuse out of the liver organoid. The liver organoid itself (prior to encapsulation) does not include (e.g., is free from) exogenous extracellular matrix or synthetic polymeric material. In some embodiments, the hepatic cells can be present on the surface of the cellular core. In another embodiment, the hepatic cells can, in combination with the cells of the cellular core, produce and assemble extracellular matrix material (collagen and fibronectin for example) and, in some embodiment, basal membrane material.

As indicated above, the hepatic cells can cover at least partially the surface of the cellular core of the liver organoid. In the context of the present disclosure, the expression "hepatic cells cover at least partially the surface of the cellular core" indicate that the hepatic cells occupy at least about 10%, 20%, 30% or 40% of the surface of the cellular core. In some embodiments, the hepatic cells substantially cover the surface of the cellular core. In the context of the present disclosure, the expression "hepatic cells substantially cover the surface of the cellular core" indicate that the hepatic cells occupy the majority of the surface of the cellular core, for example, at least about 50%, 60%, 70%, 80%, 90%, 95%, 99% of the surface of the cellular core. In an embodiment, the hepatic cells completely cover the surface of the cellular core (e.g., more than 99% of the surface of the cellular core is covered with hepatic cells).

In an embodiment, the liver organoids of the present disclosure, before encapsulation in the first cross-linked biocompatible polymer, have a higher proportion of mesenchymal (and when present endothelial) cells than hepatocytes and/or biliary epithelial cells than what is observed in the mammalian liver. However, after encapsulation in the first cross-linked biocompatible polymer, the liver organoids of the present disclosure have a higher proportion of hepatic cells when compared to mesenchymal (and when present endothelial) cells. It is known that the mammalian liver is composed of about 90% hepatic cells. As such, in some embodiments of the present disclosure, the proportion of hepatic cells in the liver organoids is lower than about 90%, 85%, 80% or 75% (in comparison to the total number of cells of the liver organoid).

Liver organoids can be made from cells of different origin. In an embodiment, at least one of the hepatic, mesenchymal or endothelial cells are from a mammal, for example a human. In another embodiment, at least two of the hepatic, mesenchymal or endothelial cells are from a mammal, for example a human. In still another embodiment, the hepatic, mesenchymal and endothelial cells are all from a mammal, for example a human. Within the liver organoid, cells from different origin can be combined. For example, the mesenchymal and endothelial cells can be from murine or porcine origin while the hepatic cells can be from human origin. These combinations are not exhaustive and the person skilled in the art will envisage additional combinations that can be suitable in the context of the present disclosure.

The cells of the liver organoid can be derived from different sources. For example, the cells of the liver organoid can be derived from a primary cell culture, an established cell line or a differentiated stem cell. Within the liver organoid, cells from different sources can be combined. For example, the hepatic cells can be from a primary cell culture, the mesenchymal cells can be from an established cell line and the endothelial cell can be from a differentiated cell line. Alternatively, within the liver organoid, cells from the same source (for example differentiated stem cells) can also be combined. In a specific embodiment, the cells of the liver organoid are derived from a single stem cell population which has been differentiated in hepatic, mesenchymal and, optionally, endothelial cells. The stem cell population can be from an embryonic stem cell or an induced pluripotent stem cell. In a specific embodiment, the cells of the liver organoid are derived from a single pluripotent stem cell population which has been differentiated in hepatic, mesenchymal and, optionally, endothelial cells.

The polymer (also referred to as a polymeric matrix) that can be used in the encapsulated liver tissue forms an hydrogel around the liver organoid(s). As known in the art, an hydrogel refers to polymeric chains that are hydrophilic in which water is the dispersion medium. Hydrogels can be obtained from natural or synthetic polymeric networks. In the context of the present disclosure, encapsulation within the hydrogel prevents embedded liver organoids from leaking out of the polymer, thus eliminating or reducing the risk that cells of the liver organoids could give rise to an immune reaction or a tumor within the recipient's body upon implantation. In an embodiment, each liver organoid is encapsulated individually and the encapsulated liver organoids can, in another embodiment, be further included in a polymeric matrix. In still another embodiment, the liver organoids are included in a polymeric matrix so as to encapsulate them.

In the context of the present disclosure, a polymer is considered "biocompatible" when is it does not exhibit toxicity when introduced into a subject (e.g., a human for example). In the context of the present disclosure, it is preferable that the biocompatible polymer does not exhibit toxicity towards the cells of the liver organoid or when placed in vivo in a subject (e.g., a human for example). Hepatotoxicity can be measured, for example, by determining hepatocytes apoptotic death rate (e.g., wherein an increase in apoptosis is indicative of hepatotoxicity), transaminase levels (e.g., wherein an increase in transaminase levels is indicative of hepatotoxicity), ballooning of the hepatocytes (e.g., wherein an increase in ballooning is indicative of hepatotoxicity), microvesicular steatosis in the hepatocytes (e.g., wherein an increase in steatosis is indicative of hepatotoxicity), biliary cells death rate (e.g., wherein an increase in biliary cells death rate is indicative of hepatotoxicity), γ-glutamyl transpeptidase (GGT) levels (e.g., wherein an increase in GGT levels is indicative of hepatotoxicity). Biocompatible polymers include, but are not limited to, carbohydrates (glycosaminoglycan such as hyaluronic acid (HA), chondroitin sulphate, dermatan sulphate, keratan sulphate, heparan sulphate, alginate, chitosan, heparin, agarose, dextran, cellulose, and/or derivatives thereof), proteins (collagen, elastin, fibrin, albumin, poly (amino acid), glycoprotein, antibody and/or derivatives thereof) and/or synthetic polymers (e.g., based on poly (ethylene glycol) (PEG), poly(hydroxyethyl methacrylate) (PHEMA) and/or poly(vinyl alcohol) (PVA)). The biocompatible polymer can be a single polymer or a mixture of different polymers (for example those described in US2012/0142069). Exemplary biocompatible polymers includes, but are not limited to, poly(ethylene) glycol, polylactic acid (PLA), polyglycolic acid (PGA), polycaprolactone (PCL), fibrin, polysaccharidic materials (like chitosan, proteoglycans or glycosaminoglycans (GAGs)), alginate, collagen, thiolated heparin and mixtures thereof. In some embodiments, the biocompatible polymers can be linear, branched and optionally grafted with peptides (e.g., RGD), growth factors, integrins or drugs.

In some embodiments, the polymer is "low-immunogenic polymer" and does not elicit or elicits only a minimal (i.e. not resulting in a degradation, modification or loss of function of the polymer) immune response in the recipient. This low-immunogenic polymer is also capable of masking one or more antigenic determinant of a cell and lowering or even preventing an immune response to the antigenic determinant when such an antigenic determinant is introduced into an allogeneic subject.

The polymer present in the encapsulated liver tissue of the present disclosure are preferably cross-linkable, e.g., capable of being cross-linked. The polymers can be cross-linked thermally, chemically (e.g., by using one or more peptides, such as, VPMS, RGD, etc.) or by the use of pH or light (e.g., photopolymerization, using UV light for example). In some embodiments, cross-linking can be carried out after the liver organoids (encapsulated or not by a polymeric matrix) have been dispersed within the polymeric matrix.

The polymers of the present disclosure can either be totally or partially biodegradable (e.g., susceptible of being hydrolysed by the metabolism of a living organism) or totally or partially resistant to biodegradation (e.g., resistant to hydrolysis when subjected to the metabolism of a living organism). Exemplary biocompatible and biodegradable polymers include, but are not limited to poly(ethylene-glycol)-maelimide (PEG-Mal) 8-arm. Exemplary biocompatible and biodegradation-resistant polymers include, but are not limited to, poly(ethylene-glycol)-vinyl sulfone (PEG-VS).

The encapsulated liver tissue comprises a first biocompatible and cross-linked polymer which at least partially (and in some instances substantially) covers the liver organoid. The first biocompatible polymer is in physical contact with the cells of the liver organoids. In the context of the present disclosure, the expression "liver organoid(s) at least partially covered by the first biocompatible and cross-linked polymer" indicates that the first biocompatible and cross-linked polymer occupies at least about 10%, 20%, 30% or 40% of the surface of the liver organoid. In some embodiments, the first biocompatible and cross-linked polymer substantially covers the surface of the liver organoid(s). In the context of the present disclosure, the expression "liver organoid(s) substantially covered by the first biocompatible and cross-linked polymer" indicates that the first biocompatible and cross-linked polymer occupies the majority of the surface of the liver organoid, for example, at least about 50%, 60%, 70%, 80%, 90%, 95%, 99% of the surface of the organoid. In an embodiment, the first biocompatible and cross-linked polymer completely covers the surface of the liver organoid (e.g., more than 99% of the surface of the liver organoid is covered with the first biocompatible and cross-linked polymer).

In some embodiments, the encapsulated liver tissue can also comprise a second biocompatible and cross-linked polymer which at least partially (and in some instances substantially) covers the first biocompatible and cross-linked polymer. The second biocompatible polymer is in physical contact with the first biocompatible cross-linked and, in embodiments, with the cells of the liver organoid. In the context of the present disclosure, the expression "first biocompatible cross-linked polymer at least partially covered by the second biocompatible and cross-linked polymer" indicates that the second biocompatible and cross-linked polymer occupies at least about 10%, 20%, 30% or 40% of the surface of the first biocompatible and cross-linked first polymer. In some embodiments, the second biocompatible and cross-linked polymer substantially covers the surface of the first biocompatible and cross-linked polymer. In the context of the present disclosure, the expression "first biocompatible and cross-linked polymer substantially covered by the second biocompatible and cross-linked polymer" indicates that the second biocompatible and cross-linked polymer occupies the majority of the surface of the first biocompatible and cross-linked polymer, for example, at least about 50%, 60%, 70%, 80%, 90%, 95%, 99% of the surface of the first biocompatible and cross-linked first polymer. In an embodiment, the second biocompatible and cross-linked polymer completely covers the surface of the first biocompatible and cross-linked polymer (e.g., more than 99% of the surface of the first biocompatible and cross-linked polymer is covered with the second biocompatible and cross-linked polymer). In still another embodiment, the second biocompatible and cross-linked polymer forms a matrix into which liver organoids (which are at least partially covered with the first biocompatible and cross-linked polymer) are interspersed. In such embodiment, the liver organoids (which are at least partially covered with the first biocompatible and cross-linked polymer) can be surrounded by the second biocompatible and cross-linked matrix or can be in physical contact with another liver organoid (which is at least partially covered with the first biocompatible and cross-linked polymer). The encapsulated liver tissue can comprise a further biocompatible and cross-linked polymer to cover the second biocompatible and cross-linked polymer.

The first and second biocompatible and cross-linked polymer can be the same or different. In an embodiment, the first biocompatible and cross-linked polymer is a at least partially (and in some embodiments totally) biodegradable polymer. In another embodiment, the second biocompatible and cross-linked polymer is at least partially (and in some embodiments totally) resistant to biodegradation. In yet another embodiment, the first biocompatible and cross-linked polymer is a biodegradable polymer and the second biocompatible and cross-linked polymer is resistant to biodegradation. In such embodiment, the first biocompatible cross-linked polymer can be more biodegradable (e.g., less resistant to biodegradation) than the second biocompatible cross-linked polymer.

In some embodiments, the first biocompatible and cross-linked polymer comprises a plurality of liver organoids. In such embodiment, the encapsulated liver tissue can comprise at least about 50, 60, 70, 80, 90, 100, 125, 150, 175, 200, 250, 300, 350, 400, 450 or 500 liver organoids per $cm^2$. In still another embodiment, the encapsulated liver tissue can comprise at most about 500, 450, 400, 350, 300, 250, 200, 175, 150, 125, 100, 90, 80, 70, 60 or 50 liver organoids per $cm^2$. In yet another embodiment, the encapsulated liver tissue comprises between about 50, 60, 70, 80, 90, 100, 125, 150, 175, 200, 250, 300, 350, 400 or 450 and about 500, 450, 400, 350, 300, 250, 200, 175, 150, 125, 100, 90, 80, 70 or 60 liver organoids per $cm^2$. In yet another embodiment, the encapsulated liver tissue comprises between about 50 and 500 liver organoids per $cm^2$. In another embodiment, the encapsulated liver tissue comprises at least about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400 or 2500 liver organoids per $cm^3$. In still a further embodiment, the encapsulated liver tissue comprises at most about 2500, 2400, 2300, 2200, 2100, 2000, 1900, 1800, 1700, 1600, 1500, 1400, 1300, 1200, 1100, 1000, 950, 900, 850, 800, 750, 700, 650, 600, 550, 500, 450, 400, 350, 300 or 250 liver organoids per $cm^3$. In still another embodiment, the encapsulated liver tissue comprises between about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300 or 2400 and about 2500, 2400, 2300, 2200, 2100, 2000, 1900, 1800, 1700, 1600, 1500, 1400, 1300, 1200, 1100, 1000, 950, 900, 850, 800, 750, 700, 650, 600, 550, 500, 450, 400, 350 or 300 liver organoids per $cm^3$. In still another embodiment, the encapsulated liver tissue comprises between about 250 and 2500 liver organoids per $cm^3$.

In an embodiment, the encapsulated liver tissue in culture or when implanted in vivo is capable of expressing genes and proteins associated with hepatic, mesenchymal and optionally endothelial cells. In additional embodiment, the encapsulated liver tissue (in vitro or in vivo) is capable of producing albumin, making urea from ammonia, exhibiting CyP3A4 activity and/or metabolizing drugs (known to be metabolized by the liver, such as tacrolimus and/or rifampicin). In some embodiments, the encapsulated liver tissue is capable of producing 1, 2, 3, 4, 5, 6, 7, 8, 9, 10, 11, 12, 13, 14, 15, 16, 17, 18, 19 or 20 mg of albumin per g of liver organoids in the tissue. In another embodiment, the encapsulated liver tissue upon one or more freeze-thaw cycles is capable of expressing genes and proteins associated with hepatic, mesenchymal and optionally endothelial cells, albumin production, of making urea from ammonia, of exhibiting CyP3A4 activity and/or liver-specific metabolism of drugs (such as tacrolimus and/or rifampicin). In some embodiments after freezing, the encapsulated liver tissue is capable of producing 1, 2, 3, 4, 5, 6, 7, 8, 9, 10, 11, 12, 13, 14, 15, 16, 17, 18, 19 or 20 mg of albumin per g of liver organoids in the tissue.

Process for Making Encapsulated Liver Tissue

The process for making the encapsulated liver tissue first requires to make the liver organoid(s) and then encapsulated it (them) (at least partially) in the first biocompatible and cross-linked polymer (and optionally in the second and a further biocompatible cross-linked polymer).

The liver organoid can be made by co-culturing hepatic cells, mesenchymal cells and optionally endothelial cells (all as described above) in conditions necessary to obtain a liver organoid having (i) a cellular core comprising hepatic, mesenchymal and optionally endothelial cells, (ii) a substantially spherical shape and (iii) a relative diameter between about 50 and about 500 µm. In some embodiments, these conditions include culturing the cells in suspension (e.g., ultra-low adherent conditions) so as to promote the formation of the liver organoids.

The hepatic cells to be included in the encapsulated liver tissue can be obtained from different origins (mammals for example) and sources (primary cell culture, cell line, differentiated stem cells). The hepatic cells can be from different types such as definitive endoderm cells, posterior foregut cells, hepatoblasts, hepatocytes and/or biliary epithelial cells. Hepatic cells from a single organoid can be from the same or different origin, from the same or different source and from the same or different type. In an embodiment, definitive endoderm cells are used. In still another embodiment, definitive endoderm cells are obtained from differentiating stem cells (such as pluripotent stem cells). In still another embodiment, the cells derived from definitive endoderm are obtained from differentiating pluripotent stem cells (for example by culturing pluripotent stem cells with Activin A in combination with CHIR99021 and knock-out serum replacement). In an embodiment, cells from the posterior foregut are used. In still another embodiments, the cells from the posterior foregut are obtained from differentiating stem cells (such as pluripotent stem cells). In still another embodiment, the cells from the posterior foregut are obtained from differentiating pluripotent stem cells (for example by culturing pluripotent stem cells with BMP4 in combination with bFGF, with knock-out serum replacement, with or without insulin and/or IWP2 and/or A83-01). In an embodiment, hepatocytes and hepatoblasts are used. In still another embodiments, the hepatocytes and the hepatoblasts are obtained from differentiating stem cells (such as pluripotent stem cells). In still another embodiment, the hepatocytes and hepatoblasts are obtained from differentiating pluripotent stem cells (for example by culturing pluripotent stem cells with BMP4 in combination, bFGF, knock-out serum replacement, with or without insulin and/or CHIR99021, IWP2, A83-01, HGF, oncostatin M and/or dexamethasone). The hepatic cells can be used fresh or cryopreserved prior to the formation of the liver organoids.

The mesenchymal cells to be included in the encapsulated liver tissue can be obtained from different origins (mammals for example) and sources (primary cell culture, cell line, differentiated stem cells). The mesenchymal cells can be from different types such as mesenchymal stem cells, adipocyte, muscle cells or fibroblasts. Mesenchymal cells from a single organoid can be from the same or different origin, from the same or different source and from the same or different type. In an embodiment, mesenchymal stem/progenitor cells are used. In still another embodiment, the mesenchymal stem/progenitor cells are obtained from differentiating a stem cell (such as pluripotent stem cells). In still another embodiment, the mesenchymal stem/progenitor cells are obtained from differentiating pluripotent stem cells (for example by culturing pluripotent stem cells on plastic without coating in DMEM high glucose supplemented with knock-out serum replacement). The mesenchymal cells can be used fresh or cryopreserved prior to the formation of the liver organoids.

When present, the endothelial cells to be included in the encapsulated liver tissue can be obtained from different origins (mammals for example) and sources (primary cell culture, cell line, differentiated stem cells). The endothelial cells can be from different types such as endothelial progenitor cells and endothelial cells. In an embodiment, endothelial progenitor cells are used. Endothelial cells from a single organoid can be from the same or different origin, from the same or different source and from the same or different type. In still another embodiment, the endothelial progenitor cells are obtained from differentiating a stem cell (such as pluripotent stem cells). In still another embodiment, the endothelial progenitor cells are obtained from differentiating pluripotent stem cells (for example by culturing pluripotent stem cells with CHIR99021 and/or Activin A in combination with BMP4, bFGF and/or VEGF). The endothelial cells can be used fresh or cryopreserved prior to the formation of the liver organoids.

In an embodiment, the liver organoid is prepared from a single population of pluripotent stem cells. The pluripotent stem cells can be induced using methods known in the art such as viral transduction (for example by using Sendai virus system) or using a synthetic mRNA approach. The population of pluripotent stem cells can be obtained from one or more colonies of induced pluripotent stem cells (iPSCs). In the embodiment in which the liver organoid is prepared from the same population of pluripotent stem cells, the population of iPSCs is divided in at least two (and in some embodiments at least three) subpopulations each submitted to different culture conditions to generate hepatic and mesenchymal (and, in some embodiments, endothelial cells).

Once each of the different cells are obtained, they are combined and cultured in suspension to generate the liver organoid. To control the size of the liver organoids, it is possible to culture the cells in ultra-low-adherent conditions (e.g., in suspension) using micro-cavities having a diameter between 100 to 1 000 µm. In some embodiments, the micro-cavities have a diameter and depth per $cm^2$ of about 500 µm. In some embodiments, once the original liver organoids are formed, they can be cultured (for expansion) in suspension in a bioreactor. To promote the differentiation of the endoderm-derived cells into hepatocytes and/or biliary epithelial cells, the liver organoids can be cultured in the presence of knock-out serum replacement, and/or insulin, EGF, HGF, VEGF, bFGF, oncostatin M and/or dexamethasone. In an embodiment, the hepatic and mesenchymal are combined at a ratio, prior to culture, of 1 endodermal cells to 0.1-0.7 mesenchymal cells. In still another embodiment, when the endothelial cells are present, they are combined with endodermal cells at a ratio, prior to culture of 1 endodermal cell for of 0.2-1 endothelial cell. In still another embodiment, the ratio between the hepatic, mesenchymal and endothelial cells is 1:0.2:0.7 prior to culture. It is understood that, during culture, the ratio between the different cells may change since some are going to preferentially proliferate while other will preferentially differentiate. It is also understood that other ratios can be used to obtain the liver organoids as described herein. During the process of making the liver organoid, no physical scaffold or exogenous matrix material (other than the tissue culture vessel) is required.

The liver organoids can be used directly to make the encapsulated liver tissue. In an embodiment, the liver organoids can be cryopreserved prior to their introduction in the encapsulated liver tissue.

The polymer that can be used in the encapsulated liver tissue forms an hydrogel around the liver organoid(s). As known in the art, an hydrogel refers to polymeric chains that are hydrophilic in which water is the dispersion medium. Hydrogels can be obtained from natural or synthetic polymeric networks. In the context of the present disclosure, encapsulation within the hydrogel prevents embedded liver organoids from leaking out of the polymer, thus eliminating or reducing the risk that cells of the liver organoids could give rise to an immune reaction or a tumor within the recipient's body upon implantation.

In the context of the present disclosure, a polymer is considered "biocompatible" when is it does not exhibit toxicity towards the cells of the liver organoids or when introduced into a subject (e.g., a human for example). In the context of the present disclosure, it is preferable that the biocompatible polymer does not exhibit toxicity towards the cells of liver organoid when placed in vivo in a subject (e.g., a human for example). Hepatotoxicity can be measured, for example, by determining hepatocytes apoptotic death rate (e.g., wherein an increase in apoptosis is indicative of hepatotoxicity), transaminase levels (e.g., wherein an increase in transaminase levels is indicative of hepatotoxicity), ballooning of the hepatocytes (e.g., wherein an increase in ballooning is indicative of hepatotoxicity), microvesicular steatosis in the hepatocytes (e.g., wherein an increase in steatosis is indicative of hepatotoxicity), biliary cells death rate (e.g., wherein an increase in biliary cells death rate is indicative of hepatotoxicity), γ-glutamyl transpeptidase (GGT) levels (e.g., wherein an increase in GGT levels is indicative of hepatotoxicity). Biocompatible polymers include, but are not limited to, carbohydrates (glycosaminoglycan such as hyaluronic acid (HA), chondroitin sulphate, dermatan sulphate, keratan sulphate, heparan sulphate, alginate, chitosan, heparin, agarose, dextran, cellulose, and/or derivatives thereof), proteins (collagen, elastin, fibrin, albumin, poly (amino acid), glycoprotein, antibody and/or derivatives thereof) and/or synthetic polymers (e.g., based on poly(ethylene glycol) (PEG), poly(hydroxyethyl methacrylate) (PHEMA) and/or poly(vinyl alcohol) (PVA)) .The biocompatible polymer can be a single polymer or a mixture of polymers (for example those described in US2012/01420069). Exemplary biocompatible polymers includes, but are not limited to, poly(ethylene) glycol, polylactic acid (PLA), polyglycolic acid (PGA), polycaprolactone (PCL), fibrin, polysaccharidic materials (like chitosan, proteoglycans or glycosaminoglycans (GAGs)), alginate, collagen, thiolated heparin and mixtures thereof. In some embodiments, the biocompatible polymers can be linear, branched and optionally grafted with peptides (e.g., RGD), growth factors, integrins or drugs.

In some embodiments, the polymer is "low-immunogenic polymer" and does not elicit or elicits only a minimal immune response in the recipient. This low-immunogenic polymer is also capable of masking one or more antigenic determinant of a cell and lowering or even preventing an immune response to the antigenic determinant when such an antigenic determinant is introduced into an allogeneic subject.

The polymer present in the encapsulated liver tissue of the present disclosure are preferably cross-linkable, e.g., capable of being cross-linked. The polymers can be cross-linked thermally, chemically (e.g., by using one or more peptides, such as, VPMS, RGD, etc.) or by the use of pH or light (e.g., photopolymerization, using UV light for example).

The polymers of the present disclosure can either be biodegradable (e.g., susceptible of being hydrolysed by the metabolism of a living organism) or be totally or partially resistant to biodegradation (e.g., resistant to hydrolysis when subjected to the metabolism of a living organism). Exemplary biocompatible and biodegradable polymers include, but are not limited to poly(ethylene-glycol)-maelimide (PEG-Mal) 8-arm. Exemplary biocompatible and biodegradation-resistant polymers include, but are not limited to, poly(ethylene-glycol)-vinyl sulfone (PEG-VS).

Once the liver organoids are obtained, they are contacted with the first biocompatible and cross-linkable polymer to at least partially (and in some embodiments substantially) cover the liver organoids. The polymer can be used at different concentrations. In an embodiment, the concentration of the polymer, upon contacting the liver organoids, is between about 1% and 15% (weight/volume). In an embodiment, the concentration of the polymer, upon contacting the liver organoid, is at least about 1%, 2%, 3%, 4%, 5%, 6%, 7%, 8%, 9%, 10%, 11%, 12%, 13% or 14%. In yet another embodiment, the concentration of the polymer, upon contacting the liver organoids, is equal to or lower than about 15%, 14%, 13%, 12%, 11%, 10%, 9%, 8%, 7%, 6%, 5%, 4%, 3% or 2%. Once the liver organoids have been contacted with the first polymer, the latter is cross-linked (either thermally, chemically or by using pH or light). Cross-linking the first biocompatible polymer is achieved by creating additional bonds (and in some embodiments additional covalent bonds) between different molecules of the polymer and/or within the same molecule of the polymer. In some embodiments, the cross-linking of the first biocompatible polymer will create additional bonds (and in some embodiments additional covalent bonds) between the polymeric molecules and the surface of the liver organoid. In some embodiments, the first polymer is at least partially biodegradable.

In some embodiments, the liver organoids that have been covered or encapsulated (at least partially) with the first biocompatible cross-linked polymer can be contacted with a second biocompatible cross-linkable polymer to at least partially (and in some embodiments substantially) cover the encapsulated liver tissue. Once the encapsulated liver organoids have been contacted with the second polymer, the latter is cross-linked (either thermally, chemically or by using pH or light). Cross-linking the second biocompatible polymer is achieved by creating additional bonds (and in some embodiments additional covalent bonds) between different molecules of the polymer and/or within the same molecule of the polymer. In some embodiments, the cross-linking of the second biocompatible polymer will create additional bonds (and in some embodiments additional covalent bonds) between the polymeric molecules and the first biocompatible and cross-linked polymer and, in some embodiments, the surface of the liver organoid. In some embodiments, the second polymer is, at least partially, resistant to biodegradation.

In some embodiments, the process also includes a step of contacting the encapsulated liver organoids (at least partially covered by the first/second biocompatible cross-linked polymer) with a further biocompatible and cross-linkable polymer to cover the encapsulated liver organoid. Once the liver organoids have been contacted with the further polymer, the latter is cross-linked (either thermally, chemically or by using pH or light). Cross-linking of the further biocompatible polymer is achieved by creating additional bonds (and in some embodiments additional covalent bonds) between different molecules of the polymer and/or within the same molecule of the polymer. In some embodiments, the cross-linking of the further biocompatible polymer will create additional bonds (and in some embodiments additional covalent bonds) between the polymeric molecules and the second biocompatible and cross-linked polymer and, in some embodiments, the first biocompatible and cross-linked polymer and/or the surface of the liver organoids.

Figure 4A:
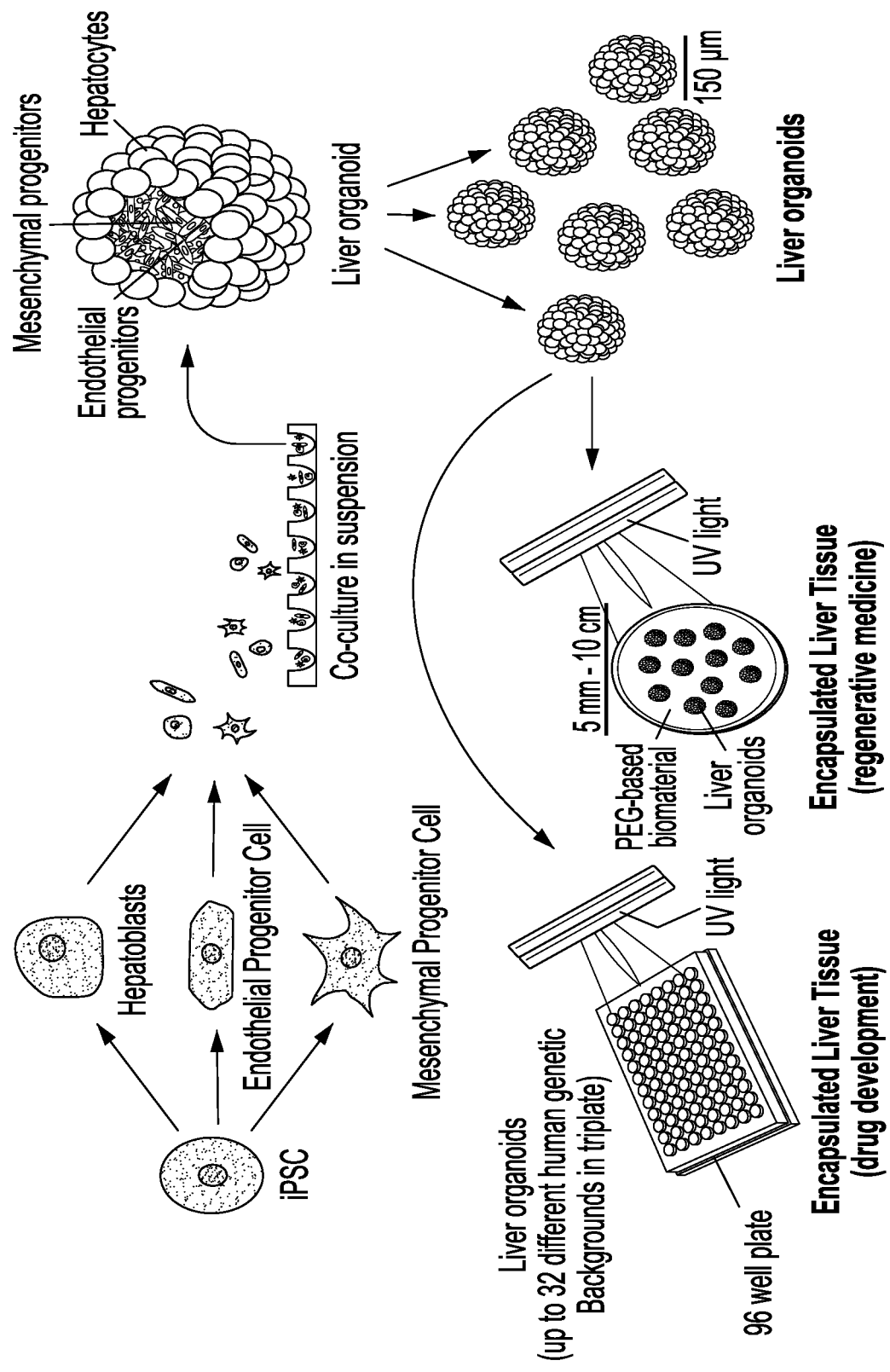
FIGS. 4A to 4Q illustrate embodiments of the encapsulated liver tissue. (A) Embodiment of a process for encapsulating the liver organoids and making the encapsulated liver tissue. (B) Macroscopic aspect of the PEG-encapsulated liver organoids (encapsulated liver tissue) and manipulation of the encapsulated liver tissue (top row: encapsulated liver tissue ready for transplantation in mice; bottom-left and center: encapsulated liver tissue in a 96-well format; bottom-right: microscopic aspect of liver organoids within the biomaterial, scale bar 1000 μM). (C) Representative immunofluorescence of cellular viability of three different encapsulated liver tissues (live/dead assay). Scale bar 1 000 μM for the 3 top left panels, 200 μM for top-right panel and the three bottom-right panels, and 100 μM for the bottom-left panel. (D) Histological images of two representative encapsulated liver tissue. Scale bar 50 μm. (E) Comparison of CyP3A4 activity, urea production, α-fetal protein (AFP) section and albumin secretion in primary hepatocytes (PHH), cells of the HepG2 cell line (HepG2), iPSCs, iPSC-derived hepatocytes (iHeps, after 28 days of differentiation) and encapsulated liver organoids (ELT). For CyP3A4 activity, results are shown as activity (expressed as RLU, or relative light units per $10^6$ hepatic cells, ***=p<0.001) in function of cell/organoid type. For urea production, results are shown as urea produced (μg/24 h/$10^6$ cells) in function of cell/organoid type. For AFP secretion, results are shown as the amount of AFP secreted by the encapsulated liver tissue over time in culture (measured as ng/$10^6$ cells/24 h, *=p<0.05). For albumin secretion, results are shown as the amount of albumin produced (ng/24 h/1×$10^6$ cells) in function of time in culture (**=p<0.01). (F) Ammonia metabolism (left panel) and urea production (right panel) by the encapsulated liver tissue in vitro. For ammonia metabolism, results are shown as the concentration of ammonia (mmol/L) in function of time (h) in culture (*=p<0.05). For urea production, results are shown as urea produced (μg/24 h/$10^6$ cells, *=p<0.001) in the absence (−) or presence (+) of ammonia (1 mM). (G) Tacrolimus metabolism by the encapsulated liver tissue in vitro. Results are shown as tacrolimus concentration (ng/mL, *=p<0.001) in function of incubation time (h) in the presence (■) or absence (●) of rifampicin. (H) Albumin secretion (left panel) and CyP3A4 activity (right panel) of the encapsulated liver tissue before freezing, after thawing and 7 days (d7) after thawing. For albumin secretion, results are shown as the amount of albumin produced (ng/24 h/1×$10^6$ cells) in function of the condition tested. For CyP3A4 activity, results are shown as activity (RLU/$10^6$ cells) in function of the condition tested. (I) Macroscopic view obtained during the intra-abdominal implantation of the encapsulated liver tissue. (J) Macroscopic view obtained 1 week (left panels) or 4 weeks (right panel) after intra-abdominal implantation of encapsulated liver organoids (picture of the explanted ELT without any visible adherence or inflammation). (K) Macroscopic (left panel) and microscopic views (hematoxylin and eosin staining, middle and right panels) of non-encapsulated iPSCs showing the formation of teratomas in immunosuppressed mice. (L) Representative macroscopic views of encapsulated iPSCs 8 weeks after implantation in mice showing the lack of formation of teratomas in the animals. (M) CD25, HLA-DR, proliferation (Carboxyfluorescein succinimidyl ester, CFSE) Interferon-γ (IFNg), CD3+IFNg and CD69 expression as measured by flow cytometry of cells having been submitted to a mixed lymphocyte reaction (MLR). Conditions of the MLR are provided on the left side of the figure. (N) Interferon-γ (IFNg) production in a mixed lymphocyte reactions in the presence of allogeneic PBMC only (Effector PBMC only), of the encapsulating biomaterial alone (Biomaterial), mature dendritic cells (mDC), encapsulated mDCs, liver organoids and encapsulated liver organoids (ELT). Results are shown as the amount of IFNg (pg/mL) in function of the conditions tested. (O) Encapsulation of cells and organoids prevents allogeneic T cell proliferation (MLR assay). Liver organoids elicited only minimal T cell proliferation. No T cell activation was seen upon encapsulation of allogeneic liver organoids, PBMC or even mature dendritic cells. Abbreviations: ctrl=no cells; +gel=encapsulation within the biomaterial; allo DC=allogeneic mature dendritic cells; PBMC=allogeneic peripheral blood mononuclear cells; liver org=non-encapsulated iPSC-derived liver organoids; liver org+gel=ELT. Results are shown as the percentage of proliferative cells or cells positive for CD25, HLA-DR, CD69 or IFNg (measured using flow cytometry). (P) Survival (left panel) et weight gain or loss (right panel) in sham-treated animals or animals treated with the encapsulated liver tissue (ELT). For survival, results are shown as the percentage of survival 30 days following induction of liver failure in sham treated (dashed line) and ELT-treated (solid line) animals. For weight gain or loss, results are shown as the percentage of the animal's weight at day 7 when compared to the animal's weight at day 0 of liver failure for sham-treated (■) and ELT-treated (●) animals. p=0.0095. (Q) Schematic representation double PEG encapsulation (top) and microscopic view of the double PEG encapsulated follicles (scale bar 500 μM, ND: non-degradable, D: degradable).

The process can be designed to provide a plurality of monodispersed liver organoids within the first biocompatible and crossed-linked polymer, as shown in FIG. 4A. In the embodiment shown in FIG. 4A, hepatoblasts, endothelial progenitor cells and mesenchymal progenitor cells are obtained from differentiating a single iPSC. The cells are mixed and co-cultured in suspension to form the liver organoid. In the embodiment of the liver organoid shown on FIG. 4A, the hepatoblasts have differentiated into hepatocytes which substantially cover a cellular core formed by mesenchymal and endothelial progenitor cells (prior to the introduction of the liver organoids in the encapsulated liver tissue). The embodiment of the liver organoid shown on FIG. 4A is substantially spherical in shape and has a relative diameter of about 150 µM. The liver organoids are then encapsulated, using a cross-linking agent (UV light shown in FIG. 4A), in a first compatible and cross-linkable matrix. The encapsulated liver tissue can be used as transplantable liver tissue (having for example, a size between 5 mm and 10 cm) in regenerative medicine. Alternatively, the liver organoids can be designed to a multiwell plate and used in drug development to determine metabolism or hepatotoxicity of screened compounds.

The process can be designed to provide a plurality of liver organoids individually covered (at least partially) with the first biocompatible and cross-linked polymer which are then incorporated in a matrix made of the second biocompatible and cross-linked polymer. In such embodiment, the plurality of liver organoids individually covered (at least partially) with the first biocompatible and cross-linked polymer are first formed and then contacted with the second biocompatible and cross-linkable polymer to be cross-linked.

The process can also be designed to provide a plurality of individual (e.g., mono-dispersed) liver organoids which are covered by the first and, optionally, the second compatible and cross-linked polymer. In such embodiment, the encapsulated liver tissue can comprise at least about 50, 60, 70, 80, 90, 100, 125, 150, 175, 200, 250, 300, 350, 400, 450 or 500 liver organoids per cm². In still another embodiment, the encapsulated liver tissue can comprise at most about 500, 450, 400, 350, 300, 250, 200, 175, 150, 125, 100, 90, 80, 70, 60 or 50 liver organoids per cm². In yet another embodiment, the encapsulated liver tissue comprises between about 50, 60, 70, 80, 90, 100, 125, 150, 175, 200, 250, 300, 350, 400 or 450 and about 500, 450, 400, 350, 300, 250, 200, 175, 150, 125, 100, 90, 80, 70 or 60 liver organoids per cm². In yet another embodiment, the encapsulated liver tissue comprises between about 50 and 500 liver organoids per cm². In another embodiment, the encapsulated liver tissue comprises at least about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400 or 2500 liver organoids per cm³. In still a further embodiment, the encapsulated liver tissue comprises at most about 2500, 2400, 2300, 2200, 2100, 2000, 1900, 1800, 1700, 1600, 1500, 1400, 1300, 1200, 1100, 1000, 950, 900, 850, 800, 750, 700, 650, 600, 550, 500, 450, 400, 350, 300 or 250 liver organoids per cm³. In still another embodiment, the encapsulated liver tissue comprises between about 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300 or 2400 and about 2500, 2400, 2300, 2200, 2100, 2000, 1900, 1800, 1700, 1600, 1500, 1400, 1300, 1200, 1100, 1000, 950, 900, 850, 800, 750, 700, 650, 600, 550, 500, 450, 400, 350 or 300 liver organoids per cm³. In still another embodiment, the encapsulated liver tissue comprises between about 250 and 2500 liver organoids per cm³.

In an embodiment, the encapsulated liver tissue can be directly used in the therapeutic and screening methods described herein or can be cryopreserved to increase its storage time.

Therapeutic Use of the Encapsulated Liver Tissue

The encapsulated liver tissue described herein can be used as a medicine. Because it exhibits some of the biological functions of the liver and thus can be used in vivo or ex vivo to restore or improve liver functions in a subject in need thereof. Liver function can be assessed, for example, by determining the synthesis of albumin and clotting factors (e.g., fibrinogen, prothrombin, factors V, VII, VIII, IX, X, XI, XIII, as well as protein C, protein S and antithrombin), whereas an increase in the synthesis of albumin and/or clotting factors is indicative of restored or improved liver function. Liver function can also be assessed by measuring the International Normalized Ratio or INR (e.g., a decrease in INR is indicative of a restored or improved liver function). Liver function can also be assessed by measuring the detoxification of ammonia to urea (e.g., a decrease in the level of ammonia and/or an increase in the level of urea is indicative of restored or improved liver function).

The encapsulated liver tissue has to be in contact with a biological fluid of the subject intended to be treated. In such embodiment, the encapsulated liver releases synthetized proteins and metabolites (albumin, clotting factors and/or urea) needed by the subject into the biological fluid and can even absorb toxic substances to be metabolized (ammonia, unconjugated bilirubin, cholesterol, tyrosine, etc.) from the biological fluid. The encapsulated liver tissue can be used to restore lacking/reduced enzymatic functions in inborn errors of liver metabolism.

In order to restore or improve liver functions, the encapsulated liver tissue can be grafted in vivo in the subject having reduced, little to no liver functions. As such, the encapsulated liver tissue can be, for example, implanted in the peritoneal cavity in connection with peritoneal fluids. Alternatively, the encapsulated liver tissue can be grafted on the recipient's liver, in connection with liver fluids. In yet another example, the encapsulated liver tissue can be grafted subcutaneously or intra-muscularly, in connection with lymphatic fluids or blood.

Alternative, in order to restore or improve liver functions, the encapsulated liver tissue can be used as the cellular component of an ex vivo detoxifying device (e.g., an extracorporeal device). In such embodiment, the blood and/or the peritoneal fluid of the treated subject is contacted ex vivo with the encapsulated liver tissue for providing proteins and metabolites (albumin, clotting factors and/or urea) an adsorb or metabolize potentially toxic substances (ammonia, unconjugated bilirubin, cholesterol, tyrosine, etc.).

The encapsulated liver tissue can be used with various subjects, including mammals and especially humans, who would benefit from restoring or improving liver functions. The cells of the encapsulated liver tissue can be autologous, allogeneic or xenogeneic to the subject intended to be treated. However, because the encapsulated liver tissue can be designed in order to prevent physical contact with the cells (especially the immune cells) of the intended recipient, there is no need to use autologous cells or immunosuppressive drugs to prevent immunological recognition and reaction by the intended recipient. This can be done, for example, by using an encapsulated liver tissue comprising only one biocompatible and cross-linked polymer or both a first and a second biocompatible and cross-linked polymer and/or using a low-immunogenic polymer.

In some embodiments, the encapsulated liver tissue can be designed to be manipulated and introduced into the subject by surgery, for example using a laparoscopic procedure. In addition, because the liver tissue is encapsulated in a biocompatible (and in some embodiments, low-immunogenic) polymer, it is possible to remove the encapsulated liver tissue from the subject once the liver function has been restored or the encapsulated liver tissue can no longer improve liver function.

The encapsulated liver tissue can be used to treat liver failure. Liver failure occurs when large parts of the liver become damaged beyond repair and the liver is no longer able to function. Early symptoms of liver failure include nausea, loss of appetite, fatigue and diarrhea. As the condition progresses, the following symptoms can also be observed jaundice, bleeding, swollen abdomen, mental disorientation or confusion (known as hepatic encephalopathy), sleepiness as well as coma. Liver failure can be acute, chronic or acute-on-chronic. The most common causes of chronic liver failure are non-alcoholic steatohepatitis, hepatitis B, hepatitis C, long-term alcohol consumption, cirrhosis, hemochromatosis and malnutrition. In chronic liver failure, liver cell transplantation is most often practiced via the portal circulation. However, in the case of chronic liver failure secondary to cirrhosis, the disappearance of hepatic sinusoidal fenestrations (capillarization) could prevent the injected cells injected through the portal circulation to reach the liver parenchyma and implant in the liver lobules. This could hamper the maturation and function of the transplanted cells and entail complications such as sinusoidal and portal thrombosis. Since it does not require intraportal injection or immunosuppression, the encapsulated liver tissue described herein would allow treating hundreds of thousands of patients with cirrhosis and chronic (or acute-on-chronic) liver failure, even those not eligible for transplant, preventing or reducing severe complications (hepatic encephalopathy, coagulopathy, etc.) and improving survival.

The encapsulated liver tissue described herein can also be used for treating acute liver failure. The most common causes of acute liver failure are reactions to or overdoses of prescription and herbal medicines, viral infections (including hepatitis A, B, and C), as well as ingestion of poisonous wild mushrooms, autoimmune hepatitis or Wilson disease. Acute liver failure can occur rapidly, sometimes in less than 48 hours, and is thus difficult to prevent. Furthermore in acute liver failure, liver functions are so compromised subjects need to be transplanted with fully mature and functional hepatic cells. In some embodiments, the encapsulated liver tissue can be used to treat or alleviate the symptoms of acute liver failure. The encapsulated liver tissue is either grafted in the subject in need thereof or used as an external (ex vivo) detoxifying device to treat the blood of the subject in need thereof (extracorporeal liver support, bioartificial liver device or liver dialysis). Depending on the number of liver organoids in the encapsulated liver tissue and the severity of the conditions, one or more than one encapsulated liver tissue can be used to treat the subject. The encapsulated liver tissue(s) can be used simultaneously or in sequence. When the encapsulated liver tissue is used to treat or alleviate the symptoms of liver failure, cells allogeneic to the subject to be treated can be used.

The encapsulated liver tissue can also be used to treat or alleviate the symptoms of monogenic inborn error of liver metabolism (e.g., Criggler-Najjar syndrome, familial hypercholesterolemia, urea cycle disorders such as N-acetylglutamate synthase deficiency, carbamoyl phosphate synthase deficiency, ornithine transcarbamylase deficiency, citrullinemia, argininosuccinate lyase deficiency, arginase deficiency, hereditary tyrosinemia type I, etc.). In this embodiment, the encapsulated liver tissue provides the lacking metabolic function, reducing symptoms, preventing or reducing complications and/or reducing or eliminating the need for life-long treatments or diets.

The encapsulated liver tissue can be designed as an implantable product (for example a encapsulated liver tissue sheet) to treat acute and chronic liver failure without the need for immunosuppression. In such embodiment, the implantable tissue sheet comprises about thousands liver organoids per $cm^2$. In some embodiments, the encapsulated liver tissue sheet can be positioned within a container (such as, for example a custom-made, permeable bag) to ease manipulation and fixation to the desired site of implantation. In further embodiments, in order to be manipulated easily, the implantable tissue sheet can be at least of 1 mm-thick and, in some additional embodiments, at least 5 mm to 10 cm-wide. The encapsulated liver tissue can be made to any shape or size required and can be trimmed or cut during implementation.

Hepatic Metabolism and Hepatotoxicity Screening Methods and Kits

Since the encapsulated liver tissue described herein retain at least some hepatic function it can be used as an in vitro model to determine how an agent (such as a potential drug) is metabolized by the liver to rationalize drug discovery and development. It can also be used to determine if an agent exhibits hepatotoxicity. When administered to the general circulation, the vast majority of (suspected) therapeutic agents (approved or in development) are metabolized in some way or another by the cells of the liver. In some embodiments, the encapsulated liver tissue described herein can be used to determine the hepatotoxicity (e.g., drug-induced liver toxicity), if any, of an agent (such as a putative therapeutic agent). Drugs (approved and investigational) are an important cause of liver injury. More than 900 drugs, toxins, and herbs have been reported to cause liver injury, and drugs account for 20-40% of all instances of fulminant hepatic failure. Approximately 75% of the idiosyncratic drug reactions result in liver transplantation or death. Drug-induced hepatic injury is the most common reason cited for withdrawal of an approved drug. Determining early the hepatotoxicity profile of an agent (such as a drug) can be useful to rationalize drug discovery and development.

The encapsulated liver tissue described herein does exhibit at least some liver function and can thus be used in vitro to determine the hepatic metabolism and/or the hepatotoxicity of an agent (such as a chemical agent, a biological agent, a natural drug product or mixture). The method can be used to determine the hepatic metabolism of a single agent or a combination of agents.

In order to do so, the agent or the combination of agents to be tested is/are placed in contact with the encapsulated liver tissue so as to provide a test mixture under conditions sufficient to allow an effect of the agent on at least one (and in some embodiments, two or three) cell types of the at least one liver organoid of the encapsulated liver tissue. The test mixture comprises the agent and the encapsulated liver tissue. Then, at least one agent-related hepatic metabolite of the agent is determined in at least one (and in some embodiments, at least two or three) cell types of the at least one liver organoids of the encapsulated liver tissue or in the test mixture. As used in the context of the present disclosure, the expression "agent-related metabolite" refers to a metabolite which can be formed by hydrolyzing the agent that is being tested.

Alternatively or in combination, at least one hepatic parameter is determined in at least one (and in some embodiments, at least two or three) cell types of the at least one liver organoids of the encapsulated tissue or in the test mixture. Hepatic parameters which can be determined include, but are not limited to albumin production, urea production, ATP production, glutathione production, cytochrome P450 (CYP) metabolic activity, expression of liver-specific genes or proteins (e.g., a CYP enzyme (CyP2C9, CyP3A4, CyP1A1, CyP1A2, CyP2B6 and/or CyP2D6), responses to hepatotoxins, cellular death (e.g. by measuring lactate dehydrogenase or transaminases in the test mixture), cellular apoptosis, cellular necrosis, cellular metabolic activity (e.g. live/dead assay, caspase 3/7 assay, MTT assay or WST-1 based tests), mitochondrial function, and/or bile acid production. Once the at least one (or the plurality of) hepatic parameter has been obtained, it is compared to a corresponding control hepatic parameter. In an embodiment, the control hepatic parameter can be obtained in the absence of the screened agent (or the combination of screened agents) or in the presence of the vehicle for dissolving the screened agent (of the combination of screened agents). The determination step can be conducted on all or some of the cells of the encapsulated liver tissue. In an embodiment, the determination step is conducted on hepatocytes and/or biliary epithelial cells of the encapsulated liver tissue.

The method also includes a comparison to determine if the agent is metabolized by the liver organoids of the encapsulated liver tissue and/or if the agent exhibits hepatotoxicity towards the cells of the liver organoids of the encapsulated liver tissue. In order to do so, a comparison is made between the measured agent-related hepatic metabolite and a control agent-related hepatic metabolite. For example, the control agent-related metabolite can be the agent itself in an intact (e.g., unhydrolyzed) form. When it is determined that an agent-related metabolite which differ from the control agent-related metabolite is present, then it is determined how the agent is metabolized by the hepatic cells. A comparison can also be made between the measured hepatic parameter and a control hepatic parameter. For example, the control hepatic parameter can be obtained in the absence of the agent. When it is determined that an hepatic parameter differs from the control hepatic parameter, then it is determined if the agent exhibits hepatotoxicity.

In an embodiment, the method is used to determine if the screened agent (or the combination of screened agents) exhibits hepatotoxicity. In such embodiment, it is determined if contacting the screened agent (or the combination of screened agents) induces toxicity in at least one cell (for example an hepatocyte or a biliary epithelial cells) of the liver organoid of the encapsulated liver tissue. Toxicity can be measured, for example by determining cell death (e.g. by measuring lactate dehydrogenase or transaminases in the test mixture), cell metabolic viability (e.g. live/dead assay, caspase 3/7 assay, MTT assay or WST-1 based tests), mitochondrial function (e.g., a reduction of mitochondrial function is indicative with hepatotoxicity), modulation in the activity of one or more enzymes (such as, for example, CYP2E1) in the cytochrome P450 system (e.g., an increase in the activity of the enzyme(s) of the cytochrome P450 system is indicative of hepatotoxicity) and/or modulation in the production of bile acids (e.g., an increase in bile acid productions is indicative of hepatotoxicity). The method can include comparing the toxicity results of the screened agent with a control agent (either known not to induce hepatotoxicity or known to induce hepatotoxicity).

The method can also include contacting the screened agent (or the plurality of screened agents) against encapsulated liver tissues obtained with liver organoids having different metabolic activity. For example, liver organoids can be made using cells from different origins and sources in order to perform specific metabolic functions at different levels (thus representing variations found among individuals in the general population). For example, the obtained encapsulated liver tissues with different metabolic activity can be generated in different wells of a single plate, in order to allow testing the screened agent comparatively on each and all of them. In an embodiment, liver organoids can be derived from different genders, races and/or genotypes. The screened agent could be tested against these different genders, races and/or genotypes to determine differences in metabolism or if hepatotoxicity is present in all or only some genders, races and/or genotypes. In an embodiment, the mesenchymal and/or endothelial components of the liver organoids can be similar between the plurality of liver organoids but the hepatocytes and biliary epithelial cells are from different genders, races and/or genotypes. As an example, each different encapsulated liver tissue can be located in a different well (in multiple repetitions if necessary) and the same screened agent can be contacted with each different encapsulated liver tissue.

In some embodiments, the encapsulated liver tissue used in the screening method does not include a second or a further biocompatible cross-linked polymer and instead consists essentially of the liver organoids and the first biocompatible cross-linked polymer as described herein.

The screening method can use liver organoids which have been encapsulated individually or liver organoids which have been encapsulated in a matrix containing more than one liver organoids. In the latter, the encapsulated liver tissue can be located at the bottom of a well making it very convenient to add the screened agent and washing the encapsulated liver tissue prior to the determining step.

The present disclosure also provides a kit for determining hepatic metabolism or hepatotoxicity. The kit comprises the encapsulated liver tissue of described herein and instructions for performing the method described. In some embodiments, the kit further comprises a tissue culture support which can optionally comprises at least one well. In additional embodiments, the encapsulated liver tissue can be located at the bottom of the at least one well and, if necessary, attached (covalently or not) to the surface of the well. The kit can also comprise reagents to perform the hepatic metabolism or hepatotoxicity measurements (e.g., live/dead assay, caspase 3/7 assay, MTT assay, WST-1 assay, and/or LDH measurement for example).

The present invention will be more readily understood by referring to the following examples which are given to illustrate the invention rather than to limit its scope.

EXAMPLE I

Preparation of Liver Organoids

Peripheral blood mononuclear cells (PBMC) isolation. Blood was collected directly into BD Vacutainer® CPT™ tube with sodium heparin 8 mL. The BD Vacutainer® CPT™ tubes were stored at room temperature, but no more than 4 hours (h), if they were not processed immediately. The BD Vacutainer® CPT™ tubes were centrifuged at 1 800 g (2 800 rpm) at room temperature for 20 minutes (min). After centrifugation, using a 5 mL pipette, the plasma was gently pipetted up and down against the gel plug to dislodge cells that may have stuck to the top of the gel. The cell suspension was transferred to a 50 mL Falcon™ tube, pooling the cells from each tube if necessary. Serum-free medium, StemPro-34®, was added to a total volume of 40 mL. A 10 µL aliquot of the suspension was obtained for counting (hemacytometer or automated cell counter) and for determining cell viability (using the Trypan Blue™ exclusion method). The cell suspension was centrifuged at 250 g (1 200 rpm) for 7 min at room temperature. The centrifuged cells were either suspended at a concentration of $5 \times 10^6$ viable cells/mL in complete StemPro-34™ medium and optionally cryopreserved.

PBMCs reprogramming. Four days prior to reprogramming, the fresh or thawed PBMCs were resuspended in complete StemPro34™ (cStemPro-34®) medium supplemented with cytokines (SCF, FLT3, IL3, IL6) to $5 \times 10^5$ cells/mL, seeded and incubated at 37° C./5% $CO_2$. On the day the PBMCs were reprogrammed, the cells were counted and transduced with Sendai virus CytoTune 2.0™ (according to the manufacturer's instructions). More specifically, cells were counted and the volume of each virus needed to reach the target multiplicity of infection (MOI) and the titer information on the certificate of authenticity (CoA) was determined as follows:

Vol virus (µl)=MOI (cell infectious units or CIU/cell)×$n°$ of cells/titer of virus (CIU7 mL)×$10^{-3}$ (µl/mL)

The cells were harvested and seeded in 6-well plates with 2,5-$5 \times 10^5$ cells/well for transduction. The calculated volumes of each of the 3 CytoTune 2.0™ Sendai tubes were added to 1 mL of cStemPro34™ medium pre-warmed to 37° C. The mixture was gently pipetted up and down. The edges of the plate were sealed with Parafilm™ and centrifuged at 2 250 rpm for 90 min at room temperature. An additional 1 mL of cStemPro34™ medium was added to each well and cells were incubated overnight. The next day, the cells and the medium were removed from the culture plate and transferred to a 15 mL tube. The cells were gently rinsed with 1 mL of cStemPro®-34 medium to ensure most of the cells were harvested. The cell suspension was centrifuged at 1 200 rpm for 10 min. The supernatant was discarded and the cells were resuspended in 0.5 mL of cStemPro34™ medium per well of a 6-well plate. The cells were cultured at 37° C./5% $CO_2$ for two days. Three days after the reprogramming, the cells were placed on vitronectin or laminin-coated culture dishes, 10 000 and 50 000 live cells per dish StemPro®-34 medium without the cytokines. Seven days after reprogramming, the cells were transitioned to an iPSC medium (Essential 8 Flex medium, first in a 1:1 ratio with cStemPro®-34, then only in the Essential 8 Flex™ medium). Colonies (e.g., cell clumps) generally appear 15-21 days after reprogramming. The reprogrammed colonies were identified and selected for picking after a live staining for the cell membrane marker TRA1-60. In details, cells were washed with warm PBS and then incubated with FITC conjugated antibody anti human TRA1-60 (diluted 1:100 in fresh Essential 8 Flex medium and the filtered using a syringe filter SFCA membrane, 0.2 µm) for 1 h at 37° C. After the incubation cells were washed with fresh Essential 8 Flex medium and then examined under a fluorescent microscope. The successfully reprogrammed colonies were marked and manually picked for expansion on vitronectin coated plates. The picked cell colonies were cultured on vitronectin-coated culture plate in complete Essential 8 Flex™ medium at 37° C./4% $O_2$/5% $CO_2$. The cell colonies were allowed to attach for 24 h prior to changing the medium every day. The iPSCs were then cultured in Essential 8 Flex medium and on vitronectin-coated culture vessels with daily medium change.

Skin fibroblasts reprogramming. Two days before transduction, the fibroblast cells were plated on a 6-well plate at the appropriate density to achieve between $2 \times 10^5$-$3 \times 10^5$ cells per well on the day of transduction in fibroblast medium (DMEM high glucose). On the day the fibroblast cells were reprogrammed, the cells were counted and transduced with Sendai virus CytoTune 2.0™ (according to the manufacturer's instructions). More specifically, cells were counted and the volume of each virus needed to reach the target multiplicity of infection (MOI) and the titer information on the CoA was determined as follows:

Vol virus(µl)=MOI CIU/cell)×$n°$ of cells/titer of virus (CIU/mL)×$10^{-3}$(µl/mL)

The cells were harvested and seeded in 6-well plates with 2,5-$5 \times 10^5$ cells/well for transduction. The calculated volumes of each of the 3 CytoTune 2.0™ Sendai tubes were added to 1 mL of fibroblast medium pre-warmed to 37° C. The mixture was gently pipetted up and down. An additional 1 mL of fibroblast medium was added to each well and cells were incubated overnight. The day after the medium with the virus was removed and fresh medium was added. Seven days after the reprogramming, the fibroblast cells were passed and $5 \times 10^5$ cells were placed on vitronectin-coated culture dishes (100 mm Petri dish). Eight days after reprogramming, the cells were placed in the Essential 8 Flex™ medium. Colonies (e.g., cell clumps) generally appear 15-20 days after reprogramming. Selection of the reprogrammed colonies was made after a live staining, see procedure described above for the PBMCs reprogramming. The cells colonies were manually picked and transferred on vitronectin- or laminin-coated plates. Upon reprogramming, the obtained clinical-grade iPSCs acquired self-renewal capabilities and expression levels of pluripotent genes typical of pluripotent stem cells, while showing a high level of homogeneity across the population at single-cell analysis.

iPSCs differentiation into an endoderm. Three days prior to differentiation, a single-cell passaging with Accutase™ was performed and the cells were plated on laminin (recombinant human laminin 521)-coated plates. The cells were cultured in Essential 8 Flex™ medium, supplemented with Revita Cell™ for the first 24 hours after plating. The cells were placed at 37° C. in ambient $O_2$/5% $CO_2$ overnight before starting the differentiation. To promote endoderm specification (at days 1 and 2), the cells were washed with DMEM/F-12 medium and were then cultured with in the RPMI/B27 (minus insulin) medium supplemented with 1% knockout serum replacement, 100 ng/mL Activin A and 3 µM CHIR99021. The cells were cultured for 2 days at 37° C. in ambient $O_2$/5% $CO_2$. To promote endoderm commitment (definitive endoderm, at days 3 to 5), the cells were washed with DMEM/F-12 medium and were then cultured in the RPMI/B27 (minus insulin) supplemented with 100 ng/mL Activin A. The cells were cultured for 3 days at 37° C. in ambient $O_2$/5% $CO_2$. To promote differentiation in the posterior foregut (at days 6 to 8), the cells were washed with the DMEM/F-12 medium and were then cultured for three days in the RPMI/B27 medium (with insulin) supplemented with 2% knockout serum replacement, 20 ng/mL BMP4 and 10 ng/mL bFGF. Endodermal cells differentiated from iPSCs expressed markers typical of derived definitive endodermal cells and posterior foregut cells, both at mRNA and protein levels.

Endoderm differentiation into hepatocyte-like cells (iHeps). To promote hepatic specification (hepatoblasts formation), the cells were cultured for 2 days in the RPMI/B27 medium (with insulin) supplemented with 2% knockout serum replacement 20 ng/mL BMP4 and 10 ng/mL bFGF. To promote the first step in hepatic maturation (e.g., immature hepatocytes formation), the cells were washed in the DMEM/F-12 medium and cultured for five days in RPMI/B27 (with insulin) supplemented with 2% knockout serum replacement and 20 ng/mL HGF. To promote the second step in hepatic maturation (e.g., mature hepatocytes formation), the cells were washed cells with the DMEM/F-12 medium and were cultured for 10 days in the William's E medium supplemented with Primary Hepatocytes Maintenance Supplement, 20 ng/mL OSM and 10 µM dexamethasone. Upon 2D differentiation, endodermal cells acquire markers typical of both immature and mature hepatocyte-like cells, and perform functions unique to mature hepatocytes (such as albumin secretion, urea synthesis and cytochrome P450 3A4 activity).

iPSCs differentiation into mesenchymal progenitor cells (iMPCs or iMSCs). Three days prior to differentiation, a single-cell passaging with Accutase™ was performed, cells were plated on vitronectin-coated plates and cultured in an Essential 8 Flex™ medium, supplemented with Revita Cell™ for the first 24 hours after plating. Cells were washed in the DMEM/F-12 medium and were then cultured for two weeks with mesenchymal stem cell (MSC) medium (DMEM/high glucose, 10% knockout serum replacement, 1% Pen/Strep, glutamine, HEPES, non-essential amino acids). After, the cells were cultured on plates without coating in the MSC medium. Starting from passage 4, cells are considered mesenchymal progenitor cells. They were indistinguishable from umbilical cord matrix stem cells at immunofluorescence and flow cytometry, and their multipotency was proven by osteogenic and adipogenic differentiation potential.

iPSCs differentiation into endothelial progenitor cells (iEPCs). Three days prior to differentiation, a single-cell passaging with Accutase™ was performed, cells were plated on laminin (recombinant human laminin 521)-coated plates and cultured in the Essential 8 Flex™ medium, supplemented with Revita Cell™ for the first 24 hours after plating. To start differentiation and promote mesoderm induction, cells are washed with the DMEM/F-12 medium and cultured for two days in the StemDiff™ APEL™ medium supplemented with 6 µM CHIR99021, 10 ng/ml Activin A and 20 ng/ml BMP4. To promote endothelial differentiation, the cells were washed with the DMEM/F-12 medium, cultured for 5 days in the StemDiff™ APEL™ medium supplemented with 10 ng/mL bFGF, 20 ng/mL BMP4 and 50 ng/mL VEGF.

The obtained iEPCs acquired a morphology comparable to umbilical vascular endothelial cells (HUVEC), expressed markers typical of human progenitor endothelial cells (such as VE-cadherin at immunofluorescence and CD-31 in at least 60% of the cells at flow cytometry) and were capable of forming vessels when cultured in Matrigel® (tube formation assay). From day 7 cells were maintained in endothelial amplification medium (complete EBM2 medium: EBM2 basal medium supplemented with EGM2 BulletKit from Lonza) on vitronectin-coated plates.

Organoids generation. The iEPCs were dissociated using Accutase™ and resuspended in a complete EBM2 medium at the density of 700 000 viable cells/mL. The iMPCs were dissociated with Accutase™ and resuspended in complete DMEM medium at the density of 200 000 viable cells/mL. The hepatic cells were dissociated with Accutase™ and resuspended in complete William'E medium/complete EBM2 (1:1) medium at the density of 1 000 000 viable cells/mL. The iEPCs, iMPCs and hepatic cells were mixed at the ratio of 1 (hepatic):0.7 (iEPCs):0.2 (iMPCs), and plated in Ultra-Low Attachment T-25 Spheroid Microcavity Flasks (Corning) with 157 microcavities of 500 µm in diameter and depth per $cm^2$ (a total of 3200 microcavities/flask) (numbers are approximations), with completeWilliam'sEmedium/complete EMB2 (1:1) medium supplemented with, 20 ng/mL OSM and 10 µM dexamethasone. The cells were cultured for 5 days at 37° C. in ambient $O_2$/5% $CO_2$.

Controlled-size organoids formation (FIG. 3C). iEPCs, iMPCs and hepatc cells were combined at the ratio of 1 (hepatic):0.7 (iEPCs):0.2 (iMPCs), and plated into Ultra-Low Attachment (ULA) T-25 Spheroid Microcavity Flasks (Corning). There are 157 microcavities/$cm^2$, and the microcavities are 500 µm in diameter and depth, with a total of 3200 microcavities/flask (numbers are approximations). The organoids resulted to be quite uniform in size, having a diameter of about 50-250 µm. They all presented the same configuration, with most of the mesenchymal and endothelial cells in the core and hepatocyte and biliary cells mostly on the outer surface. No necrosis was seen in the core of such organoids. The organoids expressed liver-specific markers and were able to perform mature liver functions such as albumin secretion in the conditioned medium, urea synthesis and CyP3A4 activity.

Organoid encapsulation (FIG. 4A). Organoids were harvested from the ultra-low attachment flasks and centrifuged at low speed (400 g for 5 minutes) to form a pellet. The pellet (about 3 000 organoids) were resuspended in 5% 4-arm PEG-vinyl sulfone (20 kDa) solution in sterile PBS without calcium and magnesium supplemented with 0.1% N-vinyl-2-pyrrilidone and 0.4 mg/mL Irgacure 2959. A 50 µL droplet of such a solution (containing about 100 organoids) was generated and deposed in a well of a 96-well plate, and subsequently cross-linked under UV light (5 minutes 1090 µW/$cm^2$ at a distance of 4 cm). The generated encapsulated liver tissue was maintained in complete William's E medium/complete EMB2 (1:1) medium supplemented with, 20 ng/mL OSM and 10 µM dexamethasone for 5 days. Five days after encapsulation, the OSM supplementation was suspended and the ratio complete Williams'E medium/complete EBM2 medium was changed from 1:1 to 4:1. The tissue was cultured at 37° C. in ambient $O_2$/5% $CO_2$ and the medium was changed every other day. Albumin secretion was assessed weekly in the conditioned medium. Encapsulated organoids preserved their ability to secrete albumin through the hydrogel over more than 7 weeks of culture, proving their survival and maintenance of their differentiated status within the polymer while confirming the diffusion of the secreted protein outside of it. The encapsulated liver tissue is solid enough to be manipulated with instrument without losing its shape and integrity.

Degradable hydrogel preparation. Proteolytically degradable PEG vinyl sulfone hydrogels ("D-PEG-VS") were prepared with 8-arm PEG-VS (tripentaerythritol core; Mw=40 kDa) obtained from JenKem, catalog number "8ARM(TP)-VS". The 8-arm PEG-VS was dissolved at 5% to 10% (w/v) final concentration in an isotonic HEPES buffer (0.1 M HEPES, 0.1 M NaCl, pH 7.4) to prepare a degradable PEG vinyl sulfone hydrogel precursor solution. The degradable PEG vinyl sulfone hydrogel precursor solution was then mixed with a plasmin sensitive cross-linker having 3 reactive thiols at a 1:1 molar ratio of -SH and -VS groups. The plasmin sensitive cross-linker was a custom synthesis (Genscript, Piscataway, N.J.) and has the amino acid sequence:

Ac-GCYK↓NSGCYK↓NSCG (SEQ ID NO: 1)

In the amino acid sequence of the plasmin sensitive cross-linking, the N-terminal acetyl group is added to remove the electrical charge on this terminal. The arrows indicate the protease cleavage sites. Mixing the PEG vinyl sulfone hydrogel precursor solution and the plasmin sensitive cross-linker initiated a Michael-Type addition (MTA) reaction that was allowed to proceed for at least 5 minutes to cross-link the PEG vinyl sulfone hydrogel and produce the degradable PEG vinyl sulfone hydrogel.

Non-degradable hydrogel preparation. Non-degradable PEG vinyl sulfone hydrogels ("ND-PEG-VS") were prepared with 4-arm PEG-VS (pentaerythritol core; Mw=20 kDa) obtained from JenKem, catalog number "A7025-1" or "4ARM-VS". The 4-arm PEG-VS was dissolved at 5% to 10% (w/v) final concentration in sterile Dulbecco's phosphate buffered saline (D-PBS) (pH 7.4) containing 0.4 mg/100 µl of a photoinitiator (e.g., such as an alpha hydroxy ketone, e.g., 2-hydroxy-4'-(2-hydroxyethoxy)-2-methylpropiophenone sold as IRGACURE 2959 (BASF, Material No. 55047962) (see, e.g., Elisseeff et al. (2005) Biomaterials 26(11): 1211-18) and 0.1% (v/v) N-vinyl-2-pyrrilidone (PVP) (Sigma-Aldrich, St. Louis, USA) to prepare a non-degradable PEG vinyl sulfone hydrogel precursor solution. PVP has been shown to enhance gelation without impacting cytocompatibility (see, e.g., Lin et al (2014) Acta Biomater 10(1): 104-14, incorporated herein by reference). The non-degradable PEG vinyl sulfone hydrogel precursor solutions were prepared at final concentrations of 5% to 10% (w/v), which is equivalent to 2.5-30 mg/100 µl of PEG-VS. The non-degradable PEG vinyl sulfone hydrogel precursor solutions were exposed to ultraviolet light at a constant intensity (1090 µW/cm2 at a distance of 4 cm) for varying radiation times (e.g., from 3-10 minutes) to prepare the non-degradable PEG vinyl sulfone hydrogel.

Dual hydrogel preparation. A degradable PEG vinyl sulfone hydrogel ("D-PEG-VS") was prepared as described above to provide the "inner core" of a dual PEG hydrogel preparation. After the gelation of the inner (degradable) core was complete (approximately 7-10 minutes, depending on solid concentration), the crosslinked inner core was transferred to the center of a 10-µl bead of the non-degradable PEG vinyl sulfone hydrogel precursor solution as described above and exposed to ultraviolet light at a constant intensity (1090 µW/cm$^2$ at a distance of 4 cm) for varying radiation times (from approximately 3-10 minutes) to provide the "outer shell" around the "inner core".

Ovary encapsulation in D-PEG-VS, ND-PEG-VS, and dual PEG hydrogels. The encapsulation of the ovarian tissue was performed in a sterile biohazard cabinet on a heating stage to minimize ambient damage to the tissue. To prepare PEG-based implants, ovarian pieces were transferred from the maintenance media in the incubator and were laid on a hydrophobic slide using an insulin (27 G) needle. Each ovarian piece was about 1 to 1.5 mm$^3$ in volume. Droplets (5 µl) of the PEG precursor were pipetted on the same glass slide and ovarian pieces were transferred into a droplet of degradable PEG vinyl sulfone hydrogel precursor solution. To prepare D-PEG-VS, another 5 µl of a dissolved peptide crosslinker were added to the droplet of PEG-VS and mixed. The slide was then covered with a top slide and allowed to form gels for 5 minutes. After the gelation was complete, the hydrogels were ready to be transplanted.

To prepare non-degradable PEG vinyl sulfone hydrogels with ovarian tissue, droplets (10 µl) of PEG vinyl sulfone precursor solutions with the initiator and PVP were pipetted on a hydrophobic glass slide. The pieces of ovarian tissue were placed on the glass and transferred by a needle into the droplets. The PEG-VS precursor solutions with the tissue were exposed to ultraviolet light at a constant intensity (1090 µW/cm2 at a distance of 4 cm) for varying radiation times (e.g., from 3 to 10 minutes) to prepare the non-degradable PEG vinyl sulfone hydrogel.

For encapsulation of ovarian tissue pieces in dual PEG hydrogel, ovarian pieces were transferred into a droplet of degradable PEG vinyl sulfone hydrogel precursor solution and allowed to gel as described above, then the gelled degradable PEG vinyl sulfone hydrogel was encapsulated in a non-degradable PEG vinyl sulfone hydrogel as described above for the preparation of dual hydrogels.

EXAMPLE II

Encapsulated Tissue Characterization

Cell immunofluorescence. Cells were fixed in 4% paraformaldehyde and permeabilazed in 0,2% Triton X™-100 for 5 min at room temperature. Nonspecific sites were blocked incubating the cells with a 3% blocking serum (corresponding with primary antibody) solution for 30 min at room temperature. Fixed and permeabilized cells were incubated with primary antibody solution (antibodies are diluted in PBS-BSA 2%) for 1 h at room temperature. Cells were then incubated with secondary labelled antibody solution (fluorescence) for 30 min at room temperature protected from the light. During the last 15 min a dye (Pureblue™ nuclei staining, BioRad) was added to stain the nuclei. Cells were mounted with an Antifade™ reagent (ProLong Gold). Fluorescence was analyzed the day after the procedure.

Immunofluorescence on liver organoids. Organoids were fixed in 4% paraformaldehyde and subsequently embedded in paraffin. Paraffin sections were de-paraffined and rehydratated using xylene and ethanol solutions with decreasing concentrations (from 100% to 30%). Nonspecific sites were blocked incubating slides with a 3% blocking serum (corresponding with primary antibody) solution for 20 min at room temperature. Slides were incubated with primary antibody solution (antibodies are diluted in PBS-BSA 2%) for 1 h at room temperature. Slides were incubated with secondary labelled antibody solution (fluorescence) for 30 min at room temperature protected from the light. Slides were mounted with an Antifade™ reagent (ProLong Gold) with DAPI. Fluorescence was analyzed the day after the procedure.

Antibodies used for the immunofluorescence on cells and organoids. Anti-human NANOG dilution 1:10 from Novus Biological; anti-human TRA1-81 dilution 1:50 from Fisher Scientific; anti-human SSEA4 dilution 1:50 from Fisher Scientific; anti-human POU5F1 dilution 1:50 from Novus Biological; anti-human SOX2 dilution 1:50 from Novus Biological; anti-human FOXA2 dilution 1:100 from ABCAM; anti-human SOX17 dilution 1:100 from ABCAM; anti-human CXCR4 dilution 1:100 from ABCAM; anti-human GATA4 dilution 1:50 from ABCAM; anti-human AFP dilution 1:100 from DAKO; anti-human Albumin dilution 1:100 from DAKO; anti-human E-Cadherin dilution 1:100 from BD Bioscience; anti-human αSMA dilution 1:100 from ABCAM; anti-human fibronectin dilution 1:100 from ABCAM; anti-human CD31 dilution 1:100 from ABCAM; anti-human VE-cadherin dilution 1:100 from ABCAM; anti-human CK19 dilution 1:100 from ABCAM, anti-human ZO1 dilution 1:100 from ABCAM, anti-human EpCAM dilution 1:100 from ABCAM.

FACS analysis. $0.5-1 \times 10^6$ cells were aliquoted into each assay tube. Cells were stained with 100 µL of fluorochrome-conjugated primary antibody solution (membrane antigen) for 20 min at room temperature (Protect from the light). Cells were subsequently fixed with 4% paraformaldehyde for 10 min at room temperature. Cells were permeabilized with 1% Triton X™-100. Cells were stained with 100 µL of fluorochrome-conjugated antibody solution (intracellular antigen) and incubate in the dark at room temperature for 20 min. Cells were resuspended in 0.5 mL PBS-BSA 1%, kept at 4° C. and analyzed. Antibodies used for the FACS from BD Bioscience: PE anti-human SSEA4; Alexa 647 anti-human NANOG; PERCP-CY 5,5 anti-human TRA1-81; APC-R700 anti-human CD117; FITC anti-human CD90; PE anti-human CD133; PE anti-human CD31, PE anti-human CD25, anti-human 7AAD; from Biolegends: APC anti-human CD3, PEcy7 anti-human HLA-DR, PerCp-Cy5.5 anti-human CD69; from Invitrogen: FITC anti-human CFSE.

Real-time RT-PCR. Total RNA was extracted (ReliaPrep™ RNA Cell Miniprep System, Promega) from cultured cells or organoids as a template for synthesis of single-stranded cDNA. Reverse transcription was performed to obtain cDNA. The PCR reaction mix is prepared and afterwards loaded in the plate. The plate is sealed, centrifuged and then load into the instrument. The standard TaqMan qPCR reaction conditions were used. Data was analysed using the comparative CT (ΔΔCT) method for calculating relative quantitation of gene expression. The following gene expression assays (from Thermo Fisher scientific) were used: Hs04399610G1 Nanog Taqman gene expression assay; Hs01895061_U1 POU5F Taqman gene expression assay; Hs1053049_S1 SOX2 Taqman gene expression assay; Hs00751752_S1 SOX17 Taqman gene expression assay; Hs00171403_M1 GATA4 Taqman gene expression assay; Hs002230853_M1 HNF4A Taqman gene expression assay; Hs00173490_M1 AFP Taqman gene expression assay; Hs00609411_M1 Albumin Taqman gene expression assay; Hs99999905_M1 GAPDH Taqman gene expression assay. Results shown is the mean expression obtained from three repetitions.

Cyp3A4 activity. Cyp3A4 activity was evaluated using P450-Glo™ Assays from Promega, according to manufacturer's instructions.

Urea synthesis. Urea synthesis was measured using Quantichrom urea assay kit™ from Gentaur, according to manufacturer's instructions.

Albumin production. Albumin production was evaluated using the Multigent® microalbumin assay, a quantitative measurement of albumin on the Architect cSystems. It is a turbidimetric immunoassay that uses polyclonal antibodies against human albumin. When the specimen (in that case 200 µl supernatant from each well of 96-well plate, collected 48 h after medium changing) is mixed with the reagents, albumin in the specimen combines with the anti-human albumin antibody (goat) in the reagent to yield an insoluble aggregate that causes increased turbidity in the solution. The degree of turbidity is proportional to the concentration of albumin in the specimen, and can be measured optically. Reagent kit: 2K98-20 MULTIGENT Microalbumin.

Hematoxylin and eosin (H&E) staining. Sections of liver bud, organoids and ovary were brought to distilled water. Nuclei were stained with the alum haematoxylin. The sections were rinsed in running tap water and differentiate with 0.3% acid alcohol. The sections were stained with eosin for 2 min. The sections were dehydrated, cleared and mounted.

Mixed lymphocyte reaction. The MLR was performed twice on either $10^6$ effector PBMCs, $10^5$ allogeneic mature dendritic cells (mDC) liver organoids composed of $6 \times 10^5$ cells. The target cells or tissues were irradiated and left free or encapsulated (+gel) in the hydrogel before the 6-day co-culture of the MLR.

IFN-γ production. IFN-γ production was evaluated with the human IFN-γ Standard ABTS ELISA Development Kit from PEPROTECH, according to manufacturer's instructions.

Alzarin Red S staining. Calcium deposits of iMPC-derived osteocytes were evaluated using Alzarin Red S staining from Sigma Aldrich. Cells were fixed in 4% paraformaldehyde, then washed with PBS and incubated with Alzarin Red S for 5 min at room temperature. After incubation the Alzarin Red S solution was removed and cells were washed with PBS. Stained specimens were examined microscopically.

Neutral lipids stain. Neutral lipid stain in iMPC-derived adipocytes was performed using the HCS LipidTOX™ Neutral Lipid Stain from Invitrogen, according to manufacturer's instruction.

Tube formation assay. iPSC-derived endothelial progenitor cells (iEPC) were dissociated with Accutase™ and then plated at a density of $7 \times 10^4$ per well of 24-well plate coated with growth factor-reduced Matrigel (Corning) in complete EBM2 medium. Plates were incubated overnight at 37° C. in ambient $O_2$/5% $CO_2$. After 16 h of incubation tube formation was visualized under a light microscope.

Cell viability assay. Cell viability of the encapsulated liver tissues was determined with the LIVE/DEAD™ Viability/Cytotoxicity Kit, for mammalian cells from ThermoFisher Scientific. The ELTs (generated in 96-well plates) were incubated each with 150 µl of a solution of PBS, ethidium homodimer-1 and calcein-AM (prepared according to manufacturer's instruction) for 30 min at 37° C. in ambient $O_2$/5% $CO_2$. After the incubation green and red fluorescence was analyzed under a fluorescent microscope. Ammonia metabolism. ELTs were incubated with complete ELT medium (complete William's E medium/complete EBM2 medium 4:1) supplemented with 1 mM ammonium chloride, 4 mM L-glutamine/alanine and 4 mM L-ornithine for 24 h. After 24 h the spent culture medium was harvested and centrifuged at 500 g for 5 minutes for determination of ammonia concentration using Ammonia Assay kit from ABCAM, according to the manufacturer's instruction. Urea production of ELTs was measured before and after incubation with complete ELT medium supplemented with 1 mM ammonium chloride, 4 mM L-glutamine/alanine and 4 mM L-ornithine for 24 h using Quantichrom urea assay kit™ from Gentaur, according to manufacturer's instructions.

Tacrolimus metabolism (FIG. 4K): ELTs were incubated with complete ELT medium (complete William's E medium/ complete EBM2 medium 4:1) supplemented with 20 ng/ml FK506 (Tacrolimus) from Fujisawa Healthcare, with or without supplementation with 20 µM rifampicin, for 12 hours at 37° C. in ambient $O_2$/5% $CO_2$. After 12 h, spent medium was harvested and Tacrolimus concentration was measured by liquid chromatography tandem mass spectrometry assay. The ammonium-adduct ions with transitions of m/z 821,5→768,6 (tacrolimus) were measured in selective reaction monitoring mode using electrospray ionization.

ELT post-freezing characterization. ELT were froze in freezing medium (complete ELT medium 10% DMSO) for 3 days at −80° C. After 3 days ELTs were thawed and albumin production as well as CyP3A4 activity were measured 24 h and 1 week after thawing as described above.

Foreign body reaction assessment. ELTs were implanted within the peritoneal cavity (as illustrated in FIG. 4M) of immunocompetent mice without immunosuppressive treatment. The ELTs were then removed from the peritoneal cavities after 1 week (FIG. 4N left) and 4 weeks (FIG. 4N right), and examined for the presence of signs of foreign body reaction (i.e. fibrosis, inflammation).

Teratoma formation assay. Undifferentiated iPSCs were injected subcutaneously or implanted subcutaneously upon encapsulation in 5% PEG-VS hydrogel into NOD/SCID IL-2R$\gamma^{-/-}$ mice. After 8 weeks mice were sacrificed and teratoma formation was assessed.

Preliminary assessment of short-term in vivo efficacy of xenotransplantation of the encapsulated liver tissue in immunocompetent mice with acute liver failure without immunosuppression. Acute liver failure was triggered in immunocompetent Fah$^{-/-}$ (tyrosinemic) mice through withdrawal of the NTBC supplementation from the drinking water. Six animals were transplanted with the encapsulated liver tissue (implantation of a 8×2 mm cylindrical encapsulated liver tissue generated from human cells as described above within the abdominal cavity), and followed for 30 days to assess survival. No immunosuppression was administered despite the xenotransplantation. Six mice receiving the empty biomaterial served as controls. Weight loss at day 7 post-transplant was assessed as secondary outcome. All the animals still alive at day 30 were euthanized and human albumin was specifically measured in mice sera using Human Albumin ELISA Kit from Abcam, according to manufacturer's instructions.

Fourteen human iPSC populations were generated and maintained in strict xeno-free and feeder-free conditions (FIGS. 1A-1D). From skin fibroblasts or 1.5 mL of peripheral blood, 6.3±5.6 highly homogenous iPSC populations were obtained. The iPSCs were reproducibly differentiated to definitive endoderm and posterior foregut (FIGS. 2A-2D), and then further to hepatocyte-like cells expressing liver-specific markers and functions (FIGS. 2E-2H). Starting from a single iPSC population, hepatic progenitor cells (hepatoblasts), endothelial progenitor cells and mesenchymal progenitor cells (including osteocytes and adipocytes) were obtained (FIGS. 2I-2M).

Figure 3A:
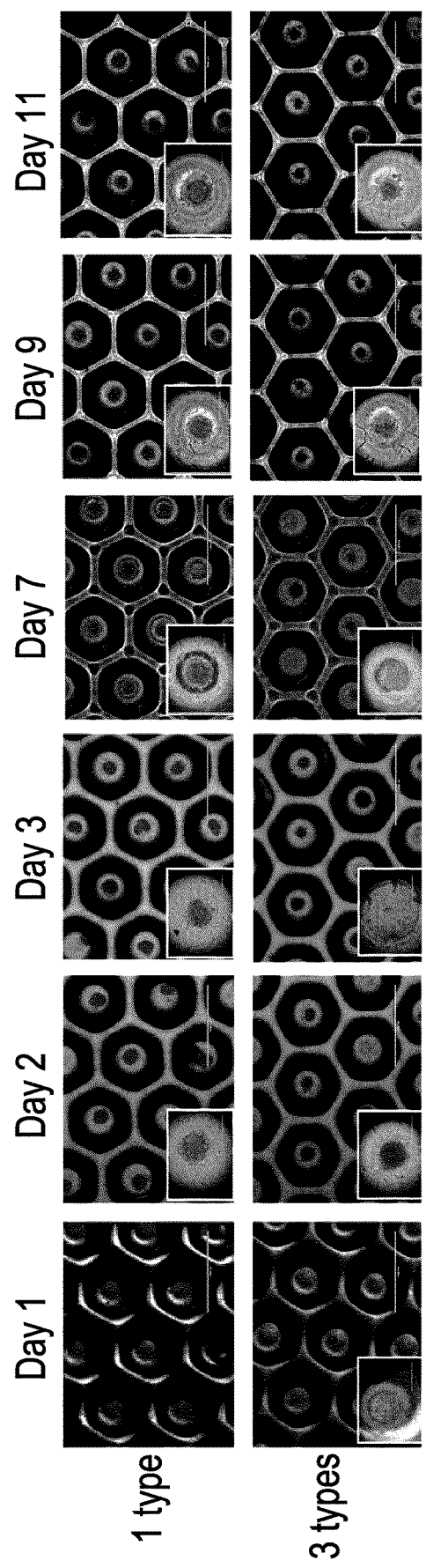
FIGS. 3A to 3F illustrate embodiments of the liver organoids made from iPSC-derived cells. (A) Microscopic view of suspension-grown liver organoids generated with iPSC-derived endoderm-derived/hepatic cells, UCMSCs and HUVECs (1-type) (top panel) or iPSCs-derived endoderm-derived/hepatic cells, endothelial and mesenchymal cells (3-type) (bottom panel) 1, 2, 3, 7, 9 or 11 days post-seeding. (B) Hematoxylin-eosin staining of 1-type (left panel) and 3-type (right panel) liver organoids. (C) Immunofluorescence of albumin, cytokeratin 19 (CK19), EpCam, α-fetal protein (AFP), ZO1 and CD31 of the liver organoid. Scale bar 200 μM. (D) Expression of liver specific markers (AFP and albumin) in undifferentiated iPSCs (diagonal bars), iPSC-derived hepatocytes after 28 days of culture (white bars) and liver organoids after 10 days of culture (light grey bars) as determined by RT-qPCR. Results are shown as the logarithmic fold change in mRNA expression in function of the different genes (identified underneath the X axis). (E) iPSC-derived liver organoids perform functions typical of primary hepatocytes such as urea and albumin synthesis. Results are shown as albumin (ng/24 h/1×10$^6$ cells, left panel) or urea (μg/24 h/1×10$^6$ cells, right panel) secretion in undifferentiated iPSCs, iPSC-derived endodermal cells (after 10 days of differentiation), iPSC-derived hepatoblasts (d18: after 18 days of differentiation), liver bud (d10: after 10 days from seeding), 1-type liver organoid (d10: after 10 days from seeding), 3-type liver organoid (d10: after 10 days from seeding) and primary human hepatocytes. (F) iPSC-derived liver organoids exhibit CyP3A4 activity. Results are shown as fold increase in Cyp3A4 activity (when compared to iPSCs) for hepatoblasts (d16: after 16 days of differentiation), iPSC-derived hepatocytes (d28: after 28 days of differentiation) or 3-type liver organoids (d10: after 10 days from seeding).
Figure 3B:
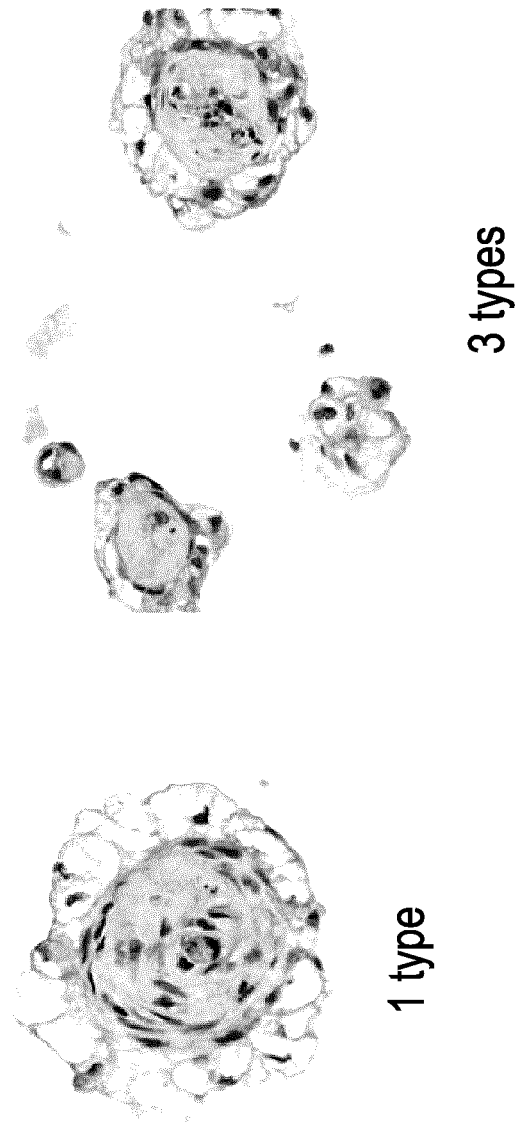
Figure 3C:
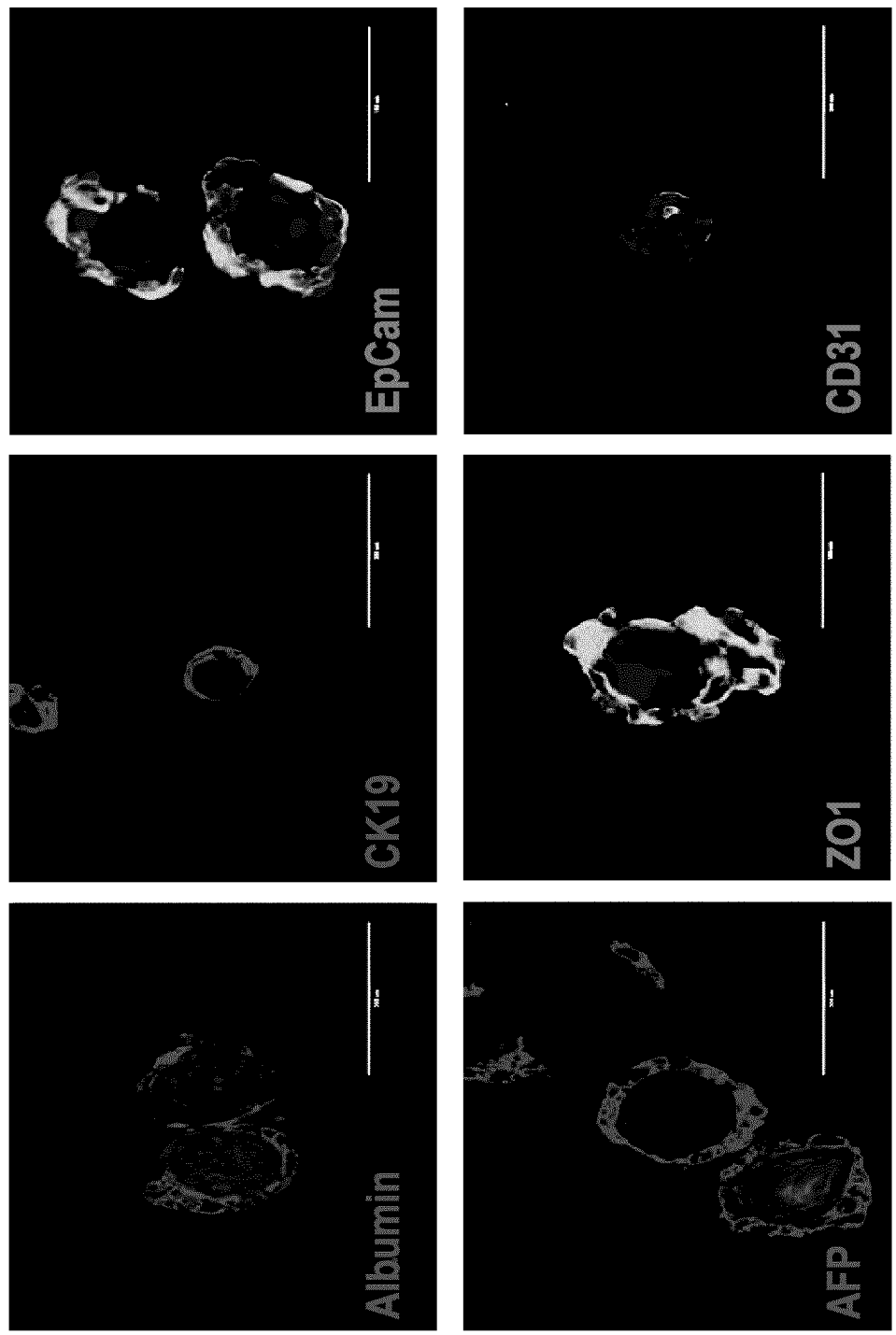
Figure 3E:
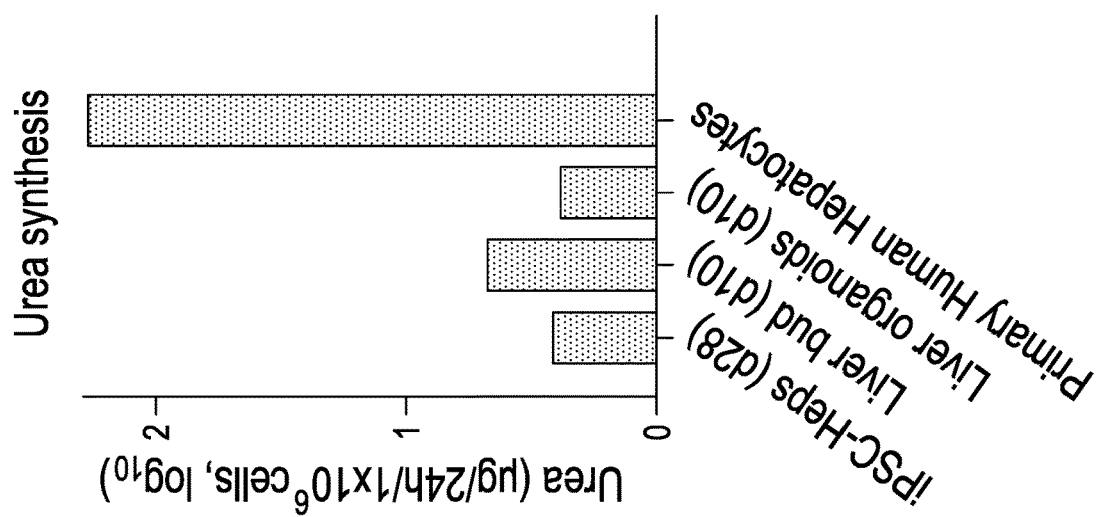
Figure 3E:
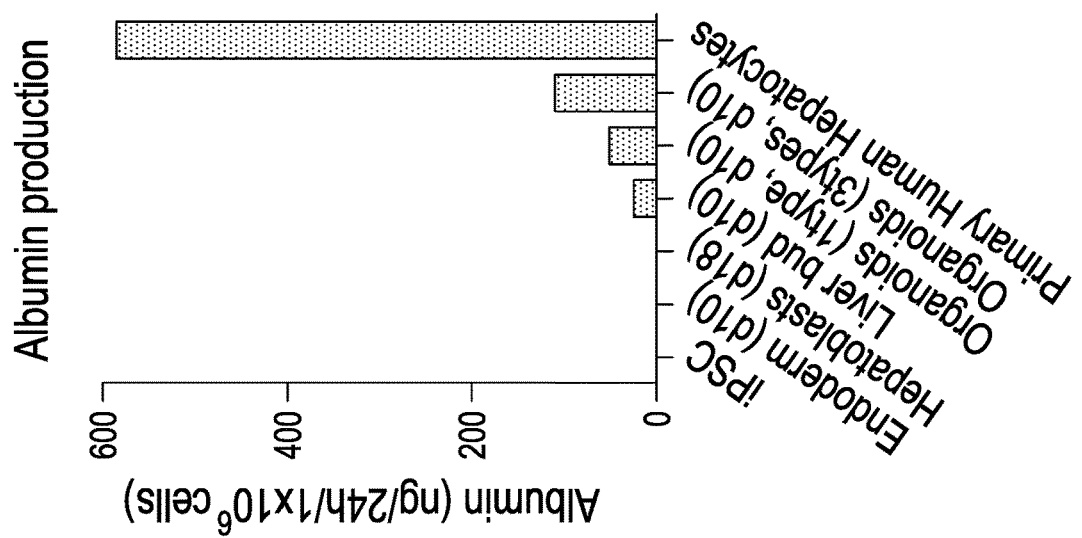
Figure 3D:
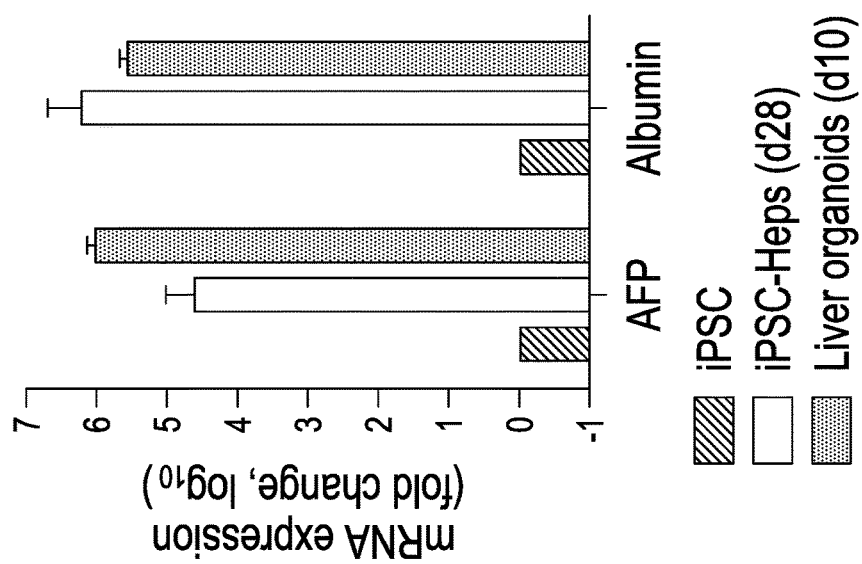
Figure 3F:
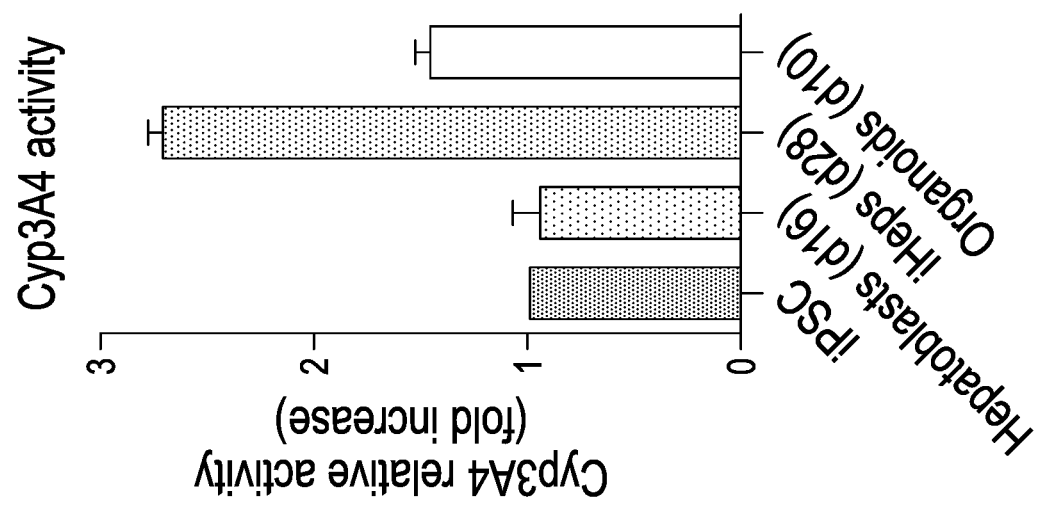

The three iPSC-derived cell types were cultured in suspension in fixed-size, very-low-attachment microwells (FIG. 3A). The controlled-size organoids (50-250 µm in diameter, FIG. 3C) differentiated within the microwells upon 5 days in a maturation medium, showed a 3D structure reminiscent of a human liver (FIGS. 3B and 3C), expressed liver markers (FIG. 3D), and acquired significant albumin and urea secretion capacity (FIG. 3E) as well as CyP3A4 activity (FIG. 3F).

Figure 4B:
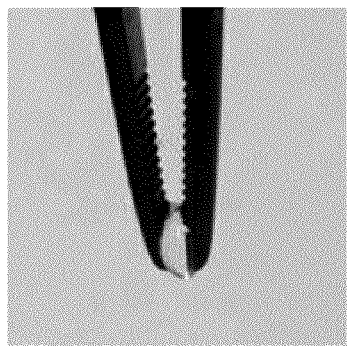
Figure 4B:
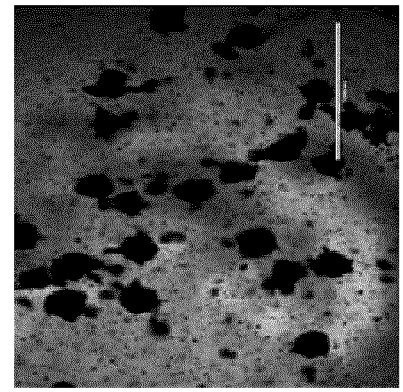
Figure 4B:
Figure 4B:
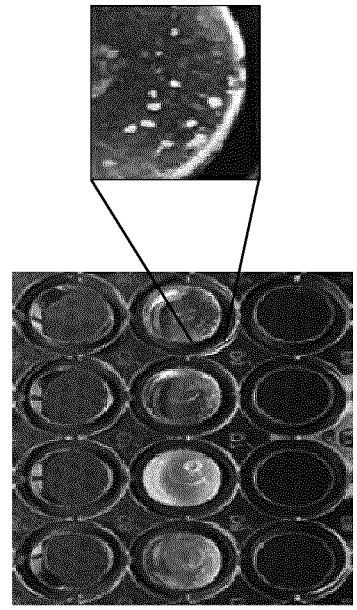
Figure 4B:
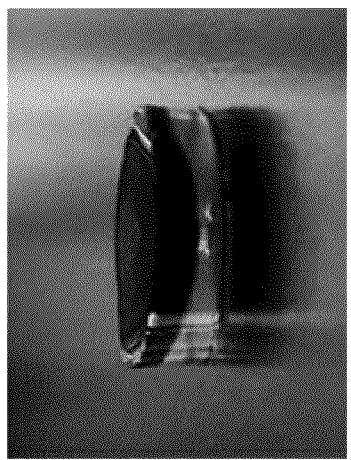
Figure 4B:
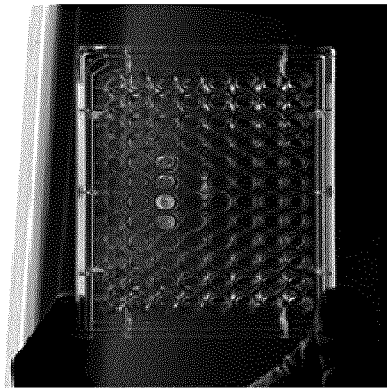
Figure 4C:
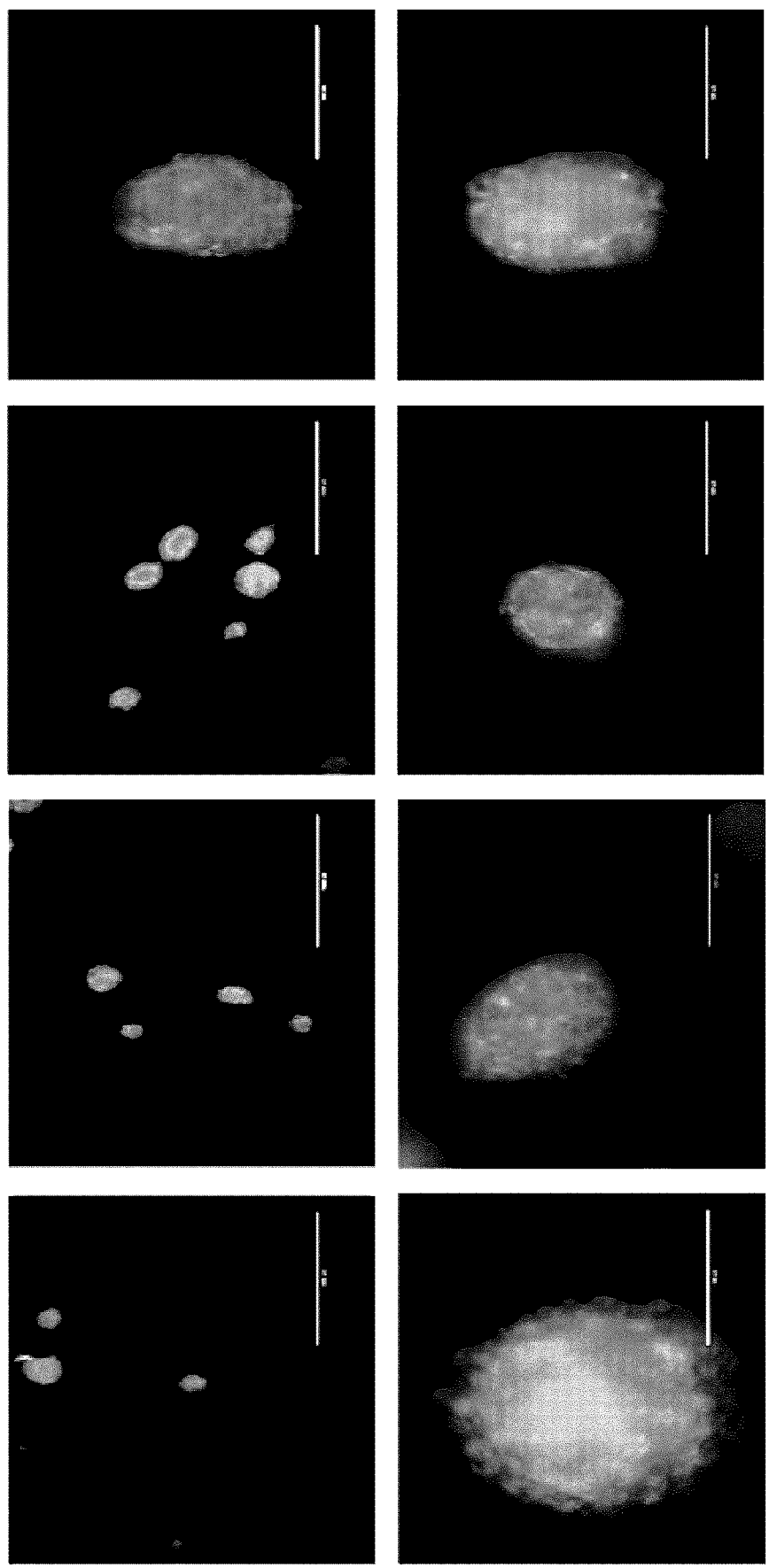
Figure 4D:
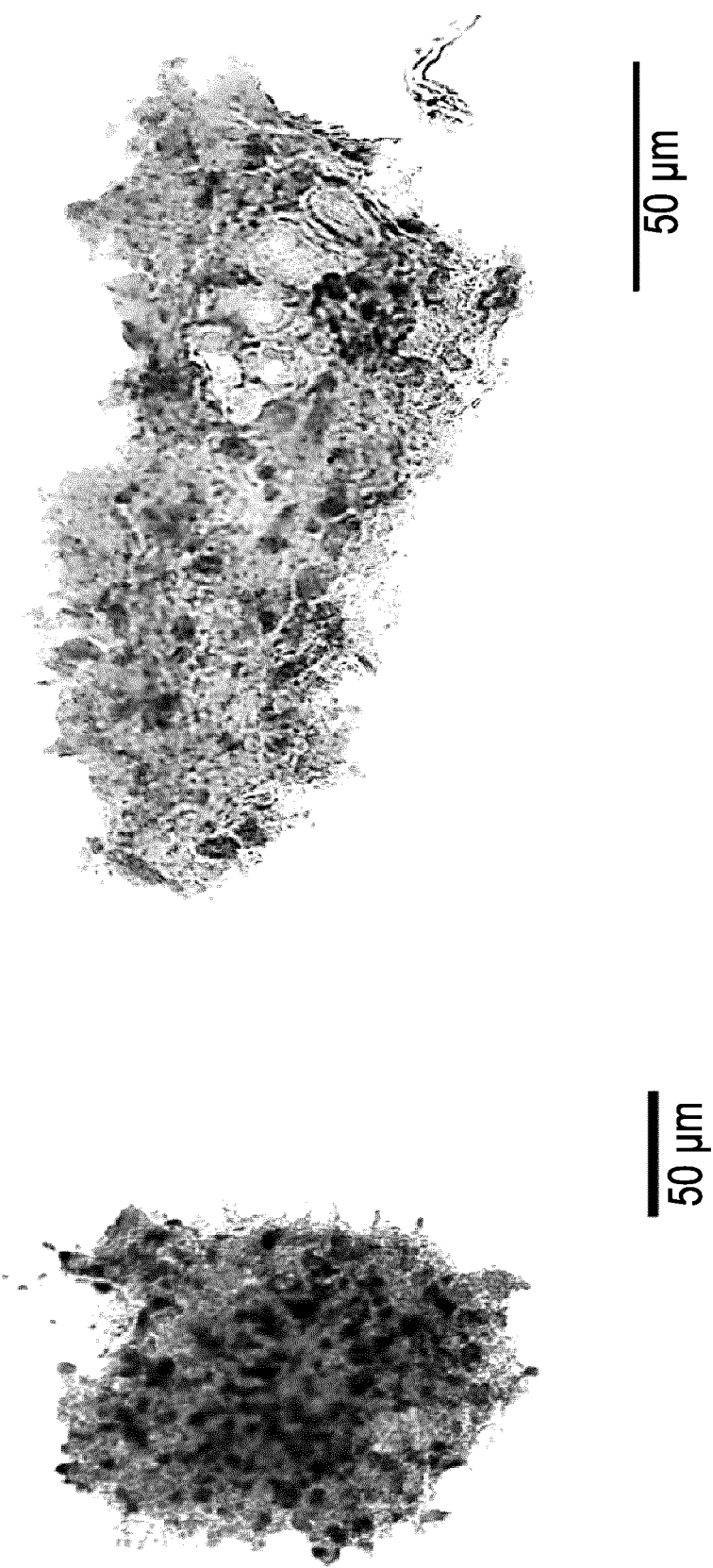
Figure 4E:
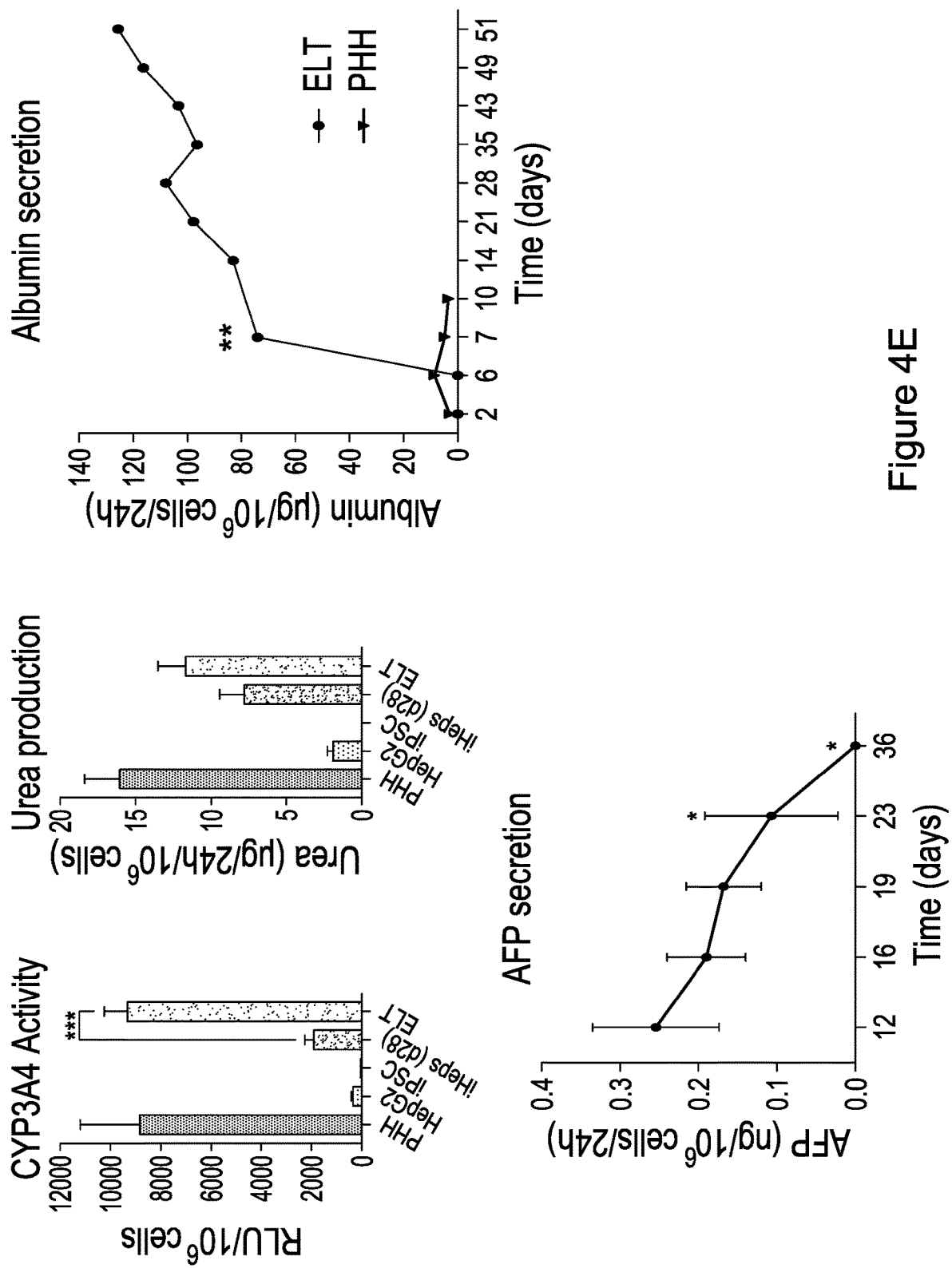
Figure 4F:
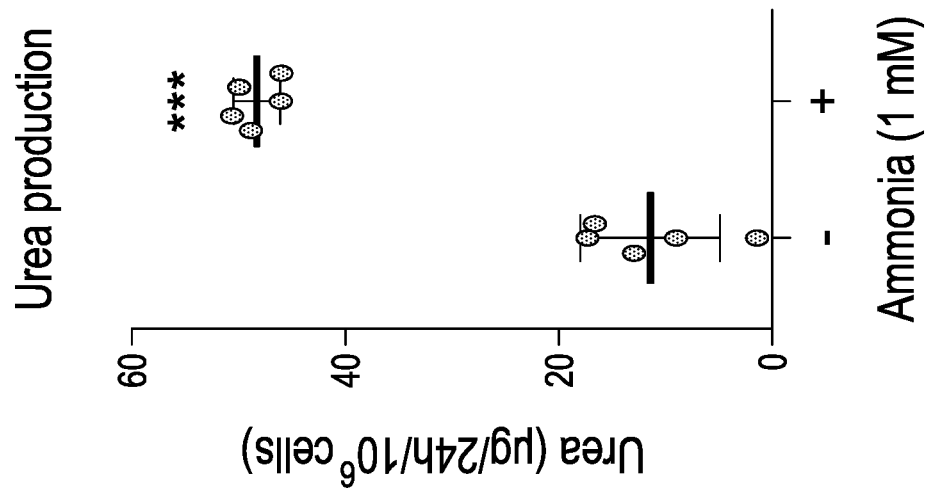
Figure 4F:
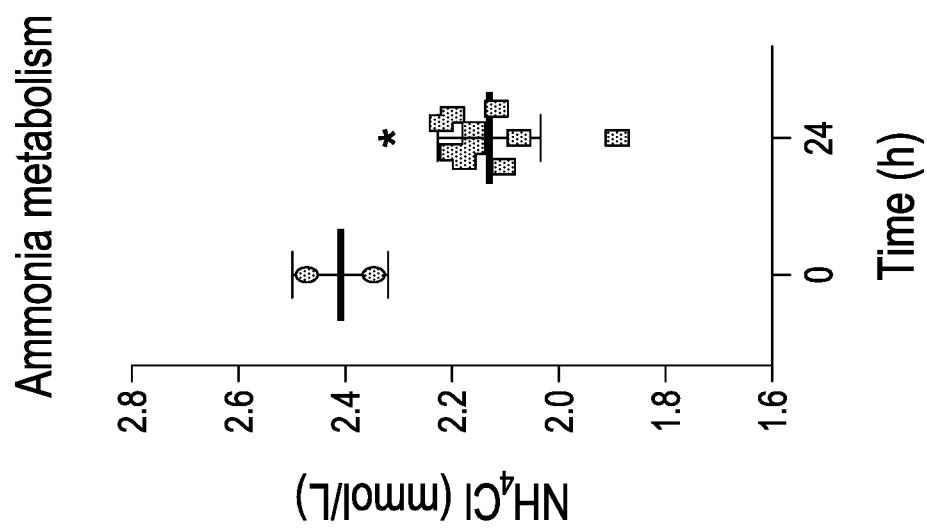
Figure 4G:
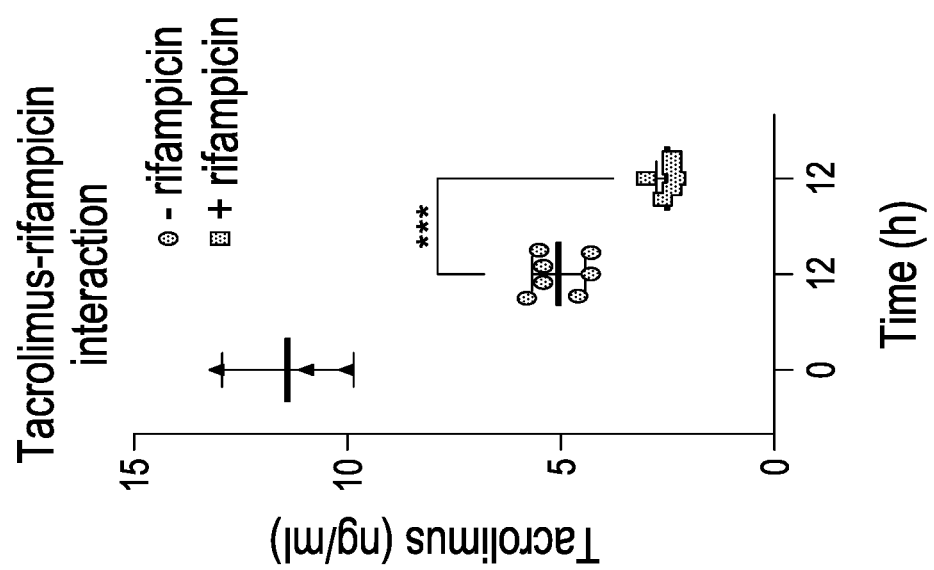
Figure 4H:
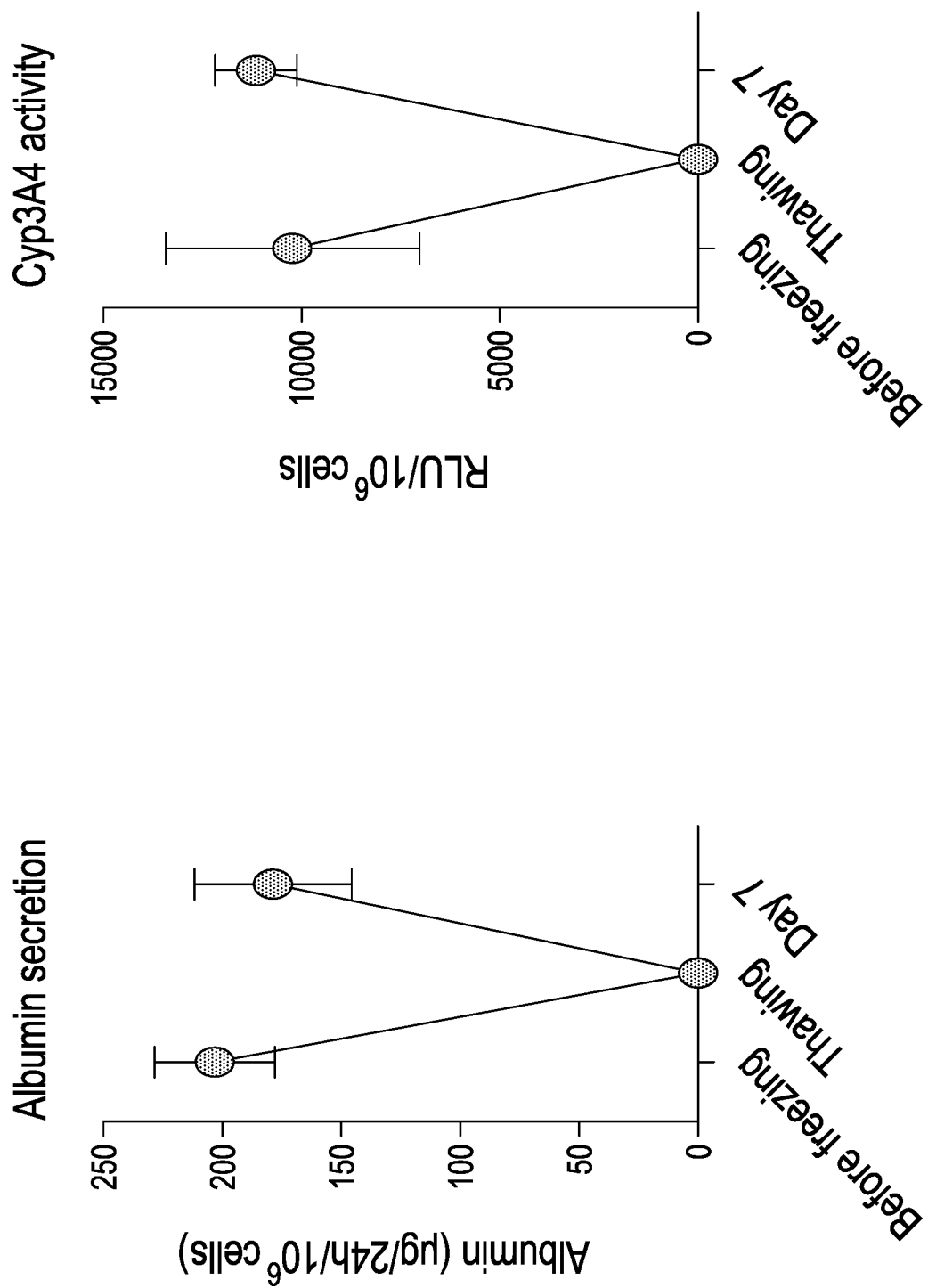
Figure 4I:
Figure 4J:
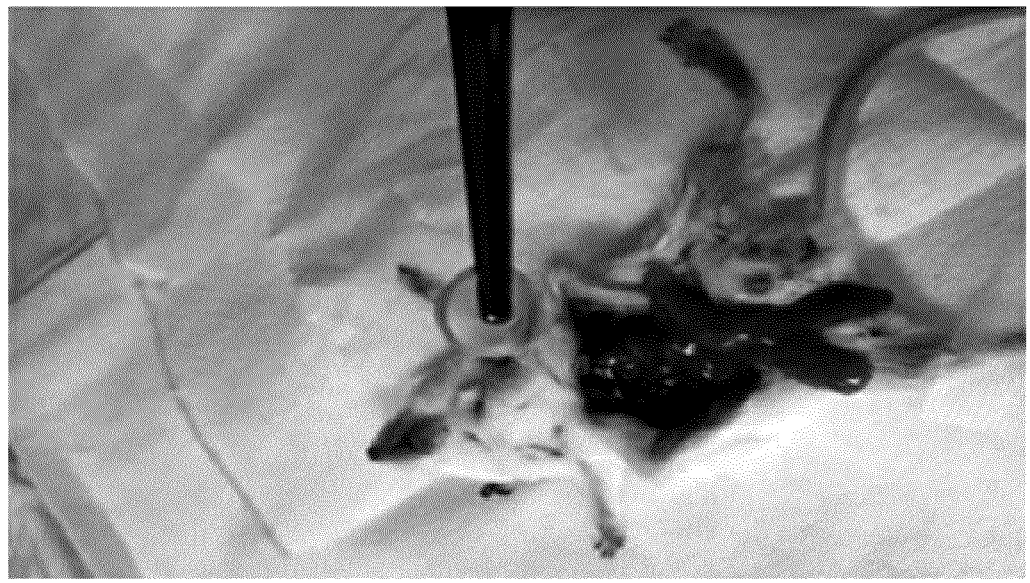
Figure 4J:
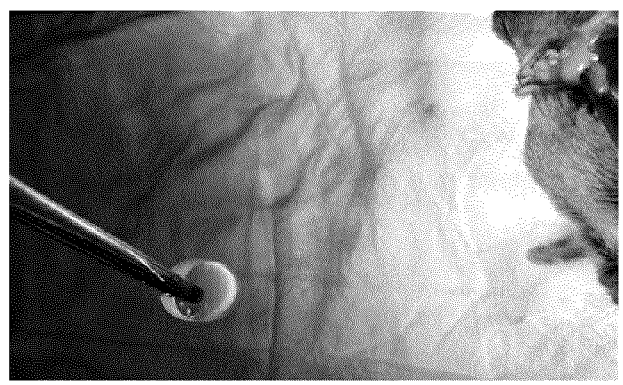
Figure 4J:
Figure 4K:
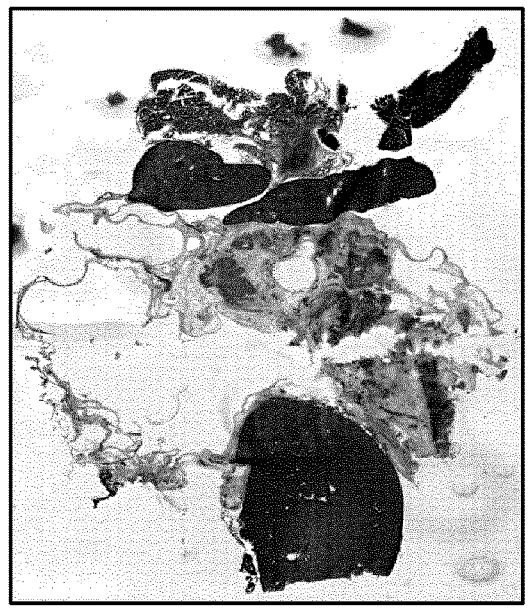
Figure 4K:
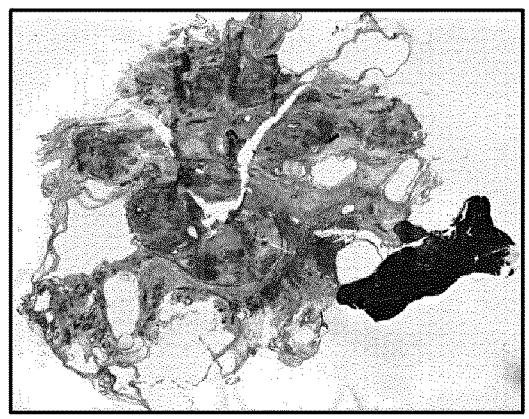
Figure 4K:
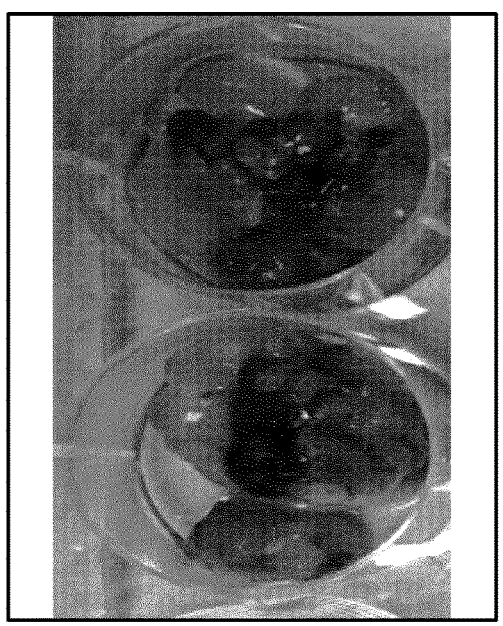
Figure 4L:
Figure 4L:
Figure 4L:
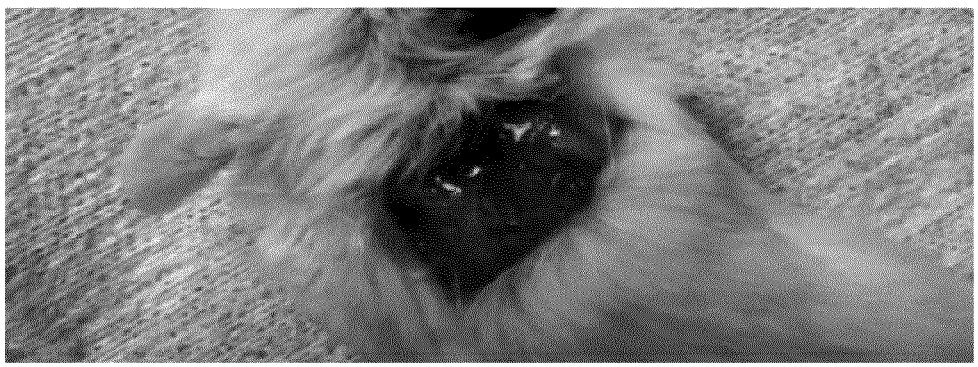
Figure 4M:
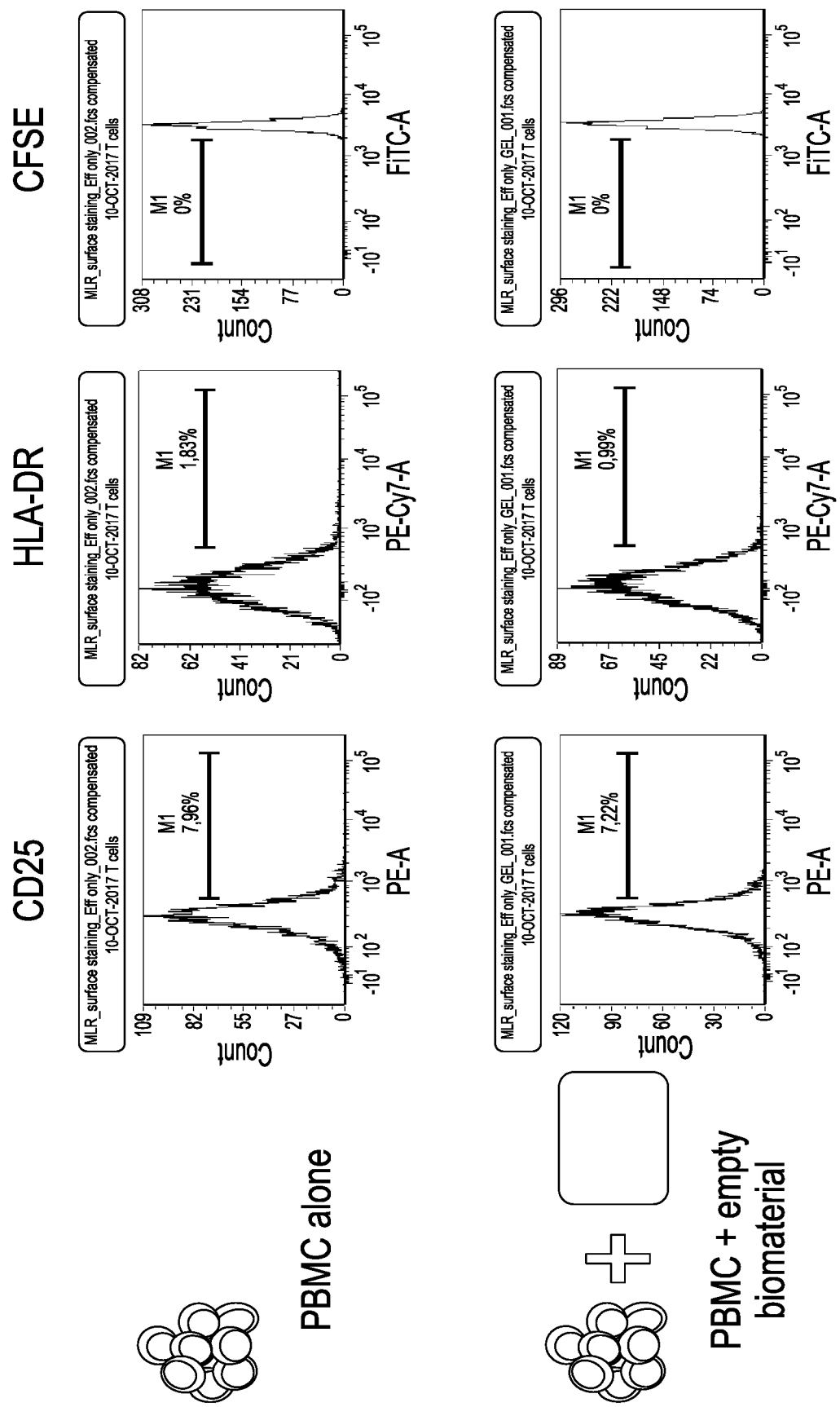
Figure 4M:
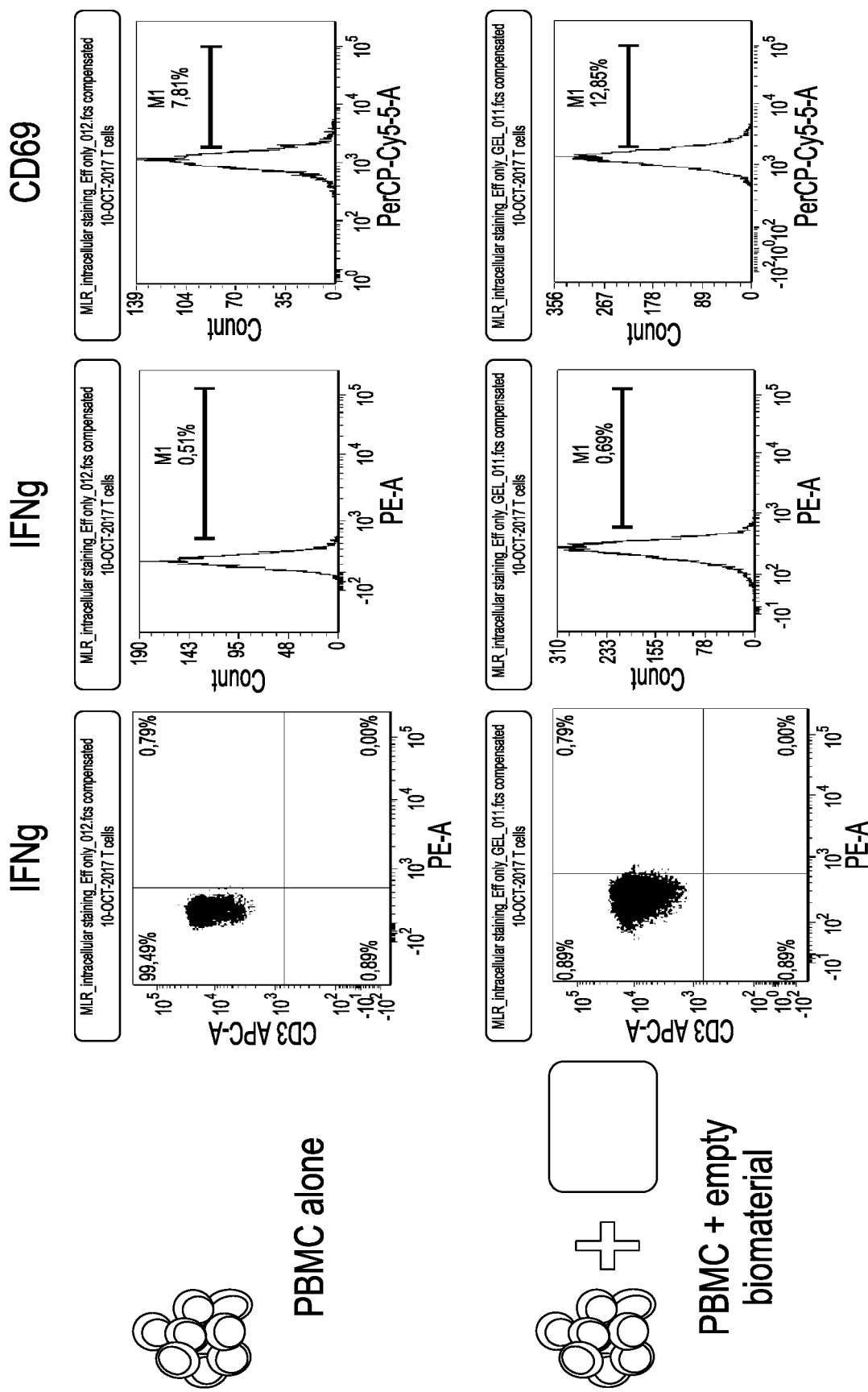
Figure 4M:
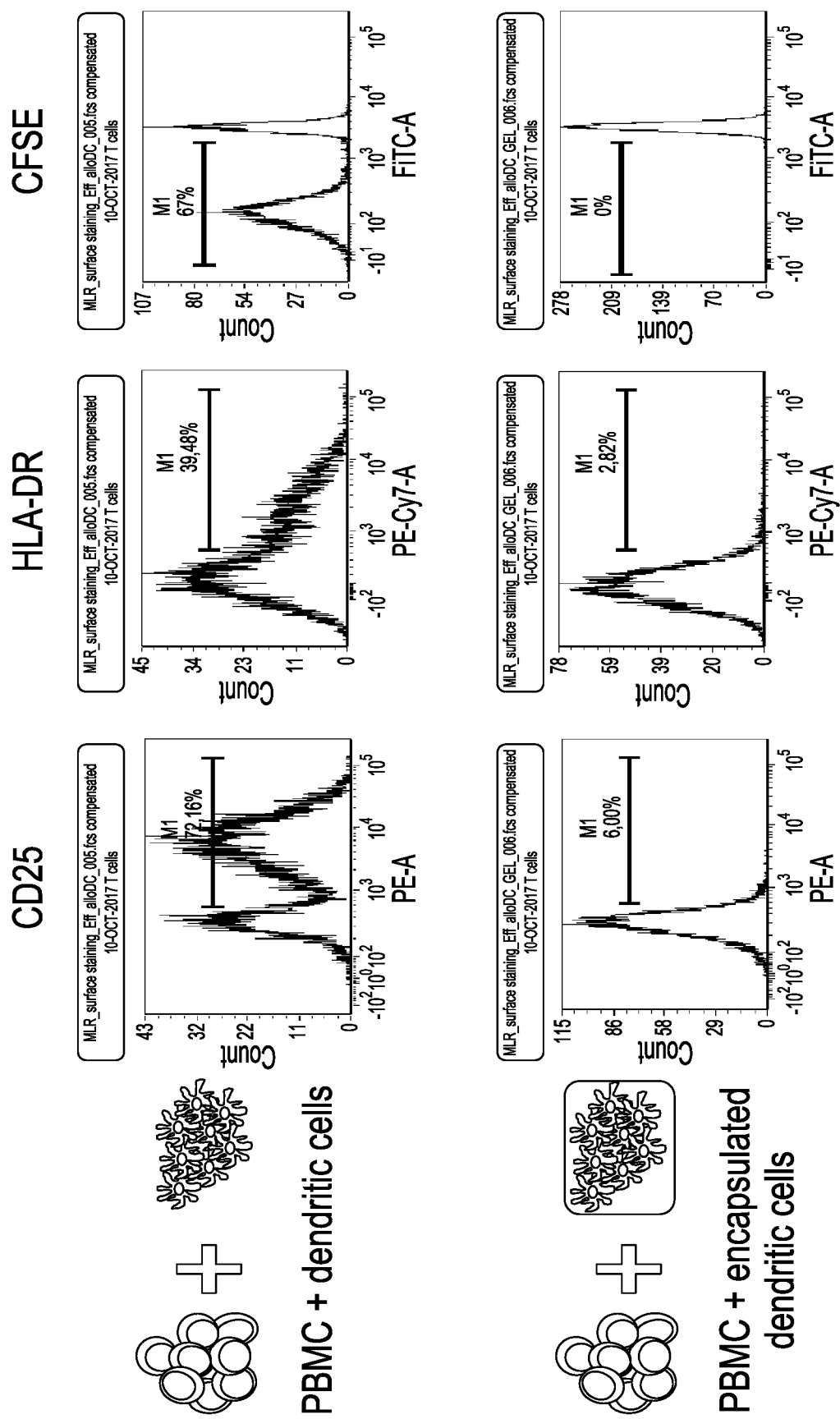
Figure 4M:
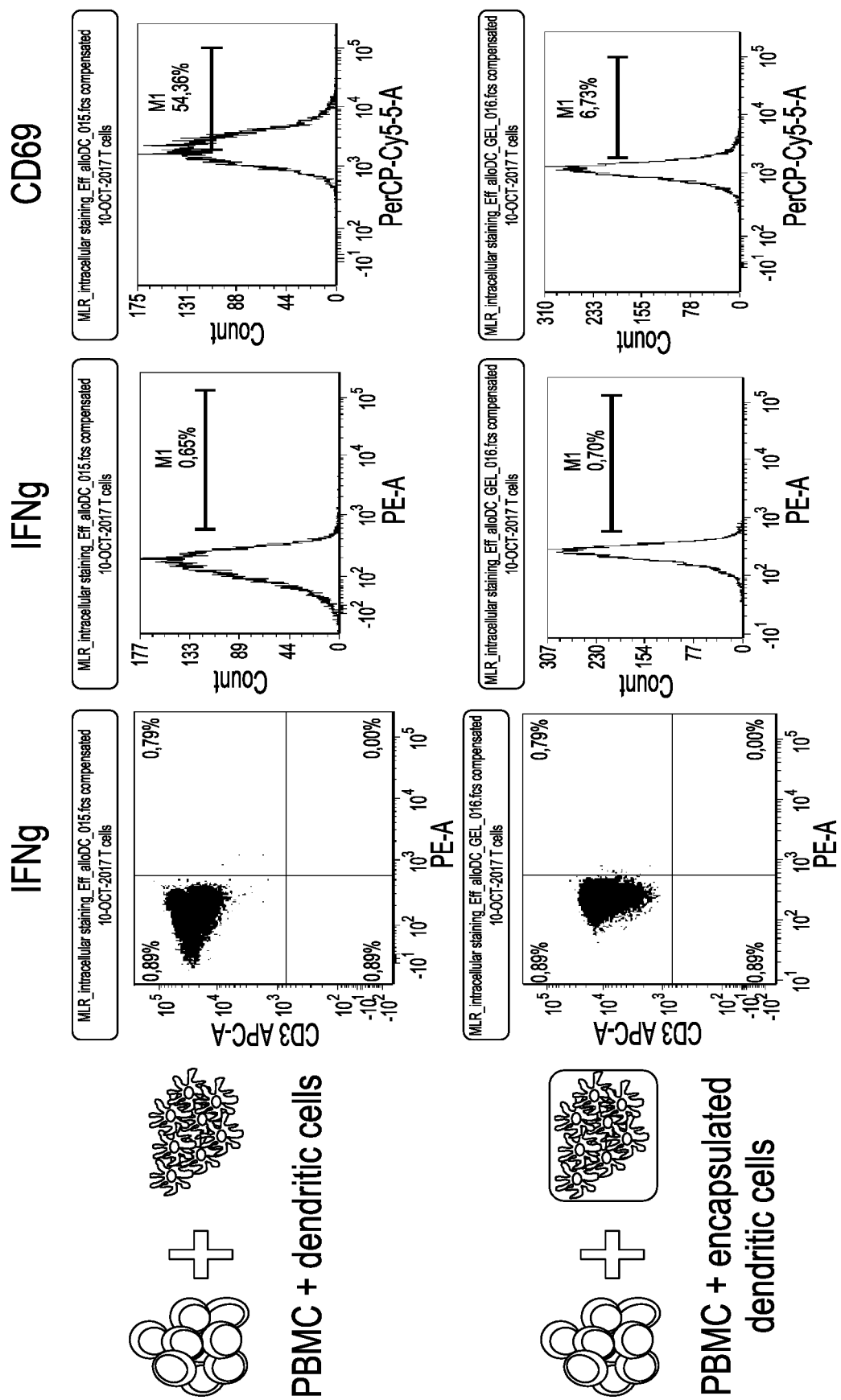
Figure 4M:
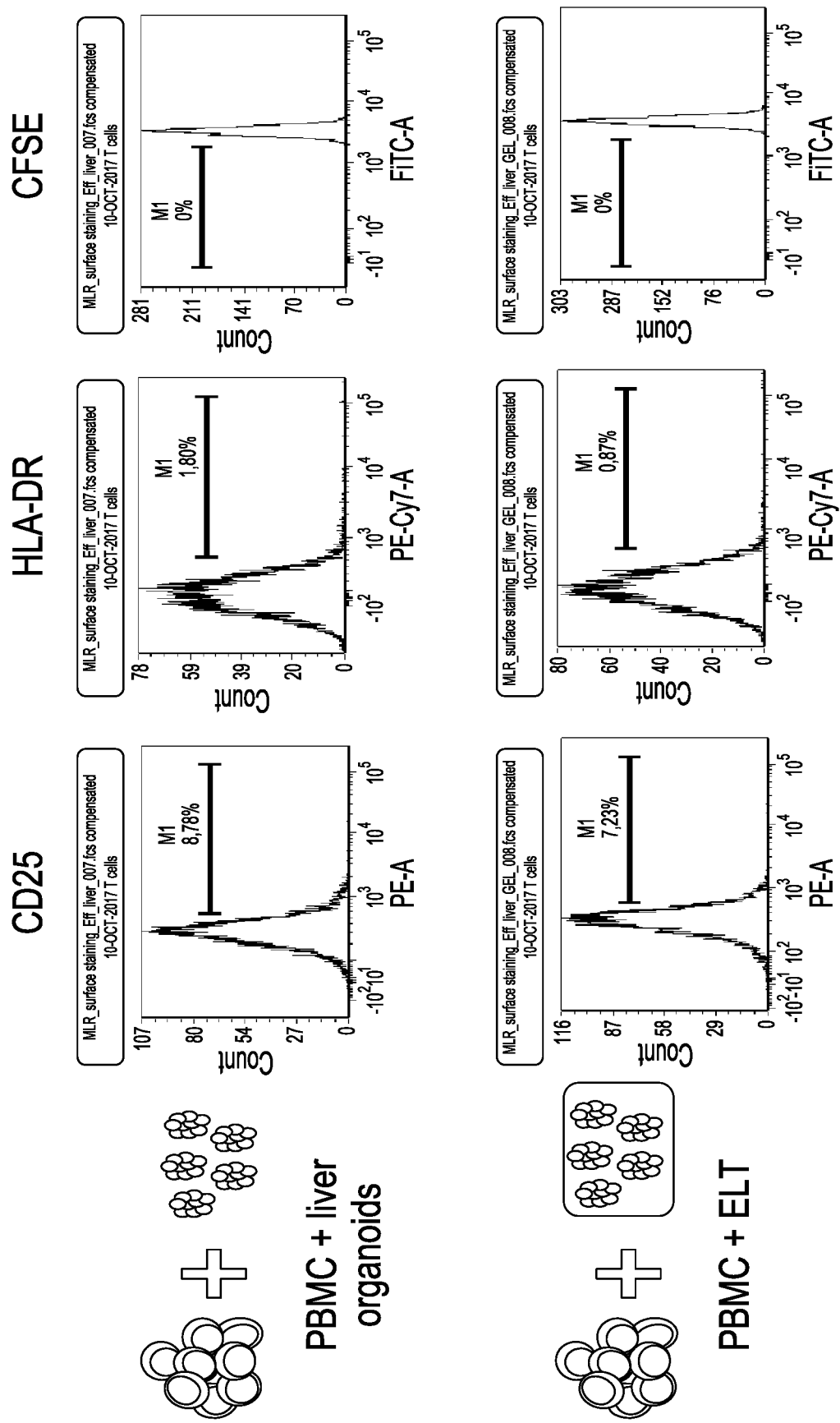
Figure 4M:
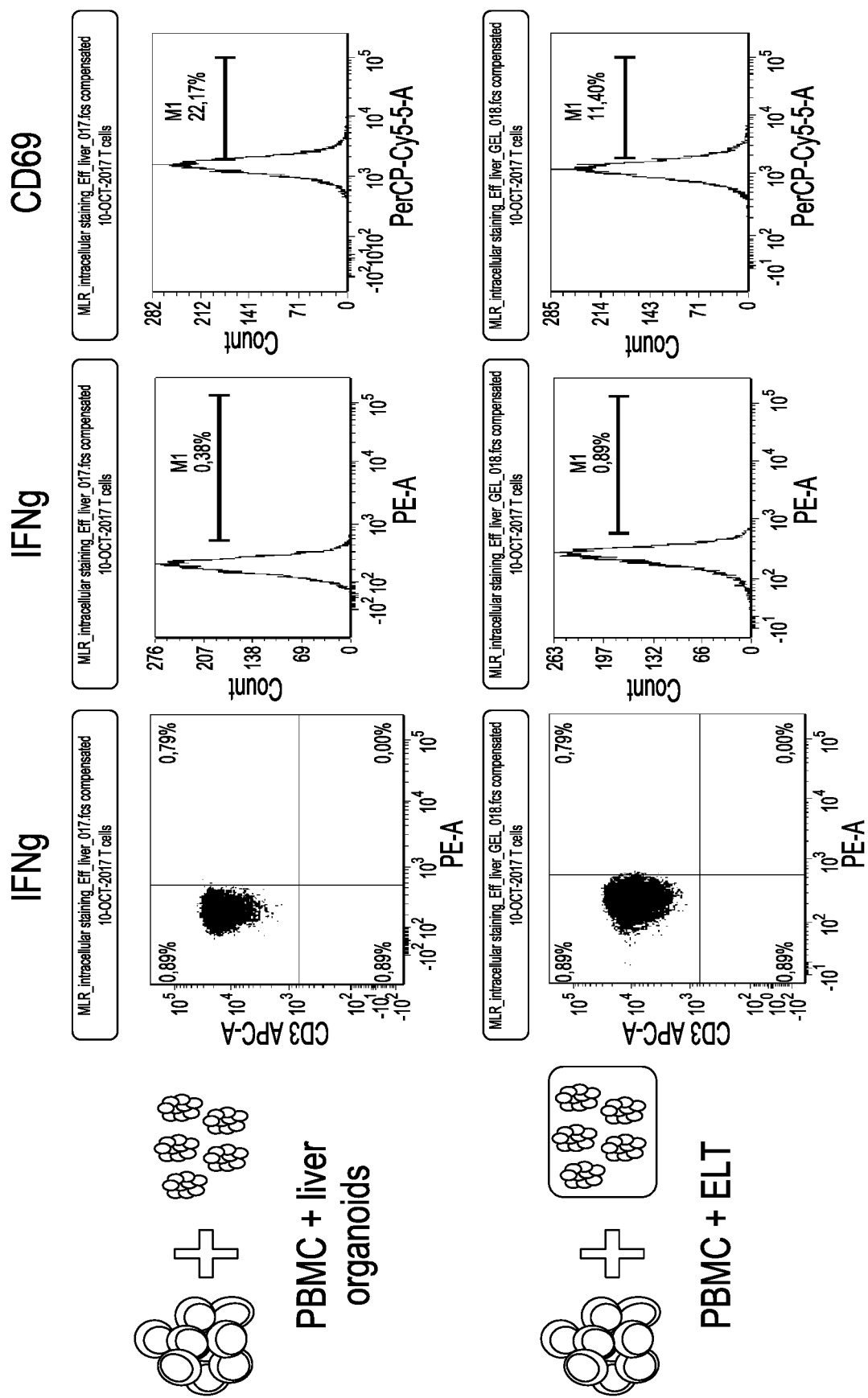
Figure 4N:
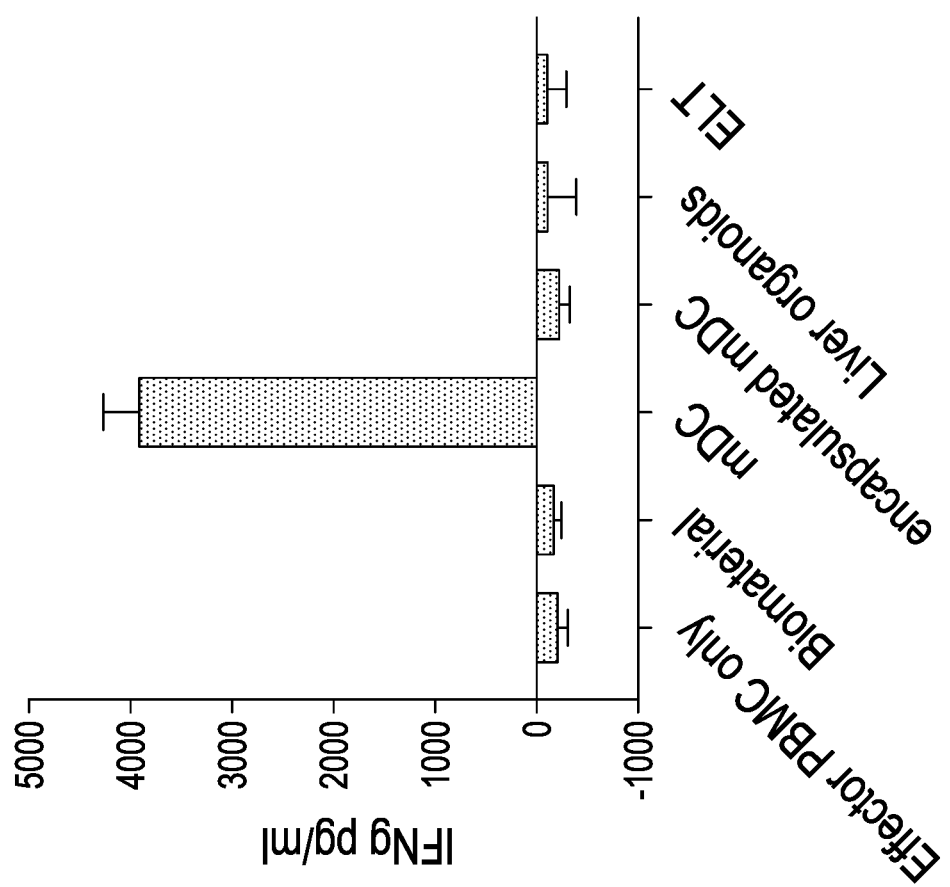
Figure 4O:
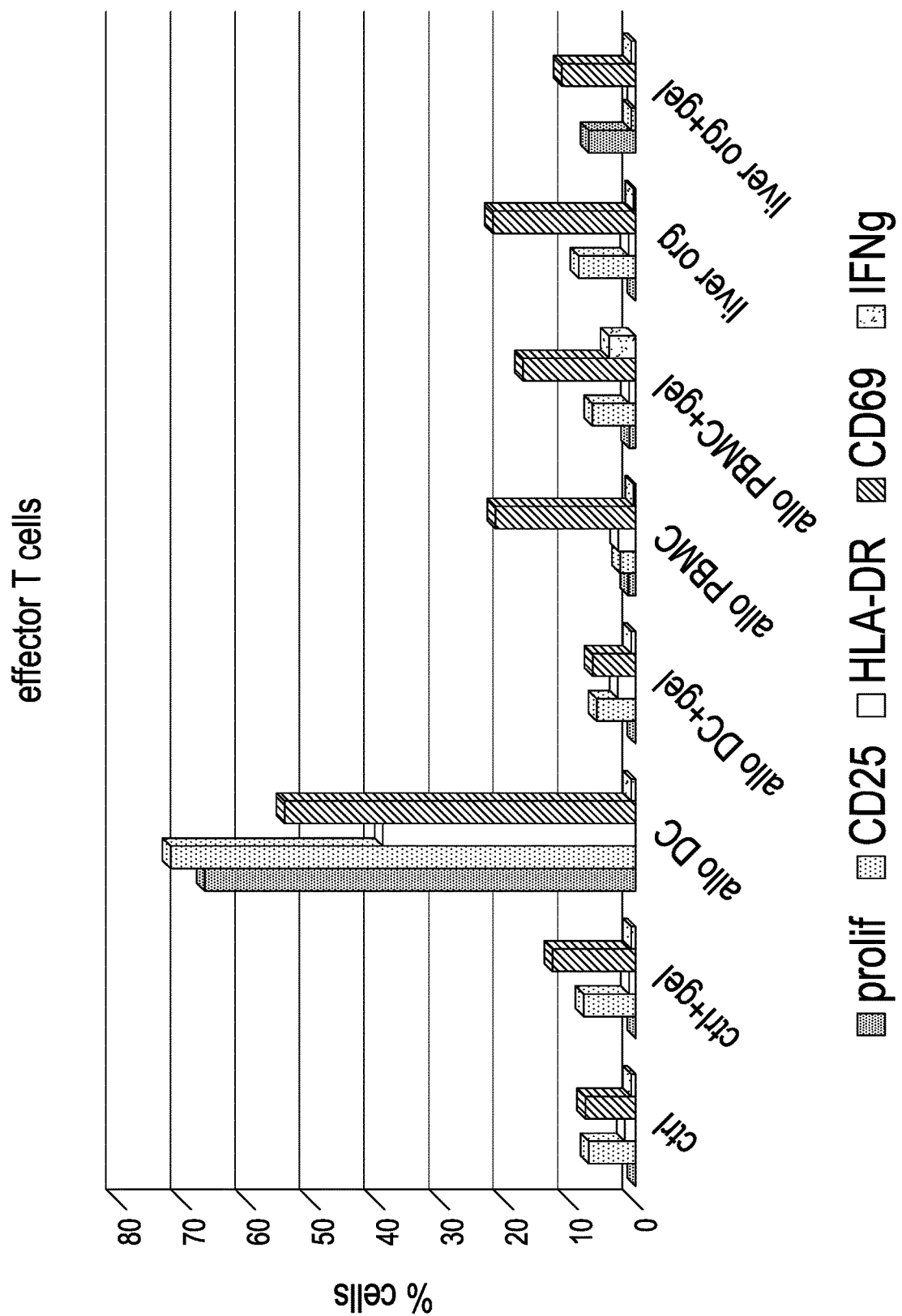

In order to foster maturation of the liver organoids and enhance their survival in vivo, an encapsulation strategy was developed (FIGS. 4A and 4B). A plurality of liver organoids (e.g. 50-150) was dispersed within liquid 5%, 20 kDa, 4-arm PEG-VS biomaterial (FIG. 4A). Photopolymerization allowed to obtain the encapsulated liver tissue (ELT), which was solid enough to be manipulated with surgical tools (FIG. 4B). Such ELT was generated either as an implantable product (8×2 mm cylindrical shape) or as an in vitro assay (in 96-well format). The encapsulation procedure did not cause significant cytotoxicity (>90% cell viability at live/ dead assay, FIG. 4C). Wthin the biomaterial, liver organoids matured significantly, while their size did not change significantly. Thirty days after encapsulation, hepatocytes were dispersed throughout the entire organoid, and bile ducts were visible (FIG. 4D). Hepatocytes matured and acquired an adult phenotype. After 7 days from encapsulation, the ELT was capable of performing mature liver functions in vitro (increasing albumin and urea secretion, CyP3A4 activity, ammonia or tacrolimus metabolism, decreasing AFP secretion) as or more efficiently than primary human hepatocytes (FIGS. 4E-4H). Albumin production, ammonia metabolism into urea were significantly more effective in the ELT than in primary hepatocytes and comparable to the human liver (12 mg of albumin/g of tissue vs. 20 mg/g of the human liver; 347 µmol ammonia/min/ implantable device vs. ~400 pmol/min/liver; FIG. 4E-4F). Tacrolimus metabolism by CyP3A4 was comparable to the human liver, and inducible by the supplementation of rifampicin (FIG. 4G). All those functions were maintained for at least 7 weeks, and stable over time (whereas primary human hepatocytes lose their metabolic activity within a few days from seeding). The ELT was capable of withstanding cryopreservation without any significant loss in its liver functions (FIG. 4H), which is not the case for primary human hepatocytes. The ELTs containing liver organoids generated from human pluripotent stem cells were implanted into the abdominal cavity of immunocompetent mice to assess its biocompatibility (FIG. 4I). No foreign body reaction was noted after 1 or 4 weeks (no adherences, no inflammation; FIG. 4J). Pluripotent stem cells used to generate the liver organoids are capable of forming teratomas upon subcutaneous injection in immunosuppressed NSG mice (FIG. 4K). Encapsulation of such pluripotent stem cells within the PEG-based biomaterial described above prevented the embedded cells from spreading into the recipient tissues, and thus prevented the formation of teratomas (FIG. 4L). This suggests that encapsulation can significantly reduce the risk of tumor formation from the implantation of stem cell-derived differentiated cells or organoids (thus suggesting an absent or low tumorigenicity of the ELT). To assess the immunogenicity of the ELT, and the immune isolation provided by encapsulation within the biomaterial, we performed a mixed lymphocyte reaction assay (FIG. 4M-4O). Non-encapsulated liver organoids showed a very low capacity of activation allogeneic effector T cells. Encapsulation prevented any contact between the encapsulated cells and the immune cells, thus preventing T cell activation. The immune isolation capabilities of the biomaterial were further confirmed through absence of T cell activation upon encapsulation of allogeneic mature dendritic cells (FIG. 4M-4O).

These data suggest that it is possible transplant an allogeneic encapsulated liver tissue without the need of immunosuppression.

Figure 4P:
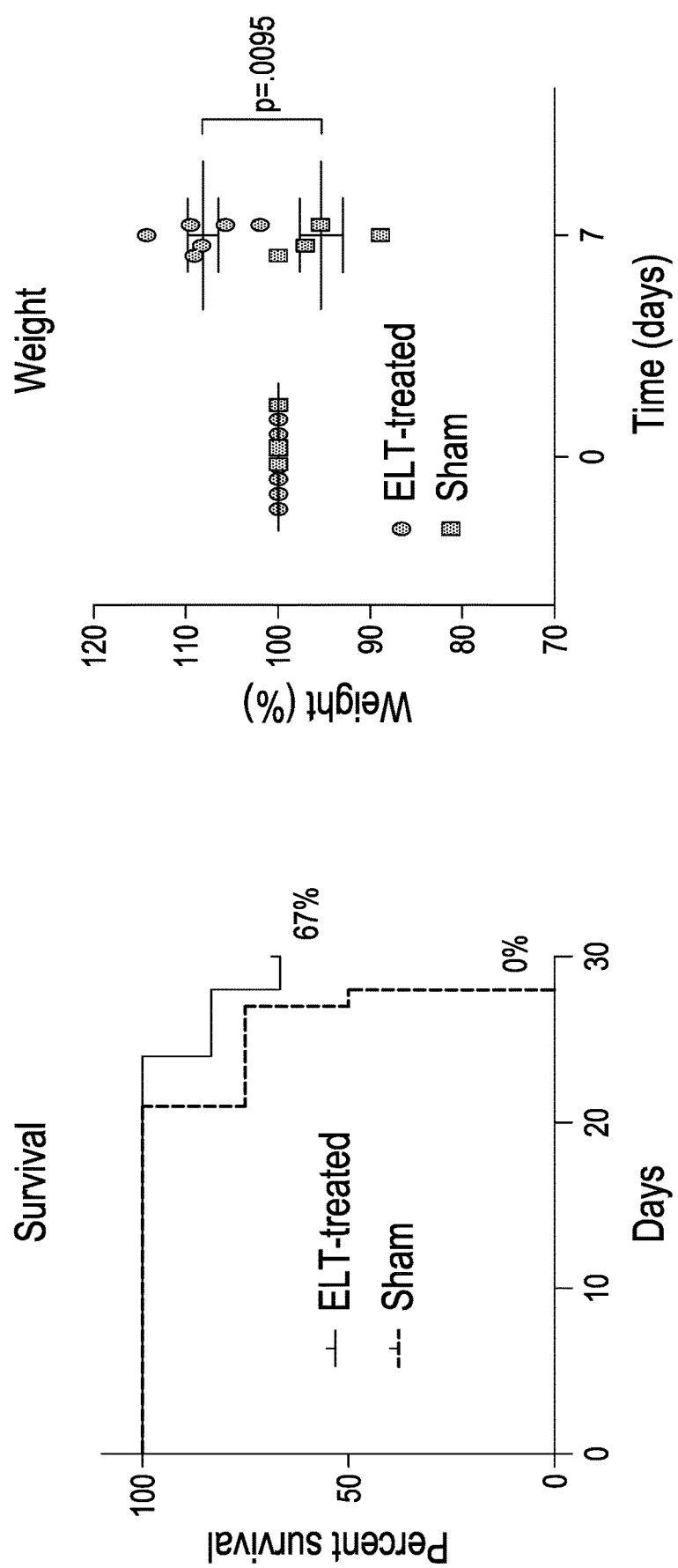
Figure 4Q:
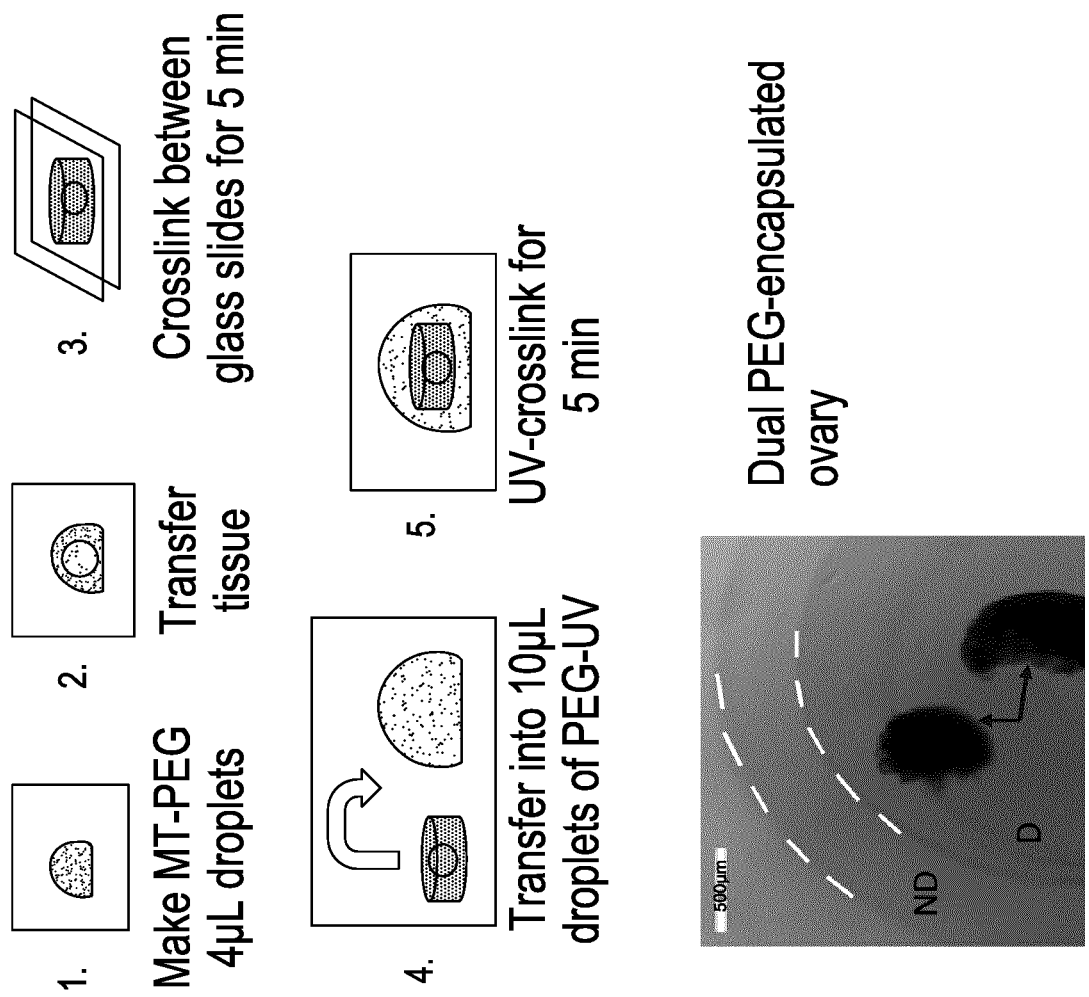

A proof-of-concept experiment was conducted in immunocompetent mice. After having induced acute liver failure in tyrosinemic $Fah^{-/-}$ mice, human ELTs were transplanted in the abdominal cavity of the animals, without immunosuppression. Mice who received the empty biomaterial served as controls. At day 7 from surgery, all mice having received the ELT gained weight, while all the controls were either stable or lost weight (FIG. 4P). Thirty days from surgery, 67% of mice having received the ELT were alive, as compared to 0% of controls. Human albumin was detected in the blood of all surviving animals at day 30. This suggests the great potential of the ELT to restore liver functions and improve survival in subjects with liver failure without the need of immunosuppression.

While the invention has been described in connection with specific embodiments thereof, it will be understood that the scope of the claims should not be limited by the preferred embodiments set forth in the examples, but should be given the broadest interpretation consistent with the description as a whole.

What is claimed is:

1. An encapsulated liver tissue sheet comprising a plurality of liver organoids at least partially covered with a first biocompatible cross-linked polymer, wherein each of the liver organoids (i) comprise a cellular core comprising hepatic, mesenchymal and optionally endothelial cells, (ii) have a substantially spherical shape, and (iii) have a relative diameter between about 50 µm and about 500 µm, wherein the encapsulated liver tissue sheet comprises at least 50 liver organoids per $cm^2$, and wherein the encapsulated liver tissue sheet has a width of at least 5 mm.

2. The encapsulated liver tissue sheet of claim 1, wherein the plurality of liver organoids are substantially covered with the first biocompatible cross-linked polymer.

3. The encapsulated liver tissue sheet of claim 1, wherein the cellular core comprises hepatocytes and/or biliary epithelial cells.

4. The encapsulated liver tissue sheet of claim 1, wherein the first biocompatible cross-linked polymer comprises poly (ethylene) glycol (PEG).

5. The encapsulated liver tissue sheet of claim 1, further comprising a second biocompatible cross-linked polymer and wherein the first biocompatible cross-linked polymer is at least partially covered by the second biocompatible cross-linked polymer.

6. The encapsulated liver tissue sheet of claim 5, wherein the second biocompatible cross-linked polymer comprises poly(ethylene) glycol (PEG).

7. A process for making an encapsulated liver tissue sheet, the process comprising:

combining and culturing in suspension hepatic and mesenchymal cells so as to obtain a plurality of liver organoids having (i) a cellular core comprising hepatic, mesenchymal and optionally endothelial cells, (ii) a substantially spherical shape, and (iii) have a relative diameter between about 50 µm and about 500 µm;

at least partially covering the plurality of liver organoids with a first biocompatible cross-linkable polymer; and forming the plurality of liver organoids at least partially covered with the first biocompatible cross-linkable polymer into a sheet form; and cross-linking the polymer so as to obtain an encapsulated liver tissue sheet comprising at least 50 liver organoids per $cm^2$ and having a width of at least 5 mm.

8. The process of claim 7, wherein the hepatic and mesenchymal cells are combined, prior to culturing, at a ratio of 1:0.2-7.

9. The process of claim 7, wherein the hepatic cells are:
(a) cells obtained from the definitive endoderm and/or the posterior foregut;
(b) hepatoblasts or liver progenitor cells; and/or
(c) hepatocytes.

10. The process of claim 7, wherein the mesenchymal cells are mesenchymal stem cells or mesenchymal progenitor cells.

11. The process of claim 7, further comprising combining and culturing the endothelial cells in suspension with the hepatic and mesenchymal cells to obtain the plurality of liver organoids comprising hepatic, mesenchymal, and endothelial cells.

12. The process of claim 11 wherein the hepatic and endothelial cells are combined, prior to culturing, at a ratio of 1:0.2-1.

13. The process of claim 11, wherein at least one of the hepatic mesenchymal and endothelial cells is obtained from differentiating a stem cell.

14. A method of restoring or improving a liver function in a subject in need thereof, the method comprising implanting an effective amount of the encapsulated liver tissue sheet of claim 1 into the subject such that the encapsulated liver tissue sheet will come into contact with a biological fluid of the subject thereby improving the liver function in the subject.

15. The method of claim 14, wherein restoring or improving the liver function is for the treatment or the alleviations of symptoms associated with liver failure.

16. The method of claim 15, wherein the liver failure is acute, chronic or acute-on-chronic liver failure.

17. A method of determining the hepatic metabolism or hepatotoxicity of an agent, the method comprising:
   a) contacting the agent with the encapsulated liver tissue sheet of claim 1 to obtain a test mixture;
   b) determining at least one agent-related hepatic metabolite or hepatic parameter in the test mixture; and
   c) comparing the at least one agent-related hepatic metabolite or hepatic parameter of step b) with a control agent-related hepatic metabolite or hepatic parameter to determine the hepatic metabolism or hepatotoxicity of the agent.

18. The method of claim 17, further defined as a method for determining if the agent induces hepatotoxicity in at least one cell type of the liver organoids of the encapsulated liver tissue sheet.

19. The method of claim 18, wherein the at least one cell type is a hepatocyte or a biliary epithelial cell.

\* \* \* \* \*

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Plasmin sensitive cross-linker

<400> SEQUENCE: 1

Gly Cys Tyr Lys Asn Ser Gly Cys Tyr Lys Asn Ser Cys Gly
1               5                   10
```